United States Patent
Blackwell et al.

(10) Patent No.: US 10,597,372 B2
(45) Date of Patent: Mar. 24, 2020

(54) SIMPLIFIED STRUCTURAL MIMETICS OF AIPS AS QUORUM SENSING INHIBITORS

(71) Applicant: Wisconsin Alumni Research Foundation, Madison, WI (US)

(72) Inventors: Helen Blackwell, Madison, WI (US); Joseph Vasquez, Madison, WI (US); Yiftah Tal Gan, Reno, NV (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 15/850,300

(22) Filed: Dec. 21, 2017

(65) Prior Publication Data

US 2018/0170889 A1 Jun. 21, 2018

Related U.S. Application Data

(60) Provisional application No. 62/437,238, filed on Dec. 21, 2016.

(51) Int. Cl.
| | | |
|---|---|---|
| C07D 291/02 | (2006.01) |
| C07D 285/00 | (2006.01) |
| C07D 273/00 | (2006.01) |
| A61P 31/04 | (2006.01) |
| C07D 417/12 | (2006.01) |

(Continued)

(52) U.S. Cl.
CPC ............ *C07D 291/02* (2013.01); *A61P 31/04* (2018.01); *C07D 273/00* (2013.01); *C07D 285/00* (2013.01); *C07D 413/12* (2013.01); *C07D 417/12* (2013.01); *C07D 419/12* (2013.01)

(58) Field of Classification Search
CPC ...... A61P 31/04; C07D 273/00; C07D 285/00; C07D 291/02; C07D 413/12; C07D 417/12; C07D 419/12
See application file for complete search history.

(56) References Cited

U.S. PATENT DOCUMENTS

| | | |
|---|---|---|
| 6,337,385 B1 | 1/2002 | Muir et al. |
| 6,953,833 B2 | 10/2005 | Muir et al. |
| 7,419,954 B2 | 9/2008 | Muir et al. |

(Continued)

FOREIGN PATENT DOCUMENTS

| | | |
|---|---|---|
| WO | WO 1999/026968 | 6/1999 |
| WO | WO 2009/154988 | 12/2009 |
| WO | WO 2017/192442 | 11/2017 |

OTHER PUBLICATIONS

George et al. (J. Am. Chem. Soc. 2008, 130, 4914-4924).*

(Continued)

*Primary Examiner* — Valerie Rodriguez-Garcia
(74) *Attorney, Agent, or Firm* — Leydig, Voit & Mayer, Ltd.

(57) ABSTRACT

Compounds that regulate quorum sensing in Staphylococcal bacteria and in particular in *Staphylococcus aureus* are provided. Compounds are described in formulas I, II, III, IV, V and VI herein. One or more compounds herein can be employed to inhibit QS and to thus inhibit virulence in *Staphylococcus* bacteria and in particular in *Staphylococcus aureus*. Compounds herein and pharmaceutical compositions containing one or more of these compounds are useful, for example, in treating infections of *Staphylococcus* bacteria and in particular of *Staphylococcus aureus*. Methods for treating such bacterial infections are provided.

43 Claims, 21 Drawing Sheets

Specification includes a Sequence Listing.

n=5: n5FF  n=8: n8FF
n=6: n6FF  n=9: n9FF
n=7: n7FF n7OFF n=7: n7FF amide
n=8: n8FF amide n7OFF amide

(51) Int. Cl.
C07D 413/12 (2006.01)
C07D 419/12 (2006.01)

(56) References Cited

U.S. PATENT DOCUMENTS

| | | | |
|---|---|---|---|
| 8,168,397 | B2 | 5/2012 | Charlton et al. |
| 9,227,996 | B2 | 1/2016 | Blackwell et al. |
| 2007/0185016 | A1 | 8/2007 | Muir et al. |
| 2014/0256615 | A1* | 9/2014 | Blackwell ............... C07K 5/12 514/2.7 |
| 2016/0194360 | A1 | 7/2016 | Blackwell et al. |

OTHER PUBLICATIONS

U.S. Appl. No. 13/792,977, filed May 11, 2013, Abandoned.
U.S. Appl. No. 14/109,192, filed Dec. 17, 2013, Granted, U.S. Pat. No. 9,227,996, Jan. 5, 2016.
U.S. Appl. No. 14/987,457, filed Jan. 4, 2016, Pending.
U.S. Appl. No. 16/098,394, filed Nov. 1, 2018, Pending.
Amara et al. (published online Nov. 18, 2010) "Macromolecular Inhibition of Quorum Sensing: Enzymes, Antibodies, and Beyond," Chem. Rev. 111(1):195-208.
Aurelio, Luigi et al, "Synthetic preparation of n-methyl alpha amino acids." Chem. Rev. (2004) 104 p. 5823-5846.
Biron & Kessler (May 2005) "Convenient Synthesis of N-Methylamino Acids Compatible with Fmoc Solid-Phase Peptide Synthesis," J. Organic Chem. 70:5183-5189.
Broderick et al. (Jun. 2013) "Surface Coatings that Promote Rapid Release of Peptide-Based AgrC Inhibitors for Attenuation of Quorum Sensing in Staphylococcus aureus." Adv. Healthcare Mater. 3:97-105.
Chan et al. (Sep. 2004) "Virulence Regulation and Quorum Sensing in Staphylococcal Infections: Competitive AgrC Antagonists as Quorum Sensing Inhibitors," J. Med. Chem. 47(19):4633-4641.
Fowler et al. (May 2008) "Design and Synthesis of Macrocyclic Peptomers as Mimics of a Quorum Sensing Signal from Staphylococcus aureus," Org. Lett. 10(12):2329-2332.
George et al. (Mar. 2008) "Cyclic Peptide Inhibitors of Staphylococcal Virulence Prepared by Fmoc-Based Thiolactone Peptide Synthesis," J. Am. Chem. Soc. 130(14):4914-4924.
George et al. (May 2007) "Molecular Mechanisms of agr Quorum Sensing in Virulent Staphylococci," ChemBioChem. 2007, 8, 847-855.
Ghose et al. (1999) "A Knowledge-Based Approach in Designing Combinatorial or Medicinal Chemistry Libraries for Drug Discovery", J. Combin. Chem., 1(1):55-68.
Gorske et al. (Mar. 2006) "Interception of Quorum Sensing in Staphylococcus aureus: A New Niche for Peptidomimetics," Org. Biomol. Chem. 4:1441-1445.
Jarraud et al. (Nov. 2000) "Exfoliatin-Producing Strains Define a Fourth agr Specificity Group in Staphylococcus aureus," J. Bacteriol. 182(22):6517-6522.
Ji et al. (Jun. 1997) "Bacterial Interference Caused by Autoinducing Peptide Variants," Science. 276(5321):2027-2030.
Johnson et al. (May 2015) "Increasing AIP Macrocycle Size Reveals Key Features of agr Activation in S. aureus". 16, 1093-1100.
Kaufmann et al. (Jun. 2008) "Bacterial Quorum Sensing: A New Target for Anti-Infective Immunotherapy," Exp. Opin. Biol. Ther. 8(6)719-724.
Kirchdoerfer et al. (Mar. 2011) "Structural Basis for Ligand Recognition and Discrimination of a Quorum-Quenching Antibody," J. Biol. Chem. 286(19):17351-17358.
Kratochvil et al. (2015) "Nanoporous Superhydrophobic Coatings that Promote the Extended Release of Water-Labile Quorum Sensing Inhibitors and Enable Long-Term Modulation of Quorum Sensing in Staphylococcus aureus". ACS Biomat. Sci. Eng. 1, 1039-1049.
Le et al. (Oct. 2015) "Quorum-sensing regulation in staphylococci—an overview". Front Microbiol. 6, 1174.
Li et al. (Feb. 2011) "Lactobacillus reuteri-Produced Cyclic Dipeptides Quench agr-Mediated Expression of Toxic Shock Syndrome Toxin-1 in Staphylococci," Proc. Natl. Acad. Sci. U. S. A. 2011, 108, 3360-3365.
Lyon et al. (Aug. 6, 2002) "Key Determinants of Receptor Activation in the agr Autoinducing Peptides of Staphylococcus aureus," Biochemistry. 41(31):10095-10104.
Lyon et al. (Feb. 2002) "Reversible and Specific Extracellular Antagonism of Receptor-Histidine Kinase Signaling". J. Biol. Chem. 277, 6247-6253.
Lyon et al. (Nov. 2000) "Rational Design of a Global Inhibitor of the Virulence Response in Staphylococcus aureus, Based in Part on the Localization of the Site of Inhibition to the Receptor-Histidine Kinase, AgrC," Proc. Natl. Acad. Sci. U. S. A. 2000, 97, 13330-13335.
Lyon et al. (Sep. 2004) "Peptide Signaling in Staphylococcus aureus and Other Gram-positive Bacteria," Peptides. 25(9):1389-1403.
Malone et al. (Aug. 2007) "Biosynthesis of Staphylococcus aureus Autoinducing Peptides by Using the Synechocystis DnaB Miniintein," Appl. Environ. Microbiol. 73:6036-6044.
Mayville et al. (Feb. 1999) "Structure-Activity Analysis of Synthetic Autoinducing Thiolactone Peptides from Staphylococcus aureus Responsible for Virulence," Proc. Natl. Acad. Sci. U. S. A. 1999, 96, 1218-1223.
McDowell et al. (Jul. 2001) "Structure, Activity and Evolution of the Group I Thiolactone Peptide Quorum-Sensing System of Staphylococcus aureus," Mol. Microbiol. 41(2):503-512.
Novick, Richard P. and Geisinger, Edward; "Quorum sensing in staphylococci." Annu. Rev. Genet. (2008) 42 p. 541-64.
Rasko et al. (Jan. 2010) "Anti-virulence strategies to combat bacteria-mediated disease," Nat. Rev. Drug Disc. 9(2):117-128.
Scott et al. (May 2003) "Side-Chain-to-Tail Thiolactone Peptide Inhibitors of the Staphylococcal Quorum-Sensing System." Med. Chem Lett. 13, 2449-2453.
Sintim et al. (Jun. 2010) "Paradigm Shift in Discovering Next-Generation Anti-Infective Agents: Targeting Quorum Sensing, c-di-GMP Signaling and Biofilm in Bacteria with Small Molecules," Future Med. Chem. 2010, 2, 1005-1035.
Stacy (Apr. 6, 2012) "Attenuation of Quorum Sensing and Virulence in the Pathogen Staphylococcus aureus Using Synthetic Autoinducer Mimics," In; The Lincoln Seminar Series. The University of Wisconsin—Madison. Madison, Wisconsin.
Stacy et al. (Apr. 13, 2012) "Attenuation of Quorum Sensing and Virulence in the Pathogen Staphylococcus aureus Using Synthetic Autoinducer Mimics," In; Perlman Symposium on Antibiotic Discovery and Development. Madison, Wisconsin.
Stevens et al. (Dec. 2010) "Mechanisms and synthetic modulators of AHL-dependent gene regulation," Chem. Rev. 111(1):4-27.
Tal-Gan et al. (Aug. 7-8, 2008) "The Application of Peptidomimetics to Study Quorum Sensing in Staphylococcus aureus," In; The 6$^{th}$ Peptoid Summit. Berkeley, California.
Tal-Gan et al. (Feb. 18-19, 2012) "Development of Peptide-Based Tools to Study Quorum Sensing in Staphylococcus aureus," In; Gordon Research Conference: Peptides, Chemistry and Biology of (GRS). Ventura, California.
Tal-Gan et al. (May 2013) "Highly Potent Inhibitors of Quorum Sensing in Staphylococcus aureus Revealed Through a Systematic Synthetic Study of the Group-III Autoinducing Peptide," J. Amer. Chem. Soc. 135(21):7869-7882.
Tal-Gan et al. (Nov. 2013) "Structural Characterization of Native Autoinducing Peptides and Abiotic Analogues Reveals Key Features Essential for Activation and Inhibition of an AgrC Quorum Sensing Receptor in Staphylococcus aureus" J. Am. Chem. Soc.135 (49):18436-18444.
Tal-Gan et al. (Jan. 2014) "N-Methyl and peptoid scans of an autoinducing peptide reveal new structural features required for inhibition and activation of AgrC quorum sensing receptors in Staphylococcus aureus" Chem. Comm. 50:3000-3003.
Tal-Gan et al. (Jan. 2016) "Characterization of Structural Elements in Native Autoinducing Peptides and Non-Native Analogues that Permit the Differential Modulation of AgrC-type Quorum Sensing Receptors in Staphylococcus aureus". Org Biomol. Chem. 14, 113-121.

(56) References Cited

OTHER PUBLICATIONS

Tal-Gan et al. (Jul. 2016) "Highly Stable, Amide-Bridged Autoinducing Peptide Analogues that Strongly Inhibit the AgrC Quorum Sensing Receptor in *Staphylococcus aureus*". Angew Chem. Int. Ed Engl. 55.

Thoendel et al. (Dec. 2010) "Peptide Signaling in the Staphylococci," Chem. Rev. 111(1):117-151.

Vasquez et al. (Feb. 2017) "Simplified AIP-II Peptidomimetics are Potent Inhibitors of *Staphylococcus aureus* AgrC Quorum Sensing Receptors". ChemBioChem. 18, 413-423.

Wang et al. (Mar. 2014) "Activation and Inhibition of the Receptor Histidine Kinase AgrC Occurs through Opposite Helical Transduction Motions". Mol. Cell 53, 929-940.

Wang et al. (Feb. 2016) "Regulation of virulence in *Staphylococcus aureus*: molecular mechanisms and remaining puzzles". Cell Chem. Biol. 23, 214-224.

Wright et al. (Nov. 2004) "Hydrophobic Interactions Drive Ligand-Receptor Recognition for Activation and Inhibition of Staphylococcal Quorum Sensing," *Proc. Natl. Acad. Sci. U. S. A*. 101 (46):16168-16173.

Wright et al. (Feb. 2005) "Transient interference with staphylococcal quorum sensing blocks abscess formation". Proc. Natl. Acad. Sci. U.S.A. 1691-1696.

Yang et al. (Jul. 2016) "Structure-Function Analyses of a *Staphylococcus epidermidis* Autoinducing Peptide Reveals Motifs Critical for AgrC-type Receptor Modulation". ACS Chem. Biol. 1-24.

Boles et al. (2008) "agr-mediated dispersal of *Staphylococcus aureus* biofilms," PLoS Path. 4:e1000052, 1-13.

Lyon et al. (2004) "Peptide signaling in *Staphylococcus aureus* and other Gram-positive bacteria," Peptides 25:1389-1403.

Otto et al. (1998) "Structure of the pheromone peptide of the *Staphylococcus epidermidis agr* system," FEBS Lett. 424:89-94.

Otto et al. (1999) "Inhibition of virulence factor expression in *Staphylococcus aureus* by the *Staphylococcus epidermidis agr* pheromone and derivatives," FEBS Lett. 450:257-262.

Otto et al. (2001) "Pheromone cross-inhibition between *Staphylococcus aureus* and *Staphylococcus epidermidis*," Infect. Immun. 69:1957-1960.

Rutherford et al. (2012) "Bacterial quorum sensing: its role in virulence and possibilities for its control," Cold Spring Harb. Perspect. Med. 2:a012427, 1-25.

Yin (2012) "constrained peptides as miniature protein structures," ISRN Biochem. Article ID 692190, 1-15.

Leeson et al. (2007) "The influence of drug like concept on decision making in medicinal chemistry," Nat. Rev. Drug Discover. 6: 881-890.

Vasquez et al. (Feb. 2019) "Simplified Autoinducing Peptide Mimetics with Single-Naonomolar Activity Against the *Staphylococcus aureus* AgrC Quorum Sensing Receptor," ACS Infect. Dis. 5:484-492.

\* cited by examiner

US 10,597,372 B2

SIMPLIFIED STRUCTURAL MIMETICS OF AIPS AS QUORUM SENSING INHIBITORS

CROSS-REFERENCE TO RELATED APPLICATIONS

This application claims the benefit of U.S. Provisional Application 62/437,238, filed Dec. 21, 2016, which is incorporated by reference herein in its entirety.

STATEMENT REGARDING FEDERALLY SPONSORED RESEARCH OR DEVELOPMENT

This invention was made with government support under N00014-14-1-0791 and N00014-16-1-2185 awarded by the NAVY/ONR. The government has certain rights in the invention.

BACKGROUND

Quorum sensing (QS) allows bacteria to behave as a group at high cell densities and is closely connected to virulence in many common pathogens. [1] This intercellular communication system is mediated by small molecule or peptide signals that diffuse out of or are secreted by bacteria into the local environment. As the population grows, the concentration of QS signal increases until a threshold is reached, whereupon the signal can productively bind to its cognate receptor. The activated receptor then modifies gene expression levels to let the bacteria adopt a community lifestyle, while simultaneously increasing production of the QS circuitry and thus amplifying the QS response. [1a]

For many pathogens, QS allows bacteria to amass a sufficiently high population prior to initiating virulence phenotypes, thereby increasing their chances to successfully infect a host. [1a, 2] The close connection been QS and bacterial infection, and perhaps more fundamentally, the chemical nature of QS signaling, has inspired considerable recent research to design chemical strategies to intercept QS pathways. [3] Many of these efforts have focused on the development of synthetic mimics of QS signals that can inhibit QS receptor:signal binding, for use as chemical probes to block virulence phenotypes, and to delineate basic QS mechanisms. [1a, 4, 5] Efforts include those directed to the common pathogen *Staphylococcus aureus* [4f-l, 4k, 4l, 6] and related species. [4j]

In the *staphylococci*, QS is controlled by the accessory gene regulator (agr) system. [5t, 7] In the case of *S. aureus*, this QS system controls the expression of over 100 virulence factors. [7b, 8] The *S. aureus* agr machinery is composed of four proteins, AgrA-D, and a signaling molecule (derived from AgrD) termed an autoinducing peptide (or AIP; FIG. 1A). [9]

AgrD is the precursor to the QS signal, which is processed by AgrB and secreted as the mature AIP (FIG. 1A). [5t, 7, 9a, 10] The *S. aureus* AIP is a small macrocyclic peptide (7-9 residues), containing a short N-terminal tail and a thiolactone bridge between an internal Cys side chain and the C-terminus. [5j, 9a] To date, four specificity subgroups of *S. aureus* have been characterized (groups I-IV), each defined by the unique peptide sequence of their AIPs (shown in FIG. 1B) and their target transmembrane receptor and histidine kinase, AgrC. [9a, 11] When a threshold extracellular AIP concentration is reached, the peptide signal binds and activates AgrC. AgrC then phosphorylates and thereby activates its partner response regulator, the transcription factor AgrA. [5o] AgrA subsequently targets several promoters, including P2 and P3. P2 induces transcription of the agr operon, and provides positive feedback for the autoinduction circuit. [9b] In turn, P3 drives transcription of RNA-III, which is a major regulator of virulence factor production in *S. aureus*. [12]

Blocking AgrC:AIP binding represents one strategy to attenuate QS signaling in *S. aureus*, and this approach has been the focus of considerable research. [4g, 4l, 5t, 7a, 7b] The initial discovery that AIP-I and AIP-II inhibit AgrC activity in non-self Agr specificity groups was followed by study of AIP derivatives with tail-truncations, sequential Ala scans, and other amino acid substitutions to identify key structure-activity relationships (SARs) dictating ligand and receptor activity. [5j-l, 5q, 7b] These early SAR studies suggested that the AIP ligand-binding site on AgrC was a hydrophobic cleft that could be a viable target for competitive inhibition with hydrophobic, peptidic ligands. [5l, 5m, 13] Additional screening with tail-truncated AIPs resulted in further refinement of the SARs for AgrC activation and inhibition, suggesting that the presence of only two hydrophobic C-terminal groups within ligands was required for AgrC binding, while additional contacts on the N-terminal tail were needed for receptor activation. [5l, 5n]

Tail-truncated AIP-II (t-AIP-II) was found to be quite potent amongst this class. [5l, 5n] Recently, similar SAR studies were extended to *S. aureus* AIP-III, which found a similar activity trend; namely, hydrophobic endocyclic residues were required for AgrC binding, while exocyclic tail contacts along with the hydrophobic motifs were required for activation. [4g-i, 4k, 4l] Studies with AIP-III and mimetics thereof identified a number of highly potent, pan-group AgrC inhibitors, with AIP-III D4A (IN(CAFLL) SEQ ID NO:6) being one of the most potent AgrC inhibitors reported to date. [4g]

Despite their potency, however, peptidic AgrC modulators possess several qualities that limit their utility as chemical tools. First, the AIP thiolactone bridges are hydrolytically unstable. [4l, 6a, 14] Second, while their macrocyclic framework renders AIPs more proteolytically stable than linear peptides, they are still susceptible to proteolysis. [4l, 15] Third, AIP-type peptides have relatively low water solubilities due to their hydrophobic structures. Fourth, these ligands are typically prepared using solid-phase synthesis techniques that do not lend themselves easily to large batch synthesis. The development of lactam-bridged AIP-III mimetics has begun to address some of these limitations; [4l] however, significant challenges certainly remain.

Thus, there is a need in the art for non-peptide, small molecule mimetics of AIPs that display enhanced stabilities and aqueous solubilities, reduced immunogenicity, and are amendable to larger scale synthesis relative to peptides.

SUMMARY

The invention relates to the development of structurally simplified AIP mimetics that modulate AgrC activity in *S. aureus*, and more specifically, inhibit ArgC activity in *S. aureus*. Screening of compounds herein in the four agr groups of *S. aureus* for AgrC inhibition provides compounds that are pan-group inhibitors (inhibitors of all four groups), and potent inhibitors maintaining potency within a factor of seven of the corresponding natural AIP peptide in each of the four groups.

The invention provides compounds that are useful for bacterial interference. The invention provides compounds that are useful in the treatment of bacterial infection and related conditions and/or compounds that are useful in the treatment of "staph" infections (infections caused by *Staphylococcus* bacteria) and particularly infections of *Staphylococcus aureus*.

The invention provides compounds that affect quorum sensing (QS) in *Staphylococcus aureus* and related *Staphylococcus* species (e.g., *S. epidermidis*). More specifically, the invention provides compounds that modulate one or more of the four AgrC receptors of *Staphylococcus* species, particularly of *Staphylococcus aureus*. Modulation includes inhibition or activation of one or more of these four AgrC receptors. In specific embodiments, compounds that inhibit one of the AgrC receptors are provided. In specific embodiments, compounds that inhibit two of the AgrC receptors are provided. In specific embodiments, compounds that inhibit three of the AgrC receptors are provided. In specific embodiments, compounds that inhibit three or four of the AgrC receptors are provided. In additional embodiments, compounds that inhibit all four of the AgrC receptors are provided.

Certain compounds of the invention can block hemolysis by wild-type *Staphylococcus aureus*, which is a virulence phenotype under the control of QS. Certain compounds of the invention can reduce Toxic shock syndrome toxin-1 (TSST-1) production levels in a wild-type *Staphylococcus aureus* group-III strain.

In specific embodiments, compounds of the invention are useful for the treatment of infections involving *Staphylococcus aureus* agr group-III strains and particularly for the treatment of Toxic shock syndrome. In specific embodiments, compounds that modulate QS in *Staphylococcus aureus* agr group-III strains are provided. In specific embodiments, compounds that inhibit QS in *Staphylococcus aureus* agr group-III strains are provided.

In specific embodiments, compounds of the invention modulate biofilm formation by *Staphylococcus* species, particularly by *Staphylococcus aureus* and more particularly by specific *Staphylococcus aureus* group strains. In specific embodiments, compounds of the invention modulate biofilm formation by *Staphylococcus aureus* agr group-III strains.

Compounds of the invention include those of formula I:

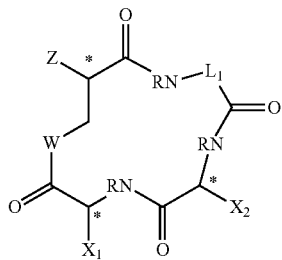

or salts or solvates thereof,
where:
carbons indicated by * are independently in the L- or R-stereochemical form and the compound can be racemic, non-racemic or substantially enantiomerically pure.

W is S or $NR_1$, or —W—CO— is —CH=CH—, where $R_1$ is hydrogen or an alkyl group having 1 to 3 carbon atoms, with methyl being the preferred alkyl group;

Z is —$NR_3CO$—$R_2$, where $R_3$ is hydrogen or a C1-C3 alkyl, $R_2$ is hydrogen, an optionally-substituted alkyl group having 1-12 carbon atoms (preferably 2-10 carbon atoms), an optionally-substituted cycloalkyl group having 3-12 carbon atoms; an optionally-substituted arylalkyl group an optionally-substituted heteroarylalkyl group, an optionally-substituted heterocycylalkyl, an optionally-substituted cycloalkyl-substituted alkyl group; an optionally-substituted aryl, an optionally-substituted heteroaryl group, an optionally-substituted heterocycyl group or an alkoxyalkyl group having 1-12 carbon atoms and 1-4 oxygen atoms;

$L_1$ is a divalent linker which contains 1-12 carbon atoms, optionally 1-4 oxygen atoms, optionally one or two carbon-carbon double bonds, and hydrogen atoms to satisfy valency; each R, independently, is hydrogen or an straight-chain or branched alkyl group having 1-3 carbon atoms, with methyl being the preferred alkyl group; and $X_1$ and $X_2$ are independently selected from the group consisting of optionally-substituted straight-chain or branched alkyl groups having 3-8 carbon atoms, optionally-substituted cycloalkyl groups having 3-12 carbon atoms; optionally-substituted aryl, optionally-substituted heteroaryl, optionally-substituted heterocycyl, optionally-substituted cycloalkylalkyl, optionally-substituted arylalkyl, optionally-substituted heteroarylalkyl and optionally-substituted heterocycylalkyl groups.

In specific embodiments, $X_1$ and $X_2$ are selected from optionally-substituted straight-chain or branched alkyl groups having 3-8 carbon atoms, optionally-substituted cyclyohexyl methyl, optionally-substituted cyclopentylmethyl, optionally substituted cyclohexyl, optionally-substituted cyclopentyl, optionally-substituted benzyl and optionally-substituted indolyl groups.

In specific embodiments, $L_1$ is a divalent linker which is an alkylene having 1-12 carbon atoms. In specific embodiments, $L_1$ is a divalent linker which is an alkenylene having 1-12 carbon atoms. In specific embodiments, $L_1$ is a divalent linker which is an alkoxyalkylene having 1-12 carbon atoms and having 1-4 oxygen atoms. In specific embodiments, $L_1$ is other than a —$CH_2$— group. In specific embodiments, $L_1$ is other than a —$CH_2$—O— group. In specific embodiments, $L_1$ is —$(CH_2)_n$—, where n is 5, 6, 7, 8 or 9. In more specific embodiments, $L_1$ is —$(CH_2)_n$—, and n is 6. In more specific embodiments, $L_1$ is —$(CH_2)_n$— and n is 7. In more specific embodiments, $L_1$ is —$(CH_2)_n$—, and n is 8. In more specific embodiments, $L_1$ is —$(CH_2)_n$—, and n is 9.

In specific embodiments, W is S. In specific embodiments, W is —NH—. In specific embodiments, W is —$N(CH_3)$—. In specific embodiments, —W—CO— is a carbon-carbon double bond (—CH=CH—). More specifically, —W—CO— is a trans-carbon-carbon double bond:

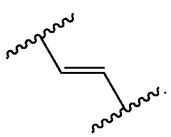 [SMILES: */C=C/*]

In a specific embodiment, when W is $NR_1$, $L_1$ is —$(CH_2)_n$—, where n is 5, 6, 7, 8 or 9. In more specific embodiments, when W is $NR_1$, $L_1$ is —$(CH_2)_6$—. In more specific embodiments, when W is $NR_1$, $L_1$ is —$(CH_2)_7$—. In more specific embodiments, when W is $NR_1$, $L_1$ is —$(CH_2)_8$—. In more specific embodiments, when W is $NR_1$, $L_1$ is —$(CH_2)_9$—.

In specific embodiments, Z is —NHCO—$R_2$. In specific embodiments, Z is —$N(CH_3)CO$—$R_2$.

In specific embodiments, all of the amino acid groups in Formula I are in the L-configuration. In specific embodiments, one of the amino acids of formula I are in the R-configuration. In specific embodiments, one of the amino acids of formula I are in the L-configuration. In specific embodiments, one of the amino acids of formula I are in the R-configuration.

In specific embodiments, salts are pharmaceutically acceptable salts.

In specific embodiments, solvates are pharmaceutically acceptable. In specific embodiments, solvates are hydrates.

The invention also relates to pharmaceutical compositions comprising one or more compounds of Formula I, Formula V, Formula VI, Formula II or Formula III (below) or dimers thereof. Such pharmaceutical compositions can further comprise a pharmaceutically acceptable carrier. Such pharmaceutical compositions are useful for the treatment of infections of Staphylococcus species and particularly of infections S. aureus and S. epidermidis.

BRIEF DESCRIPTION OF THE DRAWINGS

FIG. 1A is a schematic representation of the agr QS circuit in S. aureus. In FIG. 1A, a: The agr operon is expressed to make the Agr proteins A-D. In FIG. 1A, b and c: The AIP precursor AgrD is processed by AgrB and the mature AIP is transported out of the cell. In FIG. 1A, d: The AIP binds to AgrC, a transmembrane histidine kinase and preformed dimer. In FIG. 1A, e: AgrC phosphorylates and activates AgrA, the response regulator. In FIG. 1A, f: AgrA binds promoters P2 and P3 and initiates transcription. P2 upregulates the agr system and thus activates a positive QS feedback circuit, while P3 induces transcription of RNAIII, the direct and indirect effector of many virulence phenotypes. FIG. 1B illustrates the structures of the four known S. aureus AIPs (I-IV): AIP-I (SEQ ID NO:1); AIP-II (SEQ ID NO:2); AIP-III (SEQ ID NO: 3); AIP-IV (SEQ ID NO:4). Single letter codes are used for amino acid residues.

FIG. 2A illustrates the structure of t-AIP-II (SEQ ID NO:5) and its reduction to an exemplary minimized scaffold. FIG. 2B illustrates structures of selected t-AIP-II mimetics with potencies and/or structural features of interest.

DETAILED DESCRIPTION

Figure 1A:
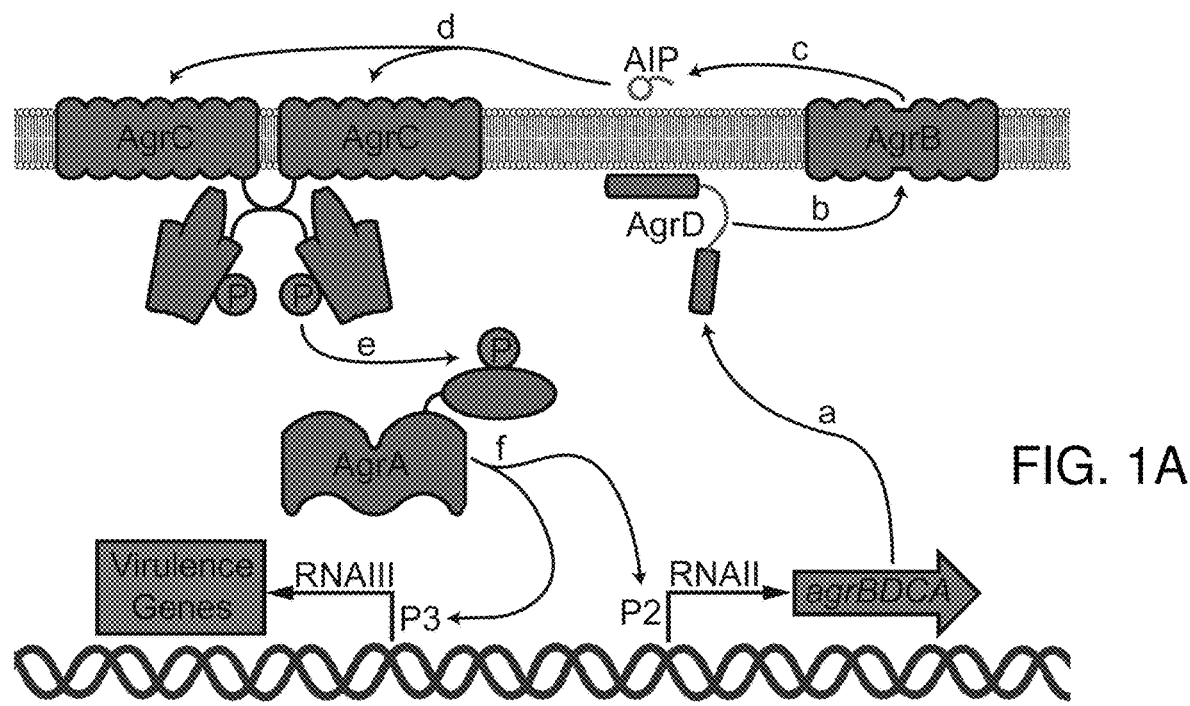
FIGS. 1A and 1B.

The prevalent human pathogen, Staphylococcus aureus, controls many aspects of virulence using the accessory gene regulator (agr) quorum sensing (QS) system. The agr system is activated by a macrocyclic peptide signal known as an autoinducing peptide (AIP). This invention relates to structurally simplified mimetics of AIPs as modulators of virulence in S. aureus and more specifically to inhibitors of virulence in S. aureus.

Compounds herein function for controlling aspects of virulence in S. aureus. Compounds herein function for controlling virulence phenotypes in S. aureus. Compounds herein function for controlling the expression of virulence factors in S. aureus. Control and modulation with respect to virulence, virulence phenotypes, and virulence factors include both activation or induction, as well as inhibition or suppression. In addition, the modulators herein can be used as research tools to study QS in S. aureus.

More specifically, peptidomimetic AgrC receptor inhibitors based on a tail-truncated AIP-II peptide are disclosed. Certain modulators herein have almost analogous inhibitory activity to the parent tail-truncated AIP-II peptide.

Compounds of the invention include those of formula I:

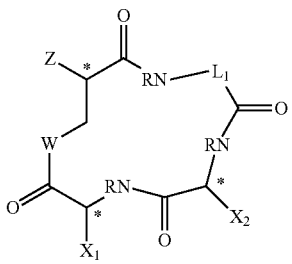

where:

carbons indicated by * are independently in the L- or R-stereochemical form and the compound can be racemic, non-racemic or enantiomerically pure.

W is S or $NR_1$, or —W—CO— is —CH=CH—, where $R_1$ is hydrogen or an alkyl group having 1 to 3 carbon atoms, with methyl being the preferred alkyl group;

where $R_1$ is hydrogen or an alkyl group having 1 to 3 carbon atoms, with methyl being the preferred alkyl group;

Z is —$NR_3CO$—$R_2$ where R3 is hydrogen or an alkyl groups having 1-3 carbon atoms. $R_2$ is hydrogen, an optionally-substituted alkyl group having 1-12 carbon atoms (preferably 2-10 carbon atoms), an optionally-substituted cycloalkyl group (preferably cyclohexyl or cyclopentyl); an optionally-substituted arylalkyl group (preferably optionally-substituted benzyl); an optionally-substituted heteroarylalkyl group, an optionally-substituted aryl (preferably an optionally-substituted phenyl), an optionally-substituted heteroaryl group, an optionally-substituted heterocyclic group or an alkoxyalkyl group having 1-12 carbon atoms and 1-4 oxygen atoms;

$L_1$ is a divalent linker having 1-12 carbon atoms, optionally 1-4 oxygen atoms, optionally one or two carbon-carbon double bonds, and hydrogens to satisfy valency (preferably $L_1$ has 1-12 —$CH_2$— groups and optionally 1-4 oxygen atoms);

each R independently is hydrogen or an alkyl group having 1-3 carbon atoms, with methyl being the preferred alkyl group; and $X_1$ and $X_2$ are independently selected from the group consisting of optionally-substituted straight-chain or branched alkyl groups having 3-8 carbon atoms, optionally-substituted cycloalkyl groups having 3-12 carbon atoms; optionally-substituted aryl; optionally-substituted heteroaryl groups, optionally-substituted heterocyclic groups; optionally-substituted cycloalkylalkyl groups, optionally-substituted arylalkyl groups, optionally-substituted heterocyclylalkyl groups and optionally-substituted heteroarylalkyl groups.

Substitution, when present includes, substitution with one or more non-hydrogen groups selected an from halogen, hydroxyl, alkyl having 1-3 carbon atoms, amino-substituted alkyl having 1-4 carbon atoms, alkoxy having 1-3 carbon atoms, amino, alkylamino having 1-3 carbon atoms, dialkyl amino where the alkyl group has 1-3 carbon atoms, aryl, haloalkyl having 1-3 carbon atoms, phenyl, benzyl, phenoxy, benzyloxy, oxo (=O), sulfhydryl, alkylthio having 1-3 carbon atoms, —$CO_2R'$ where R' is hydrogen or an alkyl having 1-3 carbon atoms, —COR', where R' is H or an alkyl having 1-3 carbon atoms, —CO—$NR'_2$, where each R' is independently hydrogen or alkyl having 1-3 carbon atoms, azido ($N_3$—), nitro, cyano, isocyano, thiocyano, or isothiocyano. Substitution of aryl or heteroaryl groups include substitution in which substituents on two ring atoms together with the ring atom or atoms to which they are attached form a 5-8 member ring which can contain 0 (carbocyclic) or 1-3 heteroatoms (particularly N, O or S). In a specific embodiment, substitution, if present, is substitution with one or more Cl, F, methyl, methoxy, or nitro groups.

Substitution of alkyl groups includes substitution with one or more optionally substituted aryl groups, or heteroaryl groups, where substitution of aryl groups, if present, includes substitution with one or more halogens, hydroxyls, alkyl groups, alkoxy groups, amino, alkylamino or dialkyl amino groups. Substitution of cycloalkyl groups includes substitution with one or more one or more halogens, hydroxyls, alkyl groups, aloxy groups, amino, alkylamino or dialkyl amino groups Specific arylalkyl groups are benzyl groups. Specific aryl groups are phenyl, bipheny and naphthyl groups. Specific substitution for such groups, if present, are one or more-halogens, alkyl groups having 1-3 carbon atoms, alkoxy having 1-3 carbon atoms, hydroxyl, and nitro groups.

In specific embodiments, substitution of a benzyl group can be 1-5 substituents on the phenyl ring of the group. In specific embodiments, substitution is 1, 2 or 3 substituents on the phenyl ring of the benzyl group. In specific embodiments, substitution is 1 substituents on the phenyl ring of the benzyl group, wherein the substituent is in the ortho, meta or para position with respect to the carbon carrying the —$CH_2$—. In specific embodiments, substitution is 1 substituent on the phenyl ring, wherein the substituent is in the para position with respect to the carbon carrying the —$CH_2$—. In specific embodiments, substitution is 1 substituent on the phenyl ring, wherein the substituent is in the meta position with respect to the carbon carrying the —$CH_2$—. Specific substituents for benzyl groups include halogens, alkyl groups having 1-3 carbon atoms, alkoxy groups having 1-3 carbon atoms, nitro groups, and hydroxyls. More specific substituents for benzyl groups are Cl, F, methyl, methoxy, hydroxyl and nitro groups. More specific substituents for benzyl groups are in the para or meta positions on the phenyl ring of the benzyl group.

In specific embodiments, substitution of a phenyl group can be 1-5 substituents on the phenyl ring. In specific embodiments, substitution is 1, 2 or 3 substituents on the phenyl ring. In specific embodiments, substitution is 1 substituents on the phenyl ring, wherein the substituent is in the ortho, meta or para position with respect to attachment of the phenyl group to the compound. In specific embodiments, substitution is 1 substituent on the phenyl ring, wherein the substituent is in the para position. In specific embodiments, substitution is 1 substituent on the phenyl ring, wherein the substituent is in the meta position. Specific substituents for phenyl groups include halogens, alkyl groups having 1-3 carbon atoms, alkoxy groups having 1-3 carbon atoms, nitro groups, and hydroxyls. More specific substituents for phenyl groups are Cl, F, methyl, methoxy, hydroxyl and nitro groups. More specific substituents for phenyl groups are in the para or meta positions on the phenyl ring of the benzyl group.

Specific cycloalkylalkyl groups are cycloalkylmethyl groups. More specific cycloalkylalkyl groups are cyclohexylmethyl and cyclopentyl methyl groups.

In specific embodiments, $X_1$ and $X_2$ are selected from optionally-substituted straight-chain or branched alkyl groups having 3-8 carbon atoms, optionally-substituted cycloalkylalkyl groups, optionally-substituted benzyl groups and optionally-substituted indolylalkyl groups. In specific embodiments, $X_1$ and $X_2$ are selected from unsubstituted straight-chain or branched alkyl groups having 3-8 carbon atoms. In specific embodiments, $X_1$ and $X_2$ are selected from substituted or unsubstituted benzyl groups. In specific embodiments, $X_1$ and $X_2$ are selected from substituted or unsubstituted benzyl groups or unsubstituted cyclohexylmethyl or unsubstituted cyclopentymethyl groups. In specific embodiments, $X_1$ and $X_2$ are selected from substituted benzyl groups or unsubstituted cyclohexylmethyl or unsubstituted cyclopentymethyl groups, wherein in an additional embodiment, benzyl substitution is with one or more halogens. In specific embodiments, $X_1$ and $X_2$ are selected from substituted benzyl groups or unsubstituted cyclohexylmethyl or unsubstituted cyclopentymethyl groups, wherein in an additional embodiment, benzyl substitution is with one or more Cl or F.

In specific embodiments, $X_1$ and $X_2$ are selected from optionally-substituted straight-chain or branched alkyl groups having 3-8 carbon atoms, and optionally-substituted benzyl groups. More specifically, $X_1$ and $X_2$ are selected from unsubstituted straight-chain or branched alkyl groups having 3-8 carbon atoms, and benzyl groups optionally substituted with 1 or 2 hydroxyl group or halide.

In specific embodiments, $X_1$ and $X_2$ are independently selected from sec-butyl, isobutyl, benzyl, p-OH-benzyl and 3-indolylmethyl:

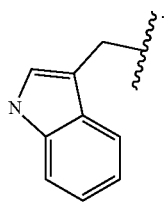

In specific embodiments, one of $X_1$ or $X_2$ is sec-butyl, isobutyl, unsubstituted benzyl, p-OH-benzyl or 3-indolylmethyl.

In specific embodiments, $X_1$ or $X_2$ are independently selected from sec-butyl, isobutyl, or unsubstituted benzyl.

In specific embodiments, $X_1$ or $X_2$ are independently selected from unsubstituted benzyl, p-OH-benzyl or 3-indolylmethyl.

In specific embodiments, $X_1$ or $X_2$ are independently selected from unsubstituted benzyl, or p-OH-benzyl.

In specific embodiments, $X_1$ or $X_2$ are independently selected from unsubstituted benzyl, or p-halo-benzyl.

In specific embodiments, $X_1$ or $X_2$ are independently selected from unsubstituted benzyl, or m-halo-benzyl.

In specific embodiments, both of $X_1$ and $X_2$ are unsubstituted benzyl. In specific embodiments, both of $X_1$ and $X_2$ are substituted benzyl. In specific embodiments, one of $X_1$ and $X_2$ is unsubstituted or substituted benzyl and the other is unsubstituted cyclohexylmethyl or cyclopentylmethyl. In specific embodiments, one of $X_1$ and $X_2$ is substituted benzyl and the other is unsubstituted cyclohexylmethyl or cyclopentylmethyl. In specific embodiments, one of $X_1$ and $X_2$ is halogen-substituted benzyl and the other is unsubstituted cyclohexylmethyl or cyclopentylmethyl. In specific embodiments, $X_1$ is unsubstituted or substituted benzyl and $X_2$ is unsubstituted or substituted benzyl, unsubstituted cyclohexylmethyl or cyclopentylmethyl.

In specific embodiments, Z is —NHC(O)CH$_3$. In specific embodiments, $R_2$ is an unsubstituted alkyl group having 1-4 carbon atoms. In specific embodiments, $R_2$ is an unsubstituted alkyl group having 1-3 carbon atoms. In specific embodiments, $R_2$ is an alkoxyalkyl group. In specific embodiments, $R_2$ is —(CH$_2$—O—CH$_2$)$_p$—CH$_3$, where p is 1-4. In specific embodiments, $R_2$ is —(CH$_2$—O—CH$_2$)$_p$—CH$_3$, where p is 1-2. In specific embodiments, $R_2$ is —(CH$_2$—O—CH$_2$)—CH$_3$. In specific embodiments, $R_2$ is —(CH$_2$—O—CH$_2$)$_2$—CH$_3$. In specific embodiments, $R_2$ is —(CH$_2$—O—CH$_2$)$_3$—CH$_3$. In specific embodiments, $R_2$ is —(CH$_2$—O—CH$_2$)$_4$—CH$_3$.

Exemplary $R_2$ groups include: an alkyl having 1-6 carbon atoms; or an alkyl having 1-4 carbon atoms; or an alkyl having 1-3 carbon atoms; or a methyl group; or an alkoxyalkyl group; or a —(CH$_2$—O—CH$_2$)v-CH$_3$ group, where v is 1-4; or a —(CH$_2$—O—CH$_2$)v-CH$_3$ group, where v is 1-2.

Exemplary $L_1$ groups include:
—(CH$_2$)$_n$—, where n is 1-9 inclusive, 1-8 inclusive, 1-7 inclusive, 1-6 inclusive or 1-5 inclusive;
—(CH$_2$)$_n$—, where n is 1-9 and 1, 2 or 3 non-adjacent —CH$_2$— groups are replaced with —O— atoms;
—(CH$_2$—CH$_2$)q-, where q is 2-5 inclusive, wherein one or two —CH$_2$—CH$_2$— moieties are replaced with a carbon-carbon double bond (—CH=CH—). In specific embodiments, the one or two carbon-carbon double bonds are cis-double bonds. In specific embodiments, the one or two carbon-carbon double bonds are trans-double bonds.

More specifically, $L_1$ groups include: —CH$_2$—O—CH$_2$—CH$_2$—O—CH$_2$—CH$_2$—O—CH$_2$—, —CH$_2$—O—CH$_2$—CH$_2$—CH$_2$—O—CH$_2$—CH$_2$—CH$_2$—; —CH$_2$—CH$_2$—O—CH$_2$—CH$_2$—O—CH$_2$—, or —CH$_2$—CH$_2$—O—CH$_2$—CH$_2$—O—CH$_2$—CH$_2$—.

In specific embodiments, W is —S—. In specific embodiments, W is —NH—. In specific embodiments, W is —NCH$_3$—. In specific embodiments, when W is —NH— or —NCH$_3$—, $L_1$ is —(CH$_2$)$_n$—, where n is 1-9 and more specifically n is 5, n is 6, n is 7, n is 8 or n is 9. In specific embodiments, when W is —NH— or —NCH$_3$—, $L_1$ is —(CH$_2$)$_7$.

In specific embodiments, all of the amino acid groups in Formula I are in the L-configuration. In specific embodiments, one of the amino acids of formula I is in the R-configuration. In specific embodiments, one of the amino acids of formula I is in the L-configuration.

In specific embodiments, the compound of Formula I is racemic. In specific embodiments, the compound of Formula I is substantially enantiomerically pure. In specific embodiments, the compound of Formula I is enantiomerically pure.

Compounds of the invention include those of Formula II:

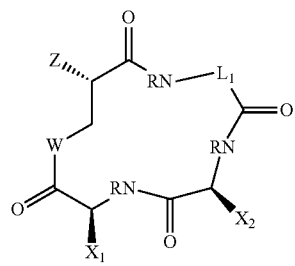

where variables are as defined for formula I and where any preferences for variables are also applied to Formula II.

In specific embodiments of Formulas I and II,
W is S, $L_1$ is —(CH$_2$)$_n$—, where n is 2-9 or 3-8, and all R are H;

W is S, $L_1$ is —$(CH_2)_n$—, where n is 2-9 or 3-8, and at least one of the R's are $CH_3$;

W is S, $L_1$ is —$(CH_2)_n$—, where n is 2-9 or 3-8, at least one of the R's are $CH_3$ and $X_1$ and $X_2$ are selected from sec-butyl, isobutyl, benzyl, p-OH-benzyl or 3-indolylmethyl;

W is S, $L_1$ is an alkoxyalkylene having 2-8 carbons and 1-3 oxygens, and all R are H;

W is S, $L_1$ is an alkoxyalkylene having 2-8 carbons and 1-3 oxygens, and at least one of the R's are $CH_3$;

W is S, $L_1$ is an alkoxyalkylene having 2-8 carbons and 1-3 oxygens, and at least one of the R's are $CH_3$ and $X_1$ and $X_2$ are selected from sec-butyl, isobutyl, benzyl, p-OH-benzyl or 3-indolylmethyl;

W is NH, $L_1$ is —$(CH_2)_n$—, where n is 2-9 or 3-8, and all R are H;

W is NH, $L_1$ is —$(CH_2)_n$—, where n is 2-9 or 3-8, and at least one of the R's are $CH_3$;

W is NH, $L_1$ is —$(CH_2)_n$—, where n is 2-9 or 3-8, at least one of the R's are $CH_3$ and $X_1$ and $X_2$ are selected from sec-butyl, isobutyl, benzyl, p-OH-benzyl or 3-indolylmethyl;

W is NH, $L_1$ is an alkoxyalkylene having 2-8 carbons and 1-3 oxygens, and all R are H;

W is NH, $L_1$ is an alkoxyalkylene having 2-8 carbons and 1-3 oxygens, and at least one of the R's are $CH_3$;

W is NH, $L_1$ is an alkoxyalkylene having 2-8 carbons and 1-3 oxygens, and at least one of the R's are $CH_3$ and $X_1$ and $X_2$ are selected from sec-butyl, isobutyl, benzyl, p-OH-benzyl or 3-indolylmethyl;

W is —N—$CH_3$, $L_1$ is —$(CH_2)_n$—, where n is 2-9 or 3-8, and all R are H;

W is —N—$CH_3$, $L_1$ is —$(CH_2)_n$—, where n is 2-9 or 3-8, and at least one of the R's are $CH_3$;

W is —N—$CH_3$, $L_1$ is —$(CH_2)_n$—, where n is 2-9 or 3-8, at least one of the R's are $CH_3$ and $X_1$ and $X_2$ are selected from sec-butyl, isobutyl, benzyl, p-OH-benzyl or 3-indolylmethyl;

W is —N—$CH_3$, $L_1$ is an alkoxyalkylene having 2-8 carbons and 1-3 oxygens, and all R are H;

W is —N—$CH_3$, $L_1$ is an alkoxyalkylene having 2-8 carbons and 1-3 oxygens, and at least one of the R's are $CH_3$; or W is —N—$CH_3$, $L_1$ is an alkoxyalkylene having 2-8 carbons and 1-3 oxygens, and at least one of the R's are $CH_3$ and $X_1$ and $X_2$ are selected from sec-butyl, isobutyl, benzyl, p-OH-benzyl or 3-indolylmethyl.

In additional specific embodiments of Formulas I and II,

—W—CO— is —CH═CH—, $L_1$ is —$(CH_2)_n$—, where n is 2-9 or 3-8, and all R are H;

—W—CO— is —CH═CH—, $L_1$ is —$(CH_2)_n$—, where n is 2-9 or 3-8, and at least one of the R's are $CH_3$;

—W—CO— is —CH═CH—, $L_1$ is —$(CH_2)_n$—, where n is 2-9 or 3-8, at least one of the R's are $CH_3$ and $X_1$ and $X_2$ are selected from sec-butyl, isobutyl, benzyl, p-OH-benzyl or 3-indolylmethyl;

—W—CO— is —CH═CH—, $L_1$ is an alkoxyalkylene having 2-8 carbons and 1-3 oxygens, and all R are H;

—W—CO— is —CH═CH—, $L_1$ is an alkoxyalkylene having 2-8 carbons and 1-3 oxygens, and at least one of the R's are $CH_3$; or —W—CO— is —CH═CH—, $L_1$ is an alkoxyalkylene having 2-8 carbons and 1-3 oxygens, and at least one of the R's are $CH_3$ and $X_1$ and $X_2$ are selected from sec-butyl, isobutyl, benzyl, p-OH-benzyl or 3-indolylmethyl.

In additional specific embodiments of Formulas I or II:

$X_1$ and $X_2$ are selected from sec-butyl, isobutyl, benzyl, 4-Cl-benzyl, 4-F-benzyl, 3-Cl-benzyl, 3-F-benzyl, cyclohexylmethyl and cyclopentylmethyl;

$X_1$ is selected from benzyl, 4-Cl-benzyl, 4-F-benzyl, 3-Cl-benzyl, and 3-F-benzyl and $X_2$ is selected from sec-butyl, isobutyl, benzyl, cyclohexylmethyl and cyclopentylmethyl;

$X_1$ is selected from benzyl, 4-Cl-benzyl, 4-F-benzyl, 3-Cl-benzyl, and 3-F-benzyl and $X_2$ is selected from sec-butyl, isobutyl, cyclohexylmethyl and cyclopentylmethyl;

$X_1$ is selected from benzyl, 4-Cl-benzyl, 4-F-benzyl, 3-Cl-benzyl, and 3-F-benzyl and $X_2$ is selected from cyclohexylmethyl and cyclopentylmethyl;

$X_1$ is selected from 4-Cl-benzyl, 4-F-benzyl, 3-Cl-benzyl, and 3-F-benzyl and $X_2$ is selected from cyclohexylmethyl and cyclopentylmethyl;

$L_1$ is —$(CH_2)_n$—, where n is 6-9, and $X_1$ and $X_2$ are selected from sec-butyl, isobutyl, benzyl, 4-Cl-benzyl, 4-F-benzyl, 3-Cl-benzyl, 3-F-benzyl, cyclohexylmethyl and cyclopentylmethyl;

$L_1$ is —$(CH_2)_n$—, where n is 6-9, and $X_1$ is selected from benzyl, 4-Cl-benzyl, 4-F-benzyl, 3-Cl-benzyl, and 3-F-benzyl and $X_2$ is selected from sec-butyl, isobutyl, benzyl, cyclohexylmethyl and cyclopentylmethyl;

$L_1$ is —$(CH_2)_n$—, where n is 6-9, and $X_1$ is selected from benzyl, 4-Cl-benzyl, 4-F-benzyl, 3-Cl-benzyl, and 3-F-benzyl and $X_2$ is selected from sec-butyl, isobutyl, cyclohexylmethyl and cyclopentylmethyl;

$L_1$ is —$(CH_2)_n$—, where n is 6-9, and $X_1$ is selected from benzyl, 4-Cl-benzyl, 4-F-benzyl, 3-Cl-benzyl, and 3-F-benzyl and $X_2$ is selected from cyclohexylmethyl and cyclopentylmethyl;

$L_1$ is —$(CH_2)_n$—, where n is 6-9, and $X_1$ is selected from 4-Cl-benzyl, 4-F-benzyl, 3-Cl-benzyl, and 3-F-benzyl and $X_2$ is selected from cyclohexylmethyl and cyclopentylmethyl;

$L_1$ is —$(CH_2)_7$— and $X_1$ and $X_2$ are selected from sec-butyl, isobutyl, benzyl, 4-Cl-benzyl, 4-F-benzyl, 3-Cl-benzyl, 3-F-benzyl, cyclohexylmethyl and cyclopentylmethyl;

$L_1$ is —$(CH_2)_7$—, and $X_1$ is selected from benzyl, 4-Cl-benzyl, 4-F-benzyl, 3-Cl-benzyl, and 3-F-benzyl and $X_2$ is selected from sec-butyl, isobutyl, benzyl, cyclohexylmethyl and cyclopentylmethyl;

$L_1$ is —$(CH_2)_7$—, and $X_1$ is selected from benzyl, 4-Cl-benzyl, 4-F-benzyl, 3-Cl-benzyl, and 3-F-benzyl and $X_2$ is selected from sec-butyl, isobutyl, cyclohexylmethyl and cyclopentylmethyl;

$L_1$ is —$(CH_2)_7$—, and $X_1$ is selected from benzyl, 4-Cl-benzyl, 4-F-benzyl, 3-Cl-benzyl, and 3-F-benzyl and $X_2$ is selected from cyclohexylmethyl and cyclopentylmethyl;

$L_1$ is —$(CH_2)_7$—, and $X_1$ is selected from 4-Cl-benzyl, 4-F-benzyl, 3-Cl-benzyl, and 3-F-benzyl and $X_2$ is selected from cyclohexylmethyl and cyclopentylmethyl;

$L_1$ is —$(CH_2)_r$—O—$(CH_2)_s$—O—$(CH_2)$t-, where r, s and t are independently 1-3 or r is 1-3, s is 2 or 3 and t is 1-3, and $X_1$ and $X_2$ are selected from sec-butyl, isobutyl, benzyl, 4-Cl-benzyl, 4-F-benzyl, 3-Cl-benzyl, 3-F-benzyl, cyclohexylmethyl and cyclopentylmethyl;

$L_1$ is —$(CH_2)_r$—O—$(CH_2)_s$—O—$(CH_2)$t-, where r, s and t are independently 1-3 or r is 1-3, s is 2 or 3 and t is 1-3, and $X_1$ is selected from benzyl, 4-Cl-benzyl, 4-F-benzyl, 3-Cl-benzyl, and 3-F-benzyl and $X_2$ is selected from sec-butyl, isobutyl, benzyl, cyclohexylmethyl and cyclopentylmethyl;

$L_1$ is —$(CH_2)_r$—O—$(CH_2)_s$—O—$(CH_2)$t-, where r, s and t are independently 1-3 or r is 1-3, s is 2 or 3 and t is 1-3, and $X_1$ is selected from benzyl, 4-Cl-benzyl, 4-F-benzyl, 3-Cl-benzyl, and 3-F-benzyl and $X_2$ is selected from sec-butyl, isobutyl, cyclohexylmethyl and cyclopentylmethyl;

$L_1$ is —$(CH_2)_r$—O—$(CH_2)_s$—O—$(CH_2)_t$-, where r, s and t are independently 1-3 or r is 1-3, s is 2 or 3 and t is 1-3, and $X_1$ is selected from benzyl, 4-Cl-benzyl, 4-F-benzyl, 3-Cl-benzyl, and 3-F-benzyl and $X_2$ is selected from cyclohexylmethyl and cyclopentylmethyl;

$L_1$ is —$(CH_2)_r$—O—$(CH_2)_s$—O—$(CH_2)_t$-, where r, s and t are independently 1-3 or r is 1-3, s is 2 or 3 and t is 1-3, and $X_1$ is selected from 4-Cl-benzyl, 4-F-benzyl, 3-Cl-benzyl, and 3-F-benzyl and $X_2$ is selected from cyclohexylmethyl and cyclopentylmethyl;

$L_1$ is —$(CH_2)_2$—O—$(CH_2)_2$—O—$(CH_2)_2$—, and $X_1$ and $X_2$ are selected from sec-butyl, isobutyl, benzyl, 4-Cl-benzyl, 4-F-benzyl, 3-Cl-benzyl, 3-F-benzyl, cyclohexylmethyl and cyclopentylmethyl;

$L_1$ is —$(CH_2)_2$—O—$(CH_2)_2$—O—$(CH_2)_2$—, and $X_1$ is selected from benzyl, 4-Cl-benzyl, 4-F-benzyl, 3-Cl-benzyl, and 3-F-benzyl and $X_2$ is selected from sec-butyl, isobutyl, benzyl, cyclohexylmethyl and cyclopentylmethyl;

$L_1$ is —$(CH_2)_2$—O—$(CH_2)_2$—O—$(CH_2)_2$—, and $X_1$ is selected from benzyl, 4-Cl-benzyl, 4-F-benzyl, 3-Cl-benzyl, and 3-F-benzyl and $X_2$ is selected from sec-butyl, isobutyl, cyclohexylmethyl and cyclopentylmethyl;

$L_1$ is —$(CH_2)_2$—O—$(CH_2)_2$—O—$(CH_2)_2$—, and $X_1$ is selected from benzyl, 4-Cl-benzyl, 4-F-benzyl, 3-Cl-benzyl, and 3-F-benzyl and $X_2$ is selected from cyclohexylmethyl and cyclopentylmethyl; or $L_1$ is —$(CH_2)_2$—O—$(CH_2)_2$—O—$(CH_2)_2$—, and $X_1$ is selected from 4-Cl-benzyl, 4-F-benzyl, 3-Cl-benzyl, and 3-F-benzyl and $X_2$ is selected from cyclohexylmethyl and cyclopentylmethyl.

In additional embodiments of the forgoing embodiments:
All R are hydrogens;
At least one R is methyl and the remaining R are hydrogen; or
All R are methyl.

In additional embodiments of the forgoing embodiments;
$R_2$ is an alkyl having 1-6 carbon atoms;
$R_2$ is an alkyl having 1-4 carbon atoms;
$R_2$ is an alkyl having 1-3 carbon atoms;
$R_2$ is a methyl group;
$R_2$ is an alkoxyalkyl group;
$R_2$ is a —$(CH_2$—O—$CH_2)v$-$CH_3$ group, where v is 1-4; or
$R_2$ is a —$(CH_2$—O—$CH_2)v$-$CH_3$ group, where v is 1-2;

In more specific embodiments, compounds of the invention are those of Formula III:

[Chemical structure of Formula III]

or salts or solvates thereof,
where:
W is W is S or $NR_1$, or —W—CO— is a carbon-carbon double bond, where $R_1$ is hydrogen or an alkyl group having 1 to 3 carbon atoms, with methyl being the preferred alkyl group and wherein a trans double bond is the preferred double bond;

R is hydrogen or an alkyl having 1-3 carbon atoms, wherein the preferred alkyl is methyl;

$R_2$ is hydrogen, an optionally-substituted alkyl group having 1-12 carbon atoms (preferably 2-10 carbon atoms), an optionally-substituted cycloalkyl group having 3-12 carbon atoms; an optionally-substituted arylalkyl group an optionally-substituted heteroarylalkyl group, an optionally-substituted heterocycylalkyl, an optionally-substituted cycloalkyl-substituted alkyl group; an optionally-substituted aryl, an optionally-substituted heteroaryl group, an optionally-substituted heterocycyl group or an alkoxyalkyl group having 1-12 carbon atoms and 1-4 oxygen atoms;

X is —$CH_2$— or —O—; and $X_1$ and $X_2$ are independently selected from the group consisting of optionally-substituted cycloalkyl groups having 3-12 carbon atoms; optionally-substituted aryl, optionally-substituted heteroaryl, optionally-substituted heterocycyl, optionally-substituted cycloalkylalkyl; optionally-substituted arylalkyl, optionally-substituted heteroarylalkyl and optionally-substituted heterocycylalkyl groups.

More specifically, $R_2$ is an unsubstituted alkyl having 1-12 carbon atoms. More specifically, $R_2$ is an unsubstituted alkyl having 1-6 carbon atoms. More specifically, $R_2$ is an unsubstituted alkyl having 1-4 carbon atoms. More specifically, $R_2$ is an unsubstituted alkyl having 1-3 carbon atoms. More specifically, $R_2$ is a methyl group. More specifically $R_2$ is an alkoxyalkyl group.

More specifically R is H or a methyl group. In an embodiment, all R are hydrogen. In an embodiment at least one R is methyl.

In an embodiment, both X are —O—. In another embodiment, both X are —$CH_2$—.

More specifically, $X_1$ and $X_2$ are selected from optionally-substituted cycloalkylalkyl or optionally-substituted arylalkyl. More specifically, $X_1$ and $X_2$ are selected from optionally-substituted cycloalkylmethyl or optionally-substituted benzyl. More specifically, $X_1$ and $X_2$ are selected from optionally-substituted cyclohexylmethyl or optionally-substituted benzyl. More specifically, $X_1$ and $X_2$ are selected from optionally-substituted cyclopentylmethyl or optionally-substituted benzyl. More specifically, $X_1$ is selected from optionally-substituted benzyl and $X_2$ is selected from cycloalkylmethyl. More specifically, $X_1$ is selected from optionally-substituted benzyl and $X_2$ is selected from cyclohexylmethyl or cyclopentylmethyl. More specifically, $X_1$ is selected from benzyl or benzyl substituted at the para and/or meta positions with one or more halogens, methyl, methoxy, hydroxyl or nitro groups and $X_2$ is selected from cyclohexylmethyl or cyclopentylmethyl. More specifically, both $X_1$ and $X_2$ are selected from optionally-substituted benzyl. More specifically, both $X_1$ and $X_2$ are selected from optionally-substituted benzyl, where substitution, if present is substitution at the para and/or meta positions with one or more halogen, nitro, methyl, methoxy or hydroxyl groups. More specifically, both $X_1$ and $X_2$ are selected from optionally-substituted benzyl, where substitution, if present, is substitution at the para and/or meta positions with one halogen. More specifically, both $X_1$ and $X_2$ are selected from optionally-substituted benzyl, where substitution, if present, is substitution at the para and/or meta positions with one Cl or F.

In specific embodiments of Formula III, W is —S—.
In other embodiments of Formula III, W is —NH— or —N($CH_3$)—

In other embodiments of Formula III, —W—CO— is a carbon-carbon double bond. In other embodiments of Formula III, —W—CO— is a trans carbon-carbon double bond.

In more specific embodiments, compounds of the invention are those of Formula IV:

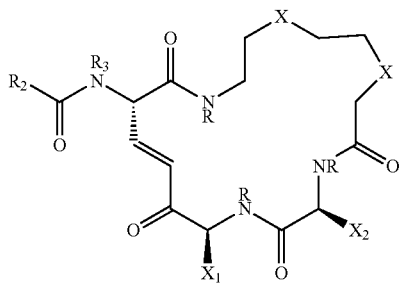

or salts or solvates thereof,
where:

R and $R_3$ are independently hydrogen or an alkyl having 1-3 carbon atoms, wherein the preferred alkyl is methyl;

$R_2$ is hydrogen, an optionally-substituted alkyl group having 1-12 carbon atoms (preferably 2-10 carbon atoms), an optionally-substituted cycloalkyl group having 3-12 carbon atoms; an optionally-substituted arylalkyl group an optionally-substituted heteroarylalkyl group, an optionally-substituted heterocycylalkyl, an optionally-substituted cycloalkyl-substituted alkyl group; an optionally-substituted aryl, an optionally-substituted heteroaryl group, an optionally-substituted heterocycyl group or an alkoxyalkyl group having 1-12 carbon atoms and 1-4 oxygen atoms;

X is —$CH_2$— or —O—; and $X_1$ and $X_2$ are independently selected from the group consisting of optionally-substituted cycloalkyl groups having 3-12 carbon atoms; optionally-substituted aryl, optionally-substituted heteroaryl, optionally-substituted heterocycyl, optionally-substituted cycloalkylalkyl; optionally-substituted arylalkyl, optionally-substituted heteroarylalkyl and optionally-substituted heterocycylalkyl groups.

More specifically, $R_2$ is an unsubstituted alkyl having 1-12 carbon atoms. More specifically, $R_2$ is an unsubstituted alkyl having 1-6 carbon atoms. More specifically, $R_2$ is an unsubstituted alkyl having 1-4 carbon atoms. More specifically, $R_2$ is an unsubstituted alkyl having 1-3 carbon atoms. More specifically, $R_2$ is a methyl group. More specifically $R_2$ is an alkoxyalkyl group.

More specifically R is H or a methyl group. In an embodiment, all R are hydrogen. In an embodiment at least one R is methyl. More specifically $R_3$ is H or a methyl group. In an embodiment, $R_3$ is hydrogen. In an embodiment at least one of R and $R_3$ is methyl.

In an embodiment, both X are —O—. In another embodiment, both X are —$CH_2$—.

More specifically, $X_1$ and $X_2$ are selected from optionally-substituted cycloalkylalkyl or optionally-substituted arylalkyl. More specifically, $X_1$ and $X_2$ are selected from optionally-substituted cycloalkylmethyl or optionally-substituted benzyl. More specifically, $X_1$ and $X_2$ are selected from optionally-substituted cyclohexylmethyl or optionally-substituted benzyl. More specifically, $X_1$ and $X_2$ are selected from optionally-substituted cyclopentylmethyl or optionally-substituted benzyl. More specifically, $X_1$ is selected from optionally-substituted benzyl and $X_2$ is selected from cycloalkylmethyl. More specifically, $X_1$ is selected from optionally-substituted benzyl and $X_2$ is selected from cyclohexylmethyl or cyclopentylmethyl. More specifically, $X_1$ is selected from benzyl or benzyl substituted at the para and/or meta positions with one or more halogens, methyl, methoxy, hydroxyl or nitro groups and $X_2$ is selected from cyclohexylmethyl or cyclopentylmethyl. More specifically, both $X_1$ and $X_2$ are selected from optionally-substituted benzyl. More specifically, both $X_1$ and $X_2$ are selected from optionally-substituted benzyl, where substitution, if present is substitution at the para and/or meta positions with one or more halogen, nitro, methyl, methoxy or hydroxyl groups. More specifically, both $X_1$ and $X_2$ are selected from optionally-substituted benzyl, where substitution, if present, is substitution at the para and/or meta positions with one halogen. More specifically, both $X_1$ and $X_2$ are selected from optionally-substituted benzyl, where substitution, if present, is substitution at the para and/or meta positions with one Cl or F.

In a second aspect, the invention provides dimers of Formula V:

$(AIP)_1$-$L_2$-$(AIP)_2$ or salts or solvates thereof,
where $(AIP)_1$ and $(AIP)_2$ are independently any one of the compounds of Formula I, II or III herein, and $L_2$ is a divalent chemical linker which forms a covalent bond between $(AIP)_1$ and $(AIP)_2$.

Most generally $L_2$ is a divalent chemical moiety which contains 1-20 carbons atoms, and optionally contains 1-6 heteroatoms selected from oxygen, nitrogen or sulfur with hydrogens as needed to satisfy valency.

In an embodiment, $L_2$ contains 1-20 carbon atoms, optionally one or more —S—S-group, optionally one or more CO group, optionally one or more —N(R")— group, optionally one or more —CO—NH— group or —NH—CO— group, optionally one or more —CO—O— group or —O—CO— group, optionally one or more —N(R")CO—N(R")— group, or optionally one or more carbon-carbon double bonds, where each R" is hydrogen or an alkyl having 1-3 carbon atoms, where a preferred alky is methyl.

In an embodiment, the $L_2$ linker contains one or more spacer portions and chemical residues such as —CO—, —CO—NH—, —NH—CO—, —O—CO—, or —CO—O— and more specifically amide residues that result from bonding of the linker to groups in $(AIP)_1$ and $(AIP)_2$. The spacer portion(s) of the linker can be alkylene, alkoxyalkylene or alkenylene. In an embodiment, a spacer portion contains 1-12 carbon atoms, optionally 1-4 oxygen atoms and optionally 1 or 2 carbon-carbon double bonds.

In specific embodiments, $(AIP)_1$ and $(AIP)_2$ are chemically the same and the dimer is a symmetric dimer. In specific embodiments, $(AIP)_1$ and $(AIP)_2$ are chemically different and the dimer is an asymmetric dimer.

In an embodiment, $L_2$ is a divalent chemical moiety which contains 1-20 carbons atoms, and optionally contains 1-4 oxygen atoms, optionally 1-4 sulfur atoms, optionally one or more CO groups, optionally one or more —N(R")— groups, optionally one or more —CO—NH— groups, optionally one or more —N(R")CO—N(R")— groups, optionally one or more —NH—CO—NH—, optionally one or more —O—CO—O—, optionally one or more —NH—CO—O—, optionally one or more —$SO_2$—, or optionally one or more carbon-carbon double bonds, where each R" is hydrogen or an alkyl having 1-3 carbon atoms, where a preferred alky is methyl.

In a specific embodiment, the two AIPs are linked via a portion of the Z residues, which are described herein. For example, $L_2$ is —CO-$L_3$-CO— or -$L_3$-CO-attached between the nitrogens carrying variable $R_3$ of the AIP, where $L_3$ is a linker as defined for $L_1$ herein above. More specifically, $L_3$ is an alkylene, an alkoxyalkylene or an alkenylene. More specifically, $L_3$ is an alkylene having 2-12 carbon atoms, an alkoxyalkylene having 2-12 carbon atoms and 1-4 oxygen atoms or an alkenylene having 3-12 carbon atoms and in each case hydrogen atoms to satisfy valency.

In specific embodiments, $L_3$ can take any value described for $L_1$ herein. In specific embodiments, $L_3$ is an alkylene, and more specifically is —$(CH_2)_p$—, where p is 1-12 or p is 2-12 or p is 3-12 or p is 4, or p is 6 or p is 8 or p is 10 or p is 12. In specific embodiments, $L_3$ is an alkoxyalkenylene. More specifically, $L_3$ is —$(CH_2$—$O$—$CH_2)_w$—, where w is 1-6 and more preferably w is 3 or 4.

The invention provides dimers of Formula VI:

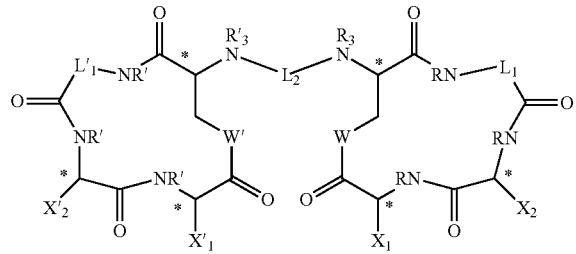

or salts or solvates thereof
where:
carbons indicated by * are independently in the L- or R-stereochemical form and the compound can be racemic, non-racemic or substantially enantiomerically pure;

R, $R_3$, $L_1$, $X_1$ and $X_2$ are as defined in Formulas I, II or III herein and all embodiments thereof and W', R', $R'_3$, $L'_1$, $X'_1$, and $X'_2$ take any of the values of the corresponding variables W, R, $R_3$, $L_1$, $X_1$, and $X_2$, respectively in Formula I, II or III herein and all embodiments thereof; and $L_2$ is a divalent linker.

In specific embodiments $L_2$ is selected from —$C_1$-$L_3$-$C_2$, where $L_3$ is a spacer which can be an alkylene, an alkoxyalkylene, or an alkyenelene and $C_1$ and $C_2$ are independently residues for forming a bond to the nitrogens carrying $R_3$ and $R'_3$.

In specific embodiments, $L_2$ is —CO-$L_3$-CO—.

More specifically $L_3$ can take any value described for $L_1$ herein. In specific embodiments, $L_3$ is an alkenylene, —$(CH_2)_p$—, where p is 2, 3, 4, 5, 6, 7 or 8. In specific embodiments, $L_3$ is an alkoxyalkenylene, —$(CH_2$—$O$—$CH_2$—$)_w$—, where p is 2, 3, 4, 5, 6, 7 or 8. In a specific embodiment, $L_3$ is —$(CH_2$—$O$—$CH_2$—$)_3$—, or —$(CH_2$—$O$—$CH_2$—$)_4$—.

In specific embodiments, $L_2$ is —CO-$L_3$-CO—, where $L_3$ is —$(CH_2$—$O$—$CH_2)_w$—, where w is 3 or 4 or $L_3$ is —$(CH_2)_z$—, where z is 1-12 or z is 2-12 or z is 2-8 or z is 2-6.

In specific embodiments, W', R', $R'_3$, $L'_1$, $X'_1$, and $X'_2$ take the same values as the corresponding variables W, R, $R_3$, $L_1$, $X_1$, and $X_2$, respectively and the dimer is a symmetric dimer. In specific embodiments, W', R', $R'_3$, $L'_1$, $X'_1$, and $X'_2$ take different values than the corresponding variables W, R, $R_3$, $L_1$, $X_1$, and $X_2$, respectively and the dimer is an asymmetric dimer.

Symmetric dimers and asymmetric dimers of Formulas V and VI function for modulation of quorum sensing. In an embodiment, a symmetric dimer of a compound which inhibits quorum sensing, inhibits quorum sensing. In an embodiment, an asymmetric dimer of two compounds of the invention each of which inhibit quorum sensing, inhibits quorum sensing. In an embodiment, a symmetric dimer of a compound which activates quorum sensing, activates quorum sensing. In an embodiment, an asymmetric dimer of two compounds of the invention each of which activate quorum sensing, activates quorum sensing.

In a specific embodiment, the invention provides a dimer comprising n5FF, n6FF, n7FF, n8FF, n9FF, n7OFF, n7FF amide, n8FF amide, n7OFF amide, n7OF3CLF, n7OF4clF, n7OF3fF, n7OChaF, n7Cha3fF or n7OCha3fF. More specifically the dimer is a symmetric dimer. More specifically the dimer is an asymmetric dimer. More specifically the dimer is a dimer of Formula V or a dimer of Formula VI.

The terms alkyl or alkyl group refer to a monoradical of a straight-chain or branched saturated hydrocarbon. Alkyl groups include straight-chain and branched alkyl groups. Unless otherwise indicated alkyl groups have 1-8 carbon atoms (C1-C8 alkyl groups) and preferred are those that contain 1-6 carbon atoms (C1-C6 alkyl groups) and more preferred are those that contain 1-3 carbon atoms (C1-C3 alkyl groups). Alkyl groups are optionally substituted with one or more non-hydrogen substituents as described herein. Exemplary alkyl groups include methyl, ethyl, n-propyl, iso-propyl, cyclopropyl, n-butyl, s-butyl, t-butyl, n-pentyl, various branched-pentyl, n-hexyl, various branched hexyl, all of which are optionally substituted, where substitution is define elsewhere herein. Substituted alkyl groups include fully halogenated or semihalogenated alkyl groups, such as alkyl groups having one or more hydrogens replaced with one or more fluorine atoms, chlorine atoms, bromine atoms and/or iodine atoms. Substituted alkyl groups include fully fluorinated or semifluorinated alkyl.

Cycloalkyl groups are alkyl groups having at least one 3- or more member carbon ring. Cycloalkyl groups include those having 3-20 carbon atoms and those having 3-12 carbon atoms. More specifically, cycloalkyl groups can have at least one 3-10-member carbon ring. Cycloalkyl groups can have a single carbon ring having 3-10 carbons in the ring. Cycloalkyl groups are optionally substituted. Cycloalkyl groups can be bicyclic having 6-12 carbons. Exemplary cycloalkyl groups include among others, cyclopropyl, cyclobutyl, cyclopentyl, cyclohexyl, cycloheptyl, cyclooctyl, cyclononyl and cyclodecyl groups. Bicyclic alkyl grouos include fused bicycici grouos and bridged bicyclic groups. Exemplary bicycloalkyl groups include, among others, bicyclo[2.2.2]octyl, bicyclo[4.4.0] decyl (decalinyl), and bicyclo[2.2.2]heptyl (norbornyl).

Cycloalkylalkyl groups are alkyl groups as described herein which are substituted with a cycloalkyl group as described herein. More specifically, the alkyl group is a methyl or an ethyl group and the cycloalkyl group is a cyclohexyl or a cylcopentyl group. Cycloalkyl groups are optionally substituted. In specific embodiments, optional substitution includes substitution with one or more halogens, alkyl groups having 1-3 carbon atoms, alkoxy groups having 1-3 carbo atoms, hydroxyl and nitro groups The term alkylene refers to a divalent radical of a straight-chain or branched saturated hydrocarbon. Alkylene groups can have 1-12 carbon atoms unless otherwise indicated. Alkylene groups include those having 2-12, 2-8, 2-6 or 2-4 carbon atoms. Linker groups ($L_1$) herein include alkylene groups, particularly straight chain, unsubstituted alkylene groups, —$(CH_2)_n$—, where n is 1-12, n is 1-10, n is 1-9, n is 1-8, n is 1-7, n is 1-6, n is 1-5, n is 1-4, n is 1-3, n is 2-10, n is 2-9, n is 2-8, n is 2-7, n is 2-6, n is 2-5 or n is 2-4.

An alkoxy group is an alkyl group, as broadly discussed above, linked to oxygen ($R_{alkyl}$—O—).

An alkenylene group is a divalent radical of a straight-chain or branched alkylene group which has one or more carbon-carbon double bonds. In specific embodiments, the same carbon atom is not part of two double bonds. In an alkenylene group one or more —CH$_2$—CH$_2$— moieties of the alkylene group are replaced with a carbon-carbon double bond. In specific embodiments, an alkenylene group contains 2-12 carbon atoms or more preferably 3-12 carbon atoms. In specific embodiments, an alkenylene group contains one or two double bonds. In specific embodiments, the alkenylene group contains one or two trans-double bonds. In specific embodiments, the alkenylene group contains one or two cis-double bonds. Exemplary alkenylene groups include: —(CH$_2$)$_n$—CH=CH—(CH$_2$)$_n$—, where n is 1-4 and more preferably is 2; and —(CH$_2$)$_n$—CH=CH—CH=CH—(CH$_2$)$_n$—, where n is 1-4 and more preferably is 1 or 2.

An alkoxyalkyl group is an alkyl group in which one or more of the non-adjacent internal —CH2- groups are replaced with —O—, such a group may also be termed an ether group. These groups may be straight-chain or branched, but straight-chain groups are preferred. Alkoxyalkyl groups include those having 2-12 carbon atoms and 1, 2, 3 or 4 oxygen atoms. More specifically, alkoxyalkyl groups include those having 3 or 4 carbons and 1 oxygen, or those having 4, 5 or 6 carbons and 2 oxygens. Each oxygen in the group is bonded to a carbon in the group. The group is bonded into a molecule via a bond to a carbon in the group.

An alkoxyalkylene group is a divalent alkoxyalkyl group. This group can be described as an alkylene group in which one or more of the internal —CH2- groups are replaced with an oxygen. These groups may be straight-chain or branched, but straight-chain groups are preferred. Alkoxyalkylene groups include those having 2-12 carbon atoms and 1, 2, 3 or 4 oxygen atoms. More specifically, alkoxyalkylene groups include those having 3 or 4 carbons and 1 oxygen, or those having 4, 5 or 6 carbons and 2 oxygens. Each oxygen in the group is bonded to a carbon in the group. The group is bonded into a molecule via bonds to a carbon in the group. Linker groups (L1) herein include alkoxyalkylene groups, particularly straight chain, unsubstituted alkoxyalkylene groups. Specific alkoxyalkylene groups include, among others, —CH$_2$—O—CH$_2$—, —CH$_2$—C$_{H2}$—O—CH$_2$—CH$_2$—, —CH$_2$—CH$_2$—CH$_2$—O—CH$_2$—CH$_2$—CH$_2$—, —CH$_2$—CH$_2$—O—CH$_2$—, —CH$_2$—O—CH$_2$—CH$_2$—, —CH$_2$—CH$_2$—O—CH$_2$—CH$_2$—O—CH$_2$—, —CH$_2$—CH$_2$—O—CH$_2$—CH$_2$—O—CH$_2$—CH$_2$—, —CH$_2$—CH$_2$—CH$_2$—O—CH$_2$—CH$_2$—CH$_2$—O—CH$_2$—, and —CH$_2$—CH$_2$—CH$_2$—O—CH$_2$—CH$_2$—CH$_2$—O—CH$_2$—CH$_2$—.

The term acyl group refers to the group —CO—R where R is hydrogen, an alkyl or aryl group as described herein.

Aryl groups include groups having one or more 5- or 6-member aromatic rings. Aryl groups can contain one, two or three, 6-member aromatic rings. Aryl groups can contain two or more fused aromatic rings. Aryl groups can contain two or three fused aromatic rings. Aryl groups are optionally substituted with one or more non-hydrogen substituents. Substituted aryl groups include among others those which are substituted with alkyl or alkenyl groups, which groups in turn can be optionally substituted. Specific aryl groups include phenyl groups, biphenyl groups, and naphthyl groups, all of which are optionally substituted as described herein. Substituted aryl groups include fully halogenated or semihalogenated aryl groups, such as aryl groups having one or more hydrogens replaced with one or more fluorine atoms, chlorine atoms, bromine atoms and/or iodine atoms. Substituted aryl groups include fully fluorinated or semifluorinated aryl groups, such as aryl groups having one or more hydrogens replaced with one or more fluorine atoms.

Alkyl groups include arylalkyl groups in which an alkyl group is substituted with an aryl group. Arylalkyl groups include benzyl and phenethyl groups among others. Arylalkyl groups are optionally substituted as described herein. Substituted arylalkyl groups include those in which the aryl group is substituted with 1-5 non-hydrogen substituents and particularly those substituted with 1, 2 or 3 non-hydrogen substituents. Useful substituents include among others, methyl, methoxy, hydroxy, halogen, and nitro. Particularly useful substituents are one or more halogens. Specific substituents include F. Cl, and nitro.

A heterocyclic group is a group having one or more saturated or unsaturated carbon rings and which contains one to three heteroatoms (e.g., N, O or S) per ring. These groups optionally contain one, two or three double bonds. To satisfy valence requirement, a ring atom may be substituted as described herein. One or more carbons in the heterocyclic ring can be —CO— groups. Heterocyclic groups include those having 3-12 carbon atoms, and 1-6, heteroatoms, wherein 1 or 2 carbon atoms are replaced with a —CO— group. Heterocyclic groups include those having 3-12 or 3-10 ring atoms of which up to three can be heteroatoms other than carbon. Heterocyclic groups can contain one or more rings each of which is saturated or unsaturated. Heterocyclic groups include bicyclic and tricyclic groups. Preferred heterocyclic groups have 5- or 6-member rings. Heterocyclic groups are optionally substituted as described herein. Specifically, heterocyclic groups can be substituted with one or more alkyl groups. Heterocyclic groups include those having 5- and 6-member rings with one or two nitrogens and one or two double bonds. Heterocyclic groups include those having 5- and 6-member rings with an oxygen or a sulfur and one or two double bonds. Heterocyclic group include those having 5- or 6-member rings and two different heteroatoms, e.g., N and O, O and S or N and S. Specific heterocyclic groups include among others among others, pyrrolidinyl, piperidyl, piperazinyl, pyrrolyl, pyrrolinyl, furyl, thienyl, morpholinyl, oxazolyl, oxazolinyl, oxazolidinyl, indolyl, triazoly, and triazinyl groups.

Heterocyylalky groups are alkyl groups substituted with one or more heterocycyl groups wherein the alkyl groups optionally carry additional substituents and the heterocycyl groups are optionally substituted. Specific groups are heterocycyl-substituted methyl or ethyl groups.

Heteroaryl groups include groups having one or more aromatic rings in which at least one ring contains a heteroatom (a non-carbon ring atom). Heteroaryl groups include those having one or two heteroaromatic rings carrying 1, 2 or 3 heteroatoms and optionally have one 6-member aromatic ring. Heteroaryl groups can contain 5-20, 5-12 or 5-10 ring atoms. Heteroaryl groups include those having one aromatic ring contains a heteroatom and one aromatic ring containing carbon ring atoms. Heteroaryl groups include those having one or more 5- or 6-member aromatic heteroaromatic rings and one or more 6-member carbon aromatic rings. Heteroaromatic rings can include one or more N, O, or S atoms in the ring. Heteroaromatic rings can include those with one, two or three N, those with one or two O, and those with one or two S, or combinations of one or two or three N, O or S. Specific heteroaryl groups include furyl, pyridinyl, pyrazinyl, pyrimidinyl, quinolinyl, purinyl, indolyl groups. In a specific embodiment, the heteroaryl group is an indolyl group and more specifically is an indol-3-yl group:

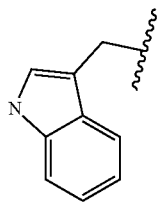

Heteroatoms include O, N, S, P or B. More specifically heteroatoms are N, O or S. In specific embodiments, one or more heteroatoms are substituted for carbons in aromatic or carbocyclic rings. To satisfy valence any heteroatoms in such aromatic or carbocyclic rings may be bonded to H or a substituent group, e.g., an alkyl group or other substituent.

Heteroarylalkyl groups are alkyl groups substituted with one or more heteroaryl groups wherein the alkyl groups optionally carry additional substituents and the aryl groups are optionally substituted. Specific alkyl groups are methyl and ethyl groups.

The term amino group refers to the species —N(H)$_2$. The term alkylamino refers to the species —NHR" where R" is an alkyl group, particularly an alkyl group having 1-3 carbon atoms. The term dialkylamino refers to the species —NR"$_2$ where each R" is independently an alkyl group, particularly an alkyl group having 1-3 carbon atoms.

Groups herein are optionally substituted most generally alky, cycloalkyl, aryl, heteroaryl and heterocyclic groups can be substituted with one or more halogen, hydroxyl group, nitro group, cyano group, isocyano group, oxo group, thioxo group, azide group, cyanate group, isocyanate group, acyl group, haloakyl group, alkyl group, alkenyl group or alkynyl group (particularly those having 1-4 carbons), a phenyl or benzyl group (including those that are halogen or alkyl substituted), alkoxy, alkylthio, or mercapto (HS—). In specific embodiments, optional substitution is substitution with 1-12 non-hydrogen substituents. In specific embodiments, optional substitution is substitution with 1-6 non-hydrogen substituents. In specific embodiments, optional substitution is substitution with 1-3 non-hydrogen substituents. In specific embodiments, optional substituents contain 6 or fewer carbon atoms. In specific embodiments, optional substitution is substitution by one or more halogen, hydroxy group, cyano group, oxo group, thioxo group, unsubstituted C1-C6 alkyl group or unsubstituted aryl group. The term oxo group and thioxo group refer to substitution of a carbon atom with a ═O or a ═S to form respectively —CO— (carbonyl) or —CS— (thiocarbonyl) groups.

Specific substituted alkyl groups include haloalkyl groups, particularly trihalomethyl groups and specifically trifluoromethyl groups. Specific substituted aryl groups include mono-, di-, tri, tetra- and pentahalo-substituted phenyl groups; mono-, di tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups.

More specifically, substituted aryl groups include acetyl-phenyl groups, particularly 4-acetylphenyl groups; fluoro-phenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups, and methoxyphenyl groups, particularly 4-methoxyphenyl groups.

As to any of the chemical groups herein that are substituted, i.e., contain one or more non-hydrogen substituents, it is understood, that such groups do not contain any substitution or substitution patterns which are sterically impractical and/or synthetically non-feasible. In addition, the compounds of this invention include all stereochemical isomers arising from the substitution of these compounds.

Compounds of the invention can be prepared by one of ordinary skill in the art in view of the descriptions provided herein and what is known in the art from commercially or otherwise readily available starting materials and reagents. As described herein in the Examples, known synthetic methods can be readily adapted for synthesis of the compounds of the formulas herein.

Well-known methods for assessment of drugability can be used to further assess active compounds of the invention for application to given therapeutic application. The term "drugability" relates to pharmaceutical properties of a prospective drug for administration, distribution, metabolism and excretion. Drugability is assessed in various ways in the art. For example, the "Lipinski Rule of 5" for determining drug-like characteristics in a molecule related to in vivo absorption and permeability can be applied (C. A. Lipinski, F. Lombardo, B. W. Dominy, P. J. Feeney, *Experimental and computational approaches to estimate solubility and permeability in drug discovery and development settings*, Adv. Drug Del. Rev., 2001, 46, 3-26 and Arup K. Ghose, Vellarkad N. Viswanadhan, and John J. Wendoloski, *A Knowledge-Based Approach in Designing Combinatorial or Medicinal Chemistry Libraries for Drug Discovery*, J. Combin. Chem., 1999, 1, 55-68.) In general a preferred drug for oral administration exhibits no more than one violation of the following rules:

(1) Not more than 5 hydrogen bond donors (e.g., nitrogen or oxygen atoms with one or more hydrogens);

(2) Not more than 10 hydrogen bond acceptors (e.g., nitrogen or oxygen atoms);

(3) Molecular weight under 500 g/mol and more preferably between 160 and 480; and (4) log P less than 5 and more preferably between −0.4 to +5.6 and yet more preferably −1<log P<2.

Compounds of this invention preferred for therapeutic application include those that do not violate one or more of 1-4 above.

Compounds of this invention preferred for therapeutic application include those having log P less than 5 and more preferably between −0.4 to +5.6 and yet more preferably −1<log P.

Compounds of the invention may contain chemical groups (acidic or basic groups) that can be in the form of salts. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts, alkaline earth metal salts such as calcium and magnesium salts, salts with organic bases (e.g., organic amines) such as benzathines, dicyclohexylamines, hydrabamines [formed with N,N-bis(dehydro-abietyl)ethylenediamine], N-methyl-D-glucamines, N-methyl-D-glucamides, t-butyl amines, and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Salt of the invention include "pharmaceutically acceptable salts" which refers to those salts which retain the biological effectiveness and properties of the free bases or free acids, and which are not biologically or otherwise undesirable. Pharmaceutically acceptable salts comprise pharmaceutically-acceptable anions and/or cations.

Compounds of the present invention, and salts thereof, may exist in their tautomeric form, in which hydrogen atoms are transposed to other parts of the molecules and the chemical bonds between the atoms of the molecules are consequently rearranged. It should be understood that all tautomeric forms, insofar as they may exist, are included within the invention. Additionally, inventive compounds may have trans and cis isomers and may contain one or more chiral centers, therefore exist in enantiomeric and diastereomeric forms. The invention includes all such isomers, as well as mixtures of cis and trans isomers, mixtures of diastereomers and racemic mixtures of enantiomers (optical isomers). When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. When enantiomeric or diastereomeric products are prepared, they can be separated by conventional methods, for example, by chromatographic or fractional crystallization. The inventive compounds may be in the free or hydrate form. The term enantiomerically pure refers to a sample containing molecules of a given structure whose molecules have the same chirality sense (i.e., are the same optical isomer) within the limits of detection. The term substantially enantiomerically pure refers to a sample containing molecules of a given structure, wherein equal to or less than 1% of the molecules of the sample have a different chirality sense. Compounds of the invention include those which are enatiomerically pure and those that are substantially enatiomerically pure.

With respect to the various compounds of the invention, the atoms therein may have various isotopic forms (e.g., isotopes of hydrogen include deuterium and tritium). All isotopic variants of compounds of the invention are included within the invention and particularly include deuterium and $^{13}$C isotopic variants. It will be appreciated that such isotopic variants may be useful for carrying out various chemical and biological analyses, investigations of reaction mechanisms and the like. Methods for making isotopic variants are known in the art.

The invention expressly includes pharmaceutically usable solvates of compounds according to formulas herein. Specifically useful solvates are hydrates. The compounds of formula I can be solvated (e.g., hydrated). The solvation can occur in the course of the manufacturing process or can take place (e.g., as a consequence of hygroscopic properties of an initially anhydrous compound of formulas herein (hydration)).

Compounds of the invention can have prodrug forms. Prodrugs of the compounds of the invention are useful in the methods of this invention. Any compound that will be converted in vivo to provide a biologically, pharmaceutically or therapeutically active form of a compound of the invention is a prodrug. Various examples and forms of prodrugs are well known in the art. Examples of prodrugs are found, inter alia, in Design of Prodrugs, edited by H. Bundgaard, (Elsevier, 1985), Methods in Enzymology, Vol. 42, at pp. 309-396, edited by K. Widder, et. al. (Academic Press, 1985); A Textbook of Drug Design and Development, edited by Krosgaard-Larsen and H. Bundgaard, Chapter 5, "Design and Application of Prodrugs," by H. Bundgaard, at pp. 113-191, 1991); H. Bundgaard, Advanced Drug Delivery Reviews, Vol. 8, p. 1-38 (1992); H. Bundgaard, et al., Journal of Pharmaceutical Sciences, Vol. 77, p. 285 (1988); and Nogrady (1985) Medicinal Chemistry A Biochemical Approach, Oxford University Press, New York, pages 388-392).

Pharmaceutically acceptable carriers are those carriers that are compatible with the other ingredients in the formulation and are biologically acceptable. Carriers can be solid or liquid. Solid carriers can include one or more substances that can also act as flavoring agents, lubricants, solubilizers, suspending agents, fillers, glidants, compression aids, binders, tablet-disintegrating agents, or encapsulating materials. Liquid carriers can be used in preparing solutions, suspensions, emulsions, syrups and elixirs. The active ingredient can be dissolved or suspended in a pharmaceutically acceptable liquid carrier such as water (of appropriate purity, e.g., pyrogen-free, sterile, etc.), an organic solvent, a mixture of both, or a pharmaceutically acceptable oil or fat. The liquid carrier can contain other suitable pharmaceutical additives such as, for example, solubilizers, emulsifiers, buffers, preservatives, sweeteners, flavoring agents, suspending agents, thickening agents, colors, viscosity regulators, stabilizers or osmo-regulators. Compositions for oral administration can be in either liquid or solid form.

Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins. Suitable examples of liquid carriers for oral and parenteral administration include water of appropriate purity, aqueous solutions (particularly containing additives, e.g. cellulose derivatives, sodium carboxymethyl cellulose solution), alcohols (including monohydric alcohols and polyhydric alcohols e.g. glycols) and their derivatives, and oils. For parenteral administration, the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant. Liquid pharmaceutical compositions that are sterile solutions or suspensions can be administered by, for example, intramuscular, intraperitoneal or subcutaneous injection. Sterile solutions can also be administered intravenously. Compositions for oral administration can be in either liquid or solid form. The carrier can also be in the form of creams and ointments, pastes, and gels. The creams and ointments can be viscous liquid or semisolid emulsions of either the oil-in-water or water-in-oil type. Pastes comprised of absorptive powders dispersed in petroleum or hydrophilic petroleum containing the active ingredient can also be suitable.

Staphylococcal infections, particularly *S. aureus* infections, can affect various parts of the body and can include skin infection and more serious conditions such as osteomyelitis, endocarditis, septic arthritis, and Toxic shock syndrome. *S. aureus* strains are considered the leading cause of nosocomial infections in the United States. Staphylococcal infections, particularly *S. aureus* infections, caused by a strain that is resistant to commonly used antibiotics are particularly serious and life-threatening. Of particular concern are strains that exhibit increased resistance to vancomycin. Compounds of the invention are useful in the treatment of such infections. Administration of one or more compounds of the invention can be combined with antibiotic regimens used for the treatment of staphylococcal infections. Various known antibiotics and various known antibiotic regimens can be employed in combination with one or more of the compounds of this invention. One of ordinary skill in the art can select form a variety of known antibiotics, which may be used alone or in combination, and which can specifically include, vancomycin, linezolid, and oxacillin. For example, one or more compounds of the invention can be used in combination with intravenous or oral antibiotics.

In another embodiment, the invention provides a medicament for treatment of an infectious disease, particularly a staphylococcal infection. The medicament comprises a therapeutically effective amount of one or more compounds of this invention as illustrated in one or more formulas herein which compounds exhibit antivirulence and/or antibacterial activity. In a specific embodiment, the medicament of this invention can also comprise a therapeutically effective amount of one or more antibiotics. The invention also provides a method for making this medicament that comprises combining a therapeutically effective amount of one or more compounds of this invention having anti-virulence activity with a selected pharmaceutical carrier appropriate for a given method of administration. In a specific embodiment, the method for making a medicament can additional include combining a therapeutically effective amount of one or more antibiotics in the medicament. The medicament may be an oral dosage form, an intravenous dosage form or any other art-recognized dosage form.

The present invention also provides methods of increasing or reducing the virulence of *Staphylococcus* species and specifically *Staphylococcus aureus*. In one aspect, the method comprises contacting a bacterium with an effective amount of a compound of the present invention. In another aspect, the method comprises contacting a bacterium with a therapeutically effective amount of a pharmaceutically acceptable salt of the compounds of the present invention. In yet another aspect, the method comprises contacting a bacterium with a precursor which can form an effective amount of a compound of the present invention.

Methods of this invention comprise the step of administering a "therapeutically effective amount" of the present therapeutic formulations containing the present compounds, to treat, reduce or regulate a disease state in a patient, including a disease state involving one or more infectious agents such as bacteria. The term "therapeutically effective amount," as used herein, refers to the amount of the therapeutic formulation, that, when administered to the individual is effective to treat, reduce, or regulate a disease state in a patient, including a disease state involving one or more infectious agents such as bacteria and more specifically *Staphylococcus*. As is understood in the art, the therapeutically effective amount of a given compound or formulation will depend at least in part upon, the mode of administration (e.g., intravenous, oral, topical administration), any carrier or vehicle employed, and the specific individual to whom the formulation is to be administered (age, weight, condition, sex, etc.). The dosage requirements need to achieve the "therapeutically effective amount" vary with the particular formulations employed, the route of administration, and clinical objectives. Based on the results obtained in standard pharmacological test procedures, projected daily dosages of active compound can be determined as is understood in the art.

Compounds of the invention are useful in therapeutic methods, particularly for treating infections. Any suitable form of administration can be employed in the method herein. The compounds of this invention can, for example, be administered in oral dosage forms including tablets, capsules, pills, powders, granules, elixirs, tinctures, suspensions, syrups and emulsions. Oral dosage forms may include sustained release or timed release formulations. The compounds of this invention may also be administered topically, intravenously, intraperitoneally, subcutaneously, or intramuscularly, all using dosage forms well known to those of ordinary skill in the pharmaceutical arts.

Compounds of this invention can also be administered in intranasal form by topical use of suitable intranasal vehicles. For intranasal or intrabronchial inhalation or insulation, the compounds of this invention may be formulated into an aqueous or partially aqueous solution, which can then be utilized in the form of an aerosol. Administration includes any form of administration that is known in the art and is intended to encompass administration in any appropriate dosage form and further is intended to encompass administration of a compound, alone or in a pharmaceutically acceptable carrier. Pharmaceutical carriers are selected as is known in the art based on the chosen route of administration and standard pharmaceutical practice.

The compounds of this invention can also be administered to the eye, preferably as a topical opthalmic formulation. The compounds of this invention can also be combined with a preservative and an appropriate vehicle such as mineral oil or liquid lanolin to provide an opthalmic ointment. The compounds of this invention may be administered rectally or vaginally in the form of a conventional suppository. The compounds of this invention may also be administered transdermally through the use of a transdermal patch containing the active compound and a carrier that is inert to the active compound, is non-toxic to the skin, and allows delivery of the agent for systemic absorption into the blood stream via the skin.

The compounds of the invention may be administered employing an occlusive device. A variety of occlusive devices can be used to release an ingredient into the blood stream such as a semipermeable membrane covering a reservoir containing the active ingredient with or without a carrier, or a matrix containing the active ingredient. Other occlusive devices are known in the literature.

Pharmaceutical compositions and medicaments of this invention comprise one or more compounds of the invention of formula I or II (or other formulas herein) in combination with a pharmaceutically acceptable carrier, excipient, or diluent. Such compositions and medicaments are prepared in accordance with acceptable pharmaceutical procedures, such as, for example, those described in Remingtons Pharmaceutical Sciences, 17th edition, ed. Alfonoso R. Gennaro, Mack Publishing Company, Easton, Pa. (1985), which is incorporated herein by reference in its entirety. The invention also encompasses method for making a medicament employing one or more compounds of this invention which exhibit a therapeutic effect.

In another aspect, the present invention provides pharmaceutical and therapeutic preparations comprising a therapeutically effective amount of one or more compounds of the present invention of Formula I optionally in combination with a pharmaceutically acceptable carrier. In particular, pharmaceutical and therapeutic preparations of this invention comprise an amount or combined amount of one or more compounds of this invention effective for bacterial interference, particularly of a *Staphylococcus* species and more particularly of *Staphylococcus aureus* and including a *Staphylococcus aureus* group I strain and more particularly a bacterial human or veterinary pathogen. Compounds useful in the methods of this invention include pharmaceutically-acceptable salts of the compounds of formulas herein. Compounds useful in the methods of this invention include pharmaceutically-acceptable prodrugs of the compounds of formulas herein. Salts include any salts derived from the acids of the formulas herein which are acceptable for use in human or veterinary applications. Bacterial interference includes attenuation of virulence.

In another aspect, the present invention provides a method of treating an infectious disease comprising administering to an individual in need of treatment, a composition comprising one or more compounds of the present invention. In an embodiment, the infectious disease relates to that associated with an infectious agent comprising a bacterium. In a specific embodiment, the bacteria are *Staphylococcus*. In a specific embodiment, the bacteria are one or more selected from the group consisting of *S. aureus* and *S. epidermidis*. In a specific embodiment, the bacteria are one or more drug resistant *Staphylococcus* strains. In a specific embodiment, the bacteria are one or more drug resistant *S. aureus* or *S. epidermidis* strains. Compounds of the invention can be employed in human treatment or in veterinary treatment.

An infectious disease may be associated with more than one infectious agent. In this regard, the compounds of the invention can be employed to treat such infectious diseases where one of the infectious agents is *Staphylococcus*, particularly *S. aureus*, or *S. epidermidis*, and more particularly such bacteria that are drug-resistant. The term drug-resistant as used herein refers in particular to bacteria which are resistant to currently employed antibiotics and includes bacteria which are resistant to one or more of such antibiotics (multidrug-resistant). Drug-resistance is a term that is understood in the art and is described, for example, in Magiorakos et al. (2012) "Multidrug-resistant, extensively drug-resistant and pandrug-resistant bacteria: an international expert proposal for interim standard definitions for acquired resistance," Clin Microbiol and Infect 18:268-281.

In an embodiment, the invention provides a pharmaceutical composition comprising one or more compounds of any one of Formulas I, II, III, IV, V or VI.

In an embodiment, the invention provides a pharmaceutical composition comprising one or more dimers of formulas V or VI.

In an embodiment, the invention provides a method for regulating virulence in *Staphylococcus* that comprises the step of contacting the bacterium with one or more compounds selected from the compounds of Formulas I, II, II, IV, V or VI.

In an embodiment, the invention provides a method for attenuating virulence in a strain of *Staphylococcus* that comprises the step of contacting the bacterium with one or more compounds selected from the compounds of Formulas I, II, II, IV, V or VI. Contacting includes contacting the bacterium or contacting an environment that contains the bacterium. The environment can be in vitro or in vivo.

In an embodiment, the invention provides a method for attenuating the production of toxic shock syndrome toxin-1 that comprises the step of contacting the bacterium or an environment containing the bacterium with one or more compounds selected from the compounds of Formulas I, II, II, IV, V or VI.

In an embodiment, the invention provides a method of treating staphylococcal infection which comprises administering to an individual in need of treatment a therapeutically effective amount of one or more compounds of Formulas I, II, II, IV, V or VI.

In an embodiment, the invention provides a method of treating staphylococcal infection of a strain of *S. aureus*, *S. epidermidis* or both which comprises administering to an individual in need of treatment a therapeutically effective amount of one or more compounds of Formulas I, II, II, IV, V or VI.

In an embodiment, the invention provides a medicament for use for treatment of a staphylococcal infection which medicament comprises one or more compounds of Formula I, II, III, IV, V, or VI. In a further embodiment, the invention provides a method of making a medicament for treatment of a staphylococcal infection which medicament comprises one or more compounds of Formula I, II, III, IV, V, or VI.

All references throughout this application, for example patent documents including issued or granted patents or equivalents; patent application publications; and non-patent literature documents or other source material; are hereby incorporated by reference herein in their entireties, as though individually incorporated by reference. All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (e.g., to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

When a group of substituents is disclosed herein, it is understood that all individual members of the group and all subgroups, including any isomers and enantiomers of the group members, and classes of compounds that can be formed using the substituents are disclosed separately. When a compound is claimed, it should be understood that compounds known in the art including the compounds disclosed in the references disclosed herein are not intended to be included. When a Markush group or other grouping is used herein, all individual members of the group and all combinations and subcombinations possible of the group are intended to be individually included in the invention.

Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination.

One of ordinary skill in the art will appreciate that methods, device elements, starting materials, and synthetic methods other than those specifically exemplified can be employed in the practice of the invention without resort to undue experimentation. All art-known functional equivalents, of any such methods, device elements, starting materials, and synthetic methods are intended to be included in this invention. Whenever a range is given in the specification, for example, a temperature range, a time range, or a composition range, all intermediate ranges and subranges, as well as all individual values included in the ranges given are intended to be included in the invention.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

Without wishing to be bound by any particular theory, there can be discussion herein of beliefs or understandings of underlying principles relating to the invention. It is recognized that regardless of the ultimate correctness of any mechanistic explanation or hypothesis, an embodiment of the invention can nonetheless be operative and useful.

The terms and expressions that have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention.

THE EXAMPLES

Example 1

Experimental Details can also be found in Vasquez et al. 2017 [34], which is incorporated by reference herein in its entirety for such detail.

Reagents, Instrumentation, and General Methods: All chemical reagents and solvents were purchased from commercial sources (Chem-Impex International and Sigma-Aldrich) and used without further purification, except for dichloromethane (DCM), which was distilled and dried over activated molecular sieves. Water (18 MΩ) was purified using a Thermo Scientific Barnstead Nanopure system. Solid-phase resin was purchased from NovaBiochem.

All standard biological reagents were purchased from Sigma-Aldrich and used according to enclosed instructions. Brain heart infusion (BHI) was purchased from Teknova and prepared as instructed with pH=7.35.

Reversed-phase high performance liquid chromatography (RP-HPLC) was performed using a Shimadzu system equipped with a SCL-10Avp system controller, a DGU-20A5 degasser, LC-20AT solvent delivery unit, a SIL-10AF autosampler, a CTO-20A column oven equipped with a manual injector, a SPD-M20A UV-Vis diode array detector, and a FRC-10A fraction collector. Solvent A was 18 MΩ water containing 0.1% trifluoroacetic acid (TFA), and Solvent B was HPLC grade acetonitrile (AcN) with 0.1% TFA. For purification, a semi-preparative Kromasil Eternity C18 column (10 mm×250 mm, 5 μm particle size with 100 Å pore size) was used with linear gradient of 38% solvent B→48% solvent B at 5 mL per min flow rate for 30 min. For analytical samples, an analytical Kromasil Eternity C18 column (4.6 mm×250 mm, 5 μm particle size with 100 Å pore size) was used to determine purity with a linear gradient of 10% solvent B→95% solvent B at 1 mL per min flow rate for 27 min. Peptide purities were assessed by integration of peaks detected at 220 nm.

MALDI-TOF mass spectrometry (MS) data were obtained on a Bruker RELEX II spectrometer equipped with a 337 nm laser and a reflectron. In positive ion mode, the acceleration voltage was 25 kV. Exact mass (EM) data were obtained on either a Waters (Micromass) LCT ESI-TOF mass spectrometer or a Thermo Q Exactive Plus™ ESI-Q-IT (orbitrap) mass spectrometer.

Nuclear magnetic resonance (NMR) spectroscopy experiments were performed at the National Magnetic Resonance Facility at Madison (NMRFAM) on a 750 MHz Bruker Avance-III instrument equipped with a TCI cryogenic probe.

Solid-Phase Peptide Synthesis (SPPS): The peptidomimetics were prepared on Dawson 3-(Fmoc-amino)-4-aminobenzoyl (Dbz) AM resin (100-200 mesh) using standard Fmoc SPPS methods as described by Chan and White. [16] All solid-phase reactions were mixed via agitation on a shaker table. Briefly, the resin (0.050 mmol eq.) was swelled in dichloromethane (DCM) for 30 min, and the solvent was exchanged for dimethylformamide (DMF). Piperidine (20% in DMF, 2 mL, 5 min×3) was used to effect standard Fmoc group deprotections. For each amino acid coupling, DMF (2 mL) containing the Fmoc-protected amino acid (0.2 mmol), N-[(dimethylamino)-1H-1,2,3-triazolo-[4,5-b]pyridin-1-yl-methylene]-N-methylmethanaminium hexafluorophosphate N-oxide (HATU, 0.2 mmol), and diisopropylethylamine (DIPEA, 0.4 mmol) were preactivated for 2.5 min, then added to the resin for 30 min. To acetylate the N-terminus, acetic anhydride (0.5 mmol) and DIPEA (0.35 mmol) were dissolved in DMF (2 mL) and added to the resin for 15 min. All couplings and deprotections were preceded by triple-washing with an appropriate solvent, and reaction completion was monitored via Kaiser test. To install the n7 oxo linker into n7FF, 8-(Fmoc-amino)-3,6-dioxaoctanoic acid was incorporated during SPPS. To install the amide linkages into n7FF amide, n8FF amide, and n7OFF amide, L-2,3-diaminopropionic acid (Dap) was incorporated instead of Cys during SPPS.

To activate the Dbz group prior to peptidomimetic cleavage, the resin was exchanged into DCM and treated twice with 4-nitrophenylchloroformate (0.25 mmol) in DCM (2.5 mL) for 30 min. The resin was then exchanged into DMF, and cyclic urea was formed by twice adding DIPEA (216 μL, 1.24 mmol) in DMF (2 mL) for 10 min. The resin was washed sequentially with DMF (2 mL×2), DCM (2 mL×2), and Et$_2$O (2 mL×2), dried under N$_2$, and reduced for 18 hr under vacuum. To cleave the linear peptidomimetic, the resin was treated with a cleavage cocktail of 36:2:1:1 TFA:DCM:H$_2$O:triisopropyl silane (3 mL) for 2 hr. The mixture was filtered into a round-bottom flask, and the resin was washed with cleavage cocktail (3 mL×2).

The collected solution was concentrated by rotary evaporation and precipitated in Et$_2$O at −20° C. overnight. The solid precipitate was dissolved in 1:1 AcN:H$_2$O, frozen using iPrOH/dry ice, and lyophilized. The lyophilized linear peptidomimetic was purified by semi-preparative RP-HPLC using the method outlined above. Collected fractions were analyzed using MALDI-MS to isolate the desired product, frozen using iPrOH/dry ice, and lyophilized.

Macrocyclization and Product Isolation: Macrocyclization of the linear peptidomimetics (to give thiolactones) was performed using our previously reported method, with some minor modifications.[4k] Cyclization buffer was prepared by dissolving guanidinium chloride (18.32 g, 192 mmol) to a final volume of 32 mL in 0.1 M Na$_2$HPO$_4$, adding AcN (8 mL), and adjusting pH to 6.8. The linear peptidomimetic was dissolved in 4 mL of cyclization buffer in a 15 mL conical tube and agitated on a shaker table at 50° C. for 2 hr. Macrocyclization of the linear peptidomimetics (to give amides) was performed using our previously reported method, with some minor modifications. [4l] The deprotected linear peptide was dissolved in anhydrous tetrahydrofuran (6 mL) with (7-azabenzotriazol-1-yloxy)tripyrrolidinophosphonium hexafluorophosphate (PyAOP, 2 eq.) and DIPEA (4 eq.). Reaction progress was monitored via RP-HPLC and reaction completion was observed within 6 hr. The macrocyclic peptidomimetics were then purified via RP-HPLC and their masses were checked by MALDI-MS.

To verify peptide identity, exact mass determinations were obtained for final products using ESI-MS (see Table S1, in the supporting information for Vasquez et al. 2017 [34]). Peptidomimetic purities were checked by analytical RP-HPLC using the methods described above. All samples displayed purities in excess of 90% by peak integration, with >95% purity for n7FF, n8FF, and n7OFF. Isolated peptidomimetics were stored as 1 mM stock solutions in DMSO at 4° C., with the exception of n7OFF which was stored as a 4 mM stock DMSO solution (used specifically for screening in group-IV *S. aureus*).

Reporter Gene Assays: The peptidomimetics were assayed for AgrC I-IV inhibition using the four YFP reporter strains listed in Table 1. Peptide stock solutions were diluted with DMSO in serial dilutions, and 2 µL of the diluted solution was added to each of the wells in a black, clear-bottom 96-well microtiter plate (Costar). An overnight culture of *S. aureus* YFP strain (Table 1) was diluted 1:50 with fresh BHI (pH 7.35). A 198 µL-portion of diluted culture was added to each well of the microtiter plate containing peptide (resulting in a 1% DMSO solution). Plates were incubated at 37° C. with shaking at 200 rpm for 24 h. Fluorescence (excitation 500 nm/emission 540 nm) and optical density at 600 nm (OD$_{600}$) of each well were then recorded using a BioTek Synergy 2 plate reader. IC$_{50}$ values and 95% confidence intervals were determined using GraphPad Prism 6 software with four parameter variable slope dose response curves. Full dose response curves are provided in Figures S3A-D, S4A-D, S5A-D, S6A-D and S7A-F.

TABLE 1

Bacterial reporter strains used for AgrC inhibition assays.

| bacterium | strain | parent strain |
|---|---|---|
| *S. aureus* group-I | AH1677[21] | USA300 LAC |
| *S. aureus* group-II | AH430[21, 22] | SA502A |
| *S. aureus* group-III | AH1747[21] | MW2 |
| *S. aureus* group-IV | AH1872[21] | MN EV |

NMR Experimental Protocols: NMR experiments on n7OFF and AIP-III D4A were conducted at ambient temperature in 95% H$_2$O/5% D$_2$O. The n7OFF sample was at a concentration ≥1.5 mM and a pH≈7. The *S. aureus* AIP-III D4A sample was at a concentration ≥700 µM and a pH≈6.5. Chemical shifts were referenced to H$_2$O at 4.7 ppm. Dilutions were prepared to check for differences in proton chemical shifts that would indicate aggregation issues; no such differences were observed.

Four standard NMR experiments were used. A proton NMR experiment was performed to check for lock and shim quality. A 1D proton NMR experiment with excitation sculpting (Bruker pulse sequence zgesgp) was performed to check signal to noise and aid in sequential assignments. Parameters included a sweep width of 6756.8 Hz (9 ppm), 4 s acquisition time, 3 s relaxation delay, 32 scans, 27026 real points, and full spectral size of 65536 points. A 2D TOCSY experiment (Bruker pulse sequence mlevesgpph) was used to identify the proton resonances associated with each amino acid residue. The spin-lock mixing time was set to 80 ms for n7OFF and 120 ms for AIP-III D4A. TOCSY parameters include sweep width of 6756.8 Hz (9 ppm), 3 s relaxation delay, 256 points in the indirect dimension, 1024 (n7OFF) or 2048 (AIP-III D4A) points in the direct dimension, and 2 scans. To obtain internuclear proton distances through dipolar couplings, 2D ROESY experiments were performed (Bruker pulse sequence roesyesgpph). The ROESY spin-lock mixing time was varied, with final experiments performed at 300 ms. Additional ROESY parameters included a sweep width of 6756.8 Hz (9 ppm), 3 s relaxation delay, 1024 points in the indirect dimension, 8192 points in the direct dimension, and 16 scans.

A $^1$H—$^{13}$C HSQC experiment (Bruker pulse sequence hsqcetgpsisp2.2) was used to differentiate the chemical shifts of several methylene protons in n7OFF. Parameters included a sweep width of 5252.1 (7 ppm) in the direct dimension and 31055.9 Hz (165 ppm) in the indirect dimension, spectrum center 3522.4 Hz (4.7 ppm) in the direct dimension and spectrum center 16979.5 Hz (90.0 ppm) in the indirect dimension, 2048 points in the direct dimension and 512 points in the indirect dimension, $^1$H—$^{13}$C coupling detection of 145 Hz, a 3 s relaxation delay, and 2 scans.

All NMR spectra were analyzed using MestReNova 10 NMR processing software. Resonance assignments were determined using standard sequential methodology as described previously.[23] The ROESY crosspeak volumes were integrated and integral values were entered in a spreadsheet. The values were calibrated to provide estimated distances for each crosspeak with a uniform±20% constraint allowance to account for spin diffusion. The obtained distances were formatted for constraint files compatible with the Xplor NIH software suite (v2.31).[19] Three-dimensional structure calculations and refinements made use of the torsion angle molecular dynamics and the internal variable dynamics modules [24] of Xplor-NIH, with patches for the thioester bridge and ring closure. [4h] The target function minimized was composed of the experimental NMR restraints (ROE-derived interproton distances and torsion angles), a repulsive van der Waals potential for the non-bonded contacts [25], a torsion angle database potential of mean force [26], and a gyration volume potential.[27]

NMR Spectra, Assignments, Constraint Summaries and Additional Images are provided in Vasquez et al. [34]. NMR spectra are provided therein for t-AIP-II, n7OFF, and AIP-III D4A. This reference lists chemical shift assignments for t-AIP-II and provides Xplor-NIH constraint summary for the t-AIP-II annealing experiments. Figure S8 in the supporting information for Vasquez et al. [34] provides the ensemble of 20 lowest energy structures for t-AIP-II from annealing with 20% allowance on constraints and shows the overlay of representative old and new t-AIP-II solution structures.

Vasquez et al. (SI) [34] also lists chemical shift assignments for n7OFF and AIP-III D4A, provides Xplor-NIH constraint summary for the n7OFF and AIP-III D4A annealing experiments and provides the ensemble of 20 lowest energy structures for n7OFF and AIP-III D4A from annealing with 20% allowance on constraints. This reference also shows the overlay of representative old and new AIP-III D4A solution structures and selected views of the overlaid structures of n7OFF and t-AIP-II, and n7OFF and AIP-III D4A. Vasquez et al. 2017 [34] is incorporated by reference herein for description therein of structural similarites and differences among mimetics, t-AIP-II and AIP-II D4A.

The structure RMSD determinations and image files were prepared using PyMOL.[28]

To produce the topology and parameter files for the non-natural n7O amino acid, the structure was inputted into PRODRG online server to create topology and parameter files, and the atoms in the output files were renamed to standard convention.[29] Ensembles of 20% lowest energy structures were averaged for each molecule, and a structure with a low RMS difference relative to the average and low relative energy was selected for each ensemble as a representative structure.

Example 2

Library Design and Synthesis

Figure 1B:
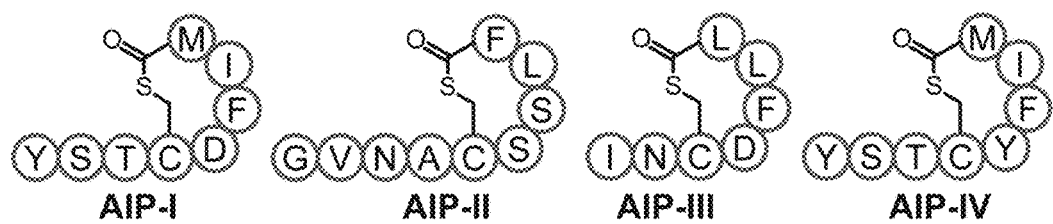

To develop a minimized AIP scaffold, truncated AIP t-AIP-II was selected as the model peptide due to its small size and concomitant high potency (i.e., $IC_{50}$ values for AgrC inhibition in the low nanomolar range for each S. aureus group).[5l] A differentiating feature of t-AIP-II (and its parent, AIP-II) is that it contains only two hydrophobic amino acids in the macrocycle (FIG. 2A), as opposed to the three present in the other AIPs (FIG. 1B). t-AIP-II, as determined by solution-phase NMR studies, adopts a rigid structure in solution with the Leu4 and Phe5 side chains pointing in the same direction and in close proximity to each other.[4k] This study, in conjunction with earlier mechanistic work [5n], suggests that the presence and close positioning of these hydrophobic residues is critical for AgrC binding. Hydrophobic functionality was thus retained at these two positions in this minimized AIP-II scaffold, and Leu, Phe, and Ile were systematically examined in each of these positions. Streamlining the scaffold thereafter, the two Ser residues (Ser2 and Ser3) were replaced by a single aliphatic linker. For peptidic AgrC ligands, the macrocycle has been shown to require a defined size for AgrC recognition (16-17 atoms) with restrictions on the positions that can accept an extra atom.[5p] Different aliphatic linker lengths, with a chain of methylenes varying between 1-7 carbons long (yielding macrocycles of 13-19 atoms), were examined. Cys1 was retained to create the thiolactone moiety that closes the macrocycle and is known to be important for recognition by AgrC.[5l, 5n] The modifications of t-AIP-II to create this new scaffold are summarized in FIG. 2A.

A library of peptidomimetics based on this simplified scaffold was prepared with every permutation of the desired hydrophobic residues and linker lengths (FIG. 2A), using standard Fmoc solid-phase peptide synthesis (SPPS) methods.[16] Macrocyclization was performed using our previously reported procedure [4g], followed by routine HPLC purification and MS characterization as described above. This minimized AIP-II scaffold remedied several shortcomings of fully peptidic ligands. Because the number of natural amino acids is minimized, there is less opportunity for enzymatic degradation, thus improving ligand stability. In addition, fewer coupling steps are required to produce these peptidomimetics, thereby shortening synthesis times and increasing overall product yields (~25% on average). The small size of these mimetics also opens up the possibility for larger scale production using solution-phase synthesis.

Vasquez et al. (2017) [34] is incorporated by reference herein for additional details of synthesis of compounds of compounds herein of Formulas I, II, III or IV.

Example 3

Figure 2A:
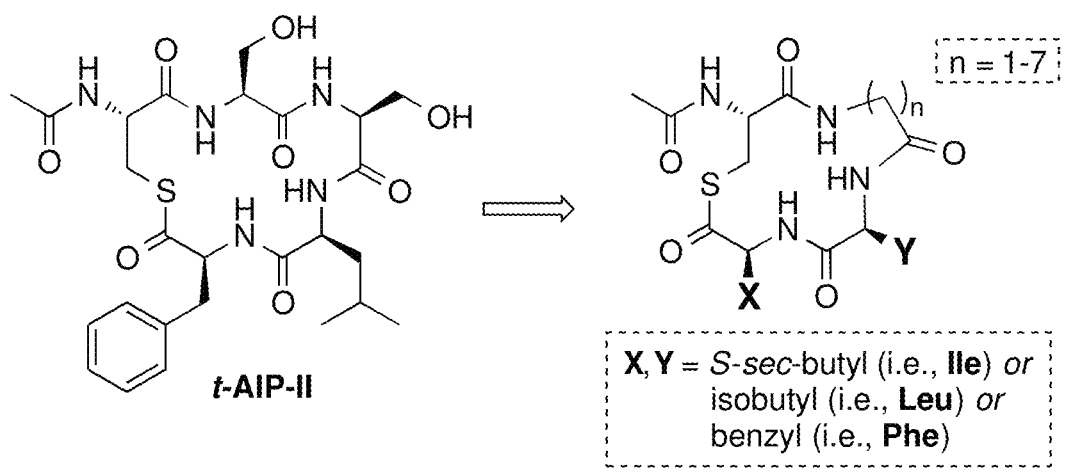
FIGS. 2A and 2B.

A first compound library of AIP mimetics was screened for AgrC modulatory activity in all four groups of S. aureus using strains containing yfp reporter. These strains are summarized in Table 1, and include the multidrug-resistant strain USA300 LAC.[17] In these S. aureus reporters, binding of the native AIP to AgrC activates YFP production and can be measured using fluorescence. Thus, compounds capable of inhibiting native AIP binding produce a reduction in fluorescence. Preliminary compound screening was performed at 10 µM in each strain; the full results of preliminary screening are shown in FIGS. 4A-4D. Key findings from these initial screens are summarized here. To simplify the discussion, the full library will be described as three smaller sub-libraries. In the first sub-library (termed $n_xLX$), there is a linker with n=x methylenes, residue 3 is Leu, and residue 4 (X) is Leu, Ile, or Phe (FIG. 2A). The second and third sub-libraries ($n_xIX$ and $n_xFX$) are identical to the first sub-library except that there is an Ile or Phe at residue 3, respectively.

In sub-library $n_xLX$, there were no compounds that completely abolished AgrC activity in group-I S. aureus, but n3LF reduced activity to 17% relative to a DMSO control. In group-II, n6LF completely inhibited AgrC activity. In group-III, n3LF, n5LF, n6LF, and n7LF all reduced AgrC activity to minimal levels. n3LF completely inhibited AgrC activity in group-IV, highlighting the potential similarities between group-I and group-IV (they do share almost identical native AIP ligand, FIG. 1B). Notably, all of the AgrC inhibitors identified in this sub-library contained Phe at residue 4.

In sub-library $n_xIX$, the overall inhibitory activity observed was low. These results suggest that the presence of Ile at residue 4 on the minimized t-AIP-II scaffold is detrimental to AgrC binding. This sub-library was only active in the group-III strain, with n5IF, n6IF, and n7IF reducing AgrC activity to minimal levels at a concentration of 10 µM. Interestingly, this set of active compounds contains the same Phe4 and has similar ring sizes as the group-III inhibitors identified in the $n_xLX$ library.

In sub-library $n_xFX$, n5FF, n6FF, and n7FF were found to reduce AgrC activity to minimal levels in all four groups of *S. aureus*, with n6FF displaying slightly less AgrC inhibition in group-II than n5FF and n7FF. Conspicuously, these compounds all contained two Phe residues at residues 3 and 4.

In determining which compounds to advance in this study, mimetics with the noted double Phe3 and Phe4 motif and ring sizes of n=5-7 were considered the most promising. Thus, n5FF, n6FF, and n7FF were selected from the peptidomimetic library (shown in FIG. 2B), and their AgrC inhibition was measured over a range of concentrations to better gauge their relative activities using the four *S. aureus* reporter strains. The assay results, shown in FIG. 3, identify n7FF as a potent pan-group AgrC inhibitor, based on statistically significant differences in activity.

Example 4

Second-Generation Compounds and Screening

Figure 2B:
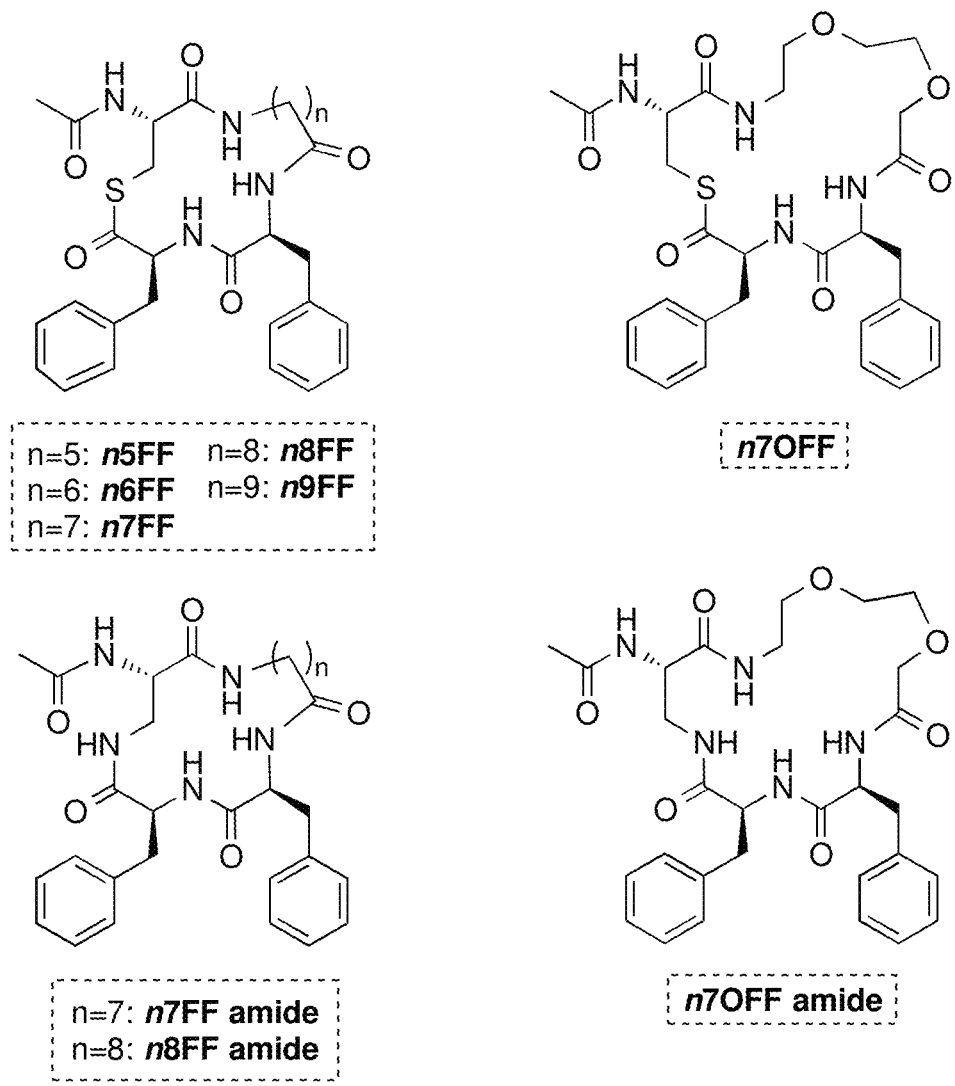
Figure 3A:
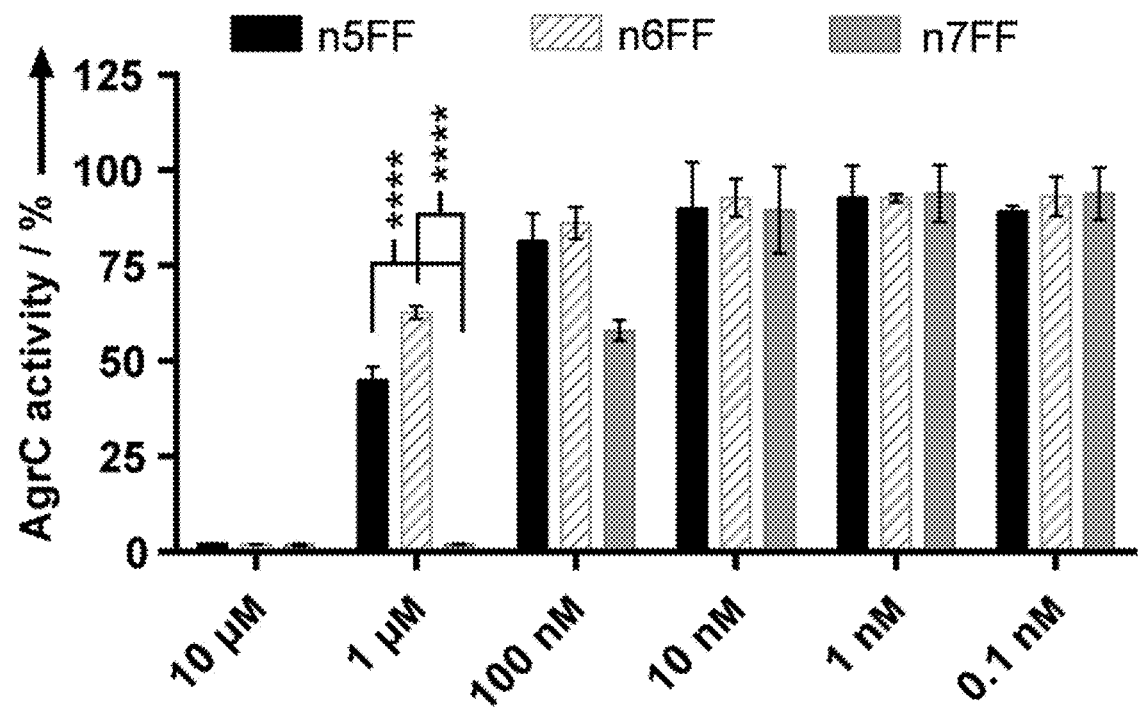
FIGS. 3A-3D. Summary of AgrC activity screening data for certain compounds. Compound activity data in S. aureus agr group-I (FIG. 3A), group-II (FIG. 3B), group-III (FIG. 3C), and group-IV (FIG. 3D) at concentrations from 10 μM to 100 pM. Bar graphs indicate percent AgrC activity as measured by yellow fluorescent protein (YFP) fluorescence using the S. aureus reporter strains. Error bars represent 95% confidence intervals. The results of two-tailed t-tests indicate that at 1 μM in groups-I, -II, and -IV, and at 100 nM in group-III, there is at least a largely significant statistical difference in compound activity for n5FF and n6FF versus n7FF.  is P≤0.01, * is P≤0.001, and **** is P≤0.0001.
Figure 3B:
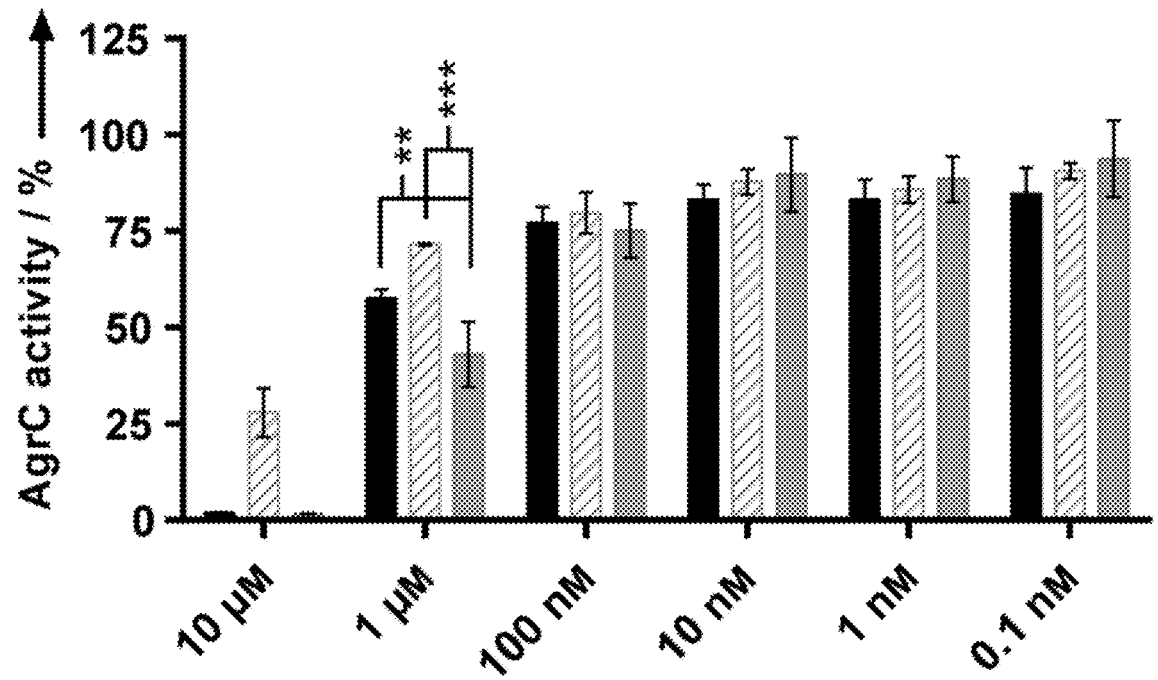
Figure 3C:
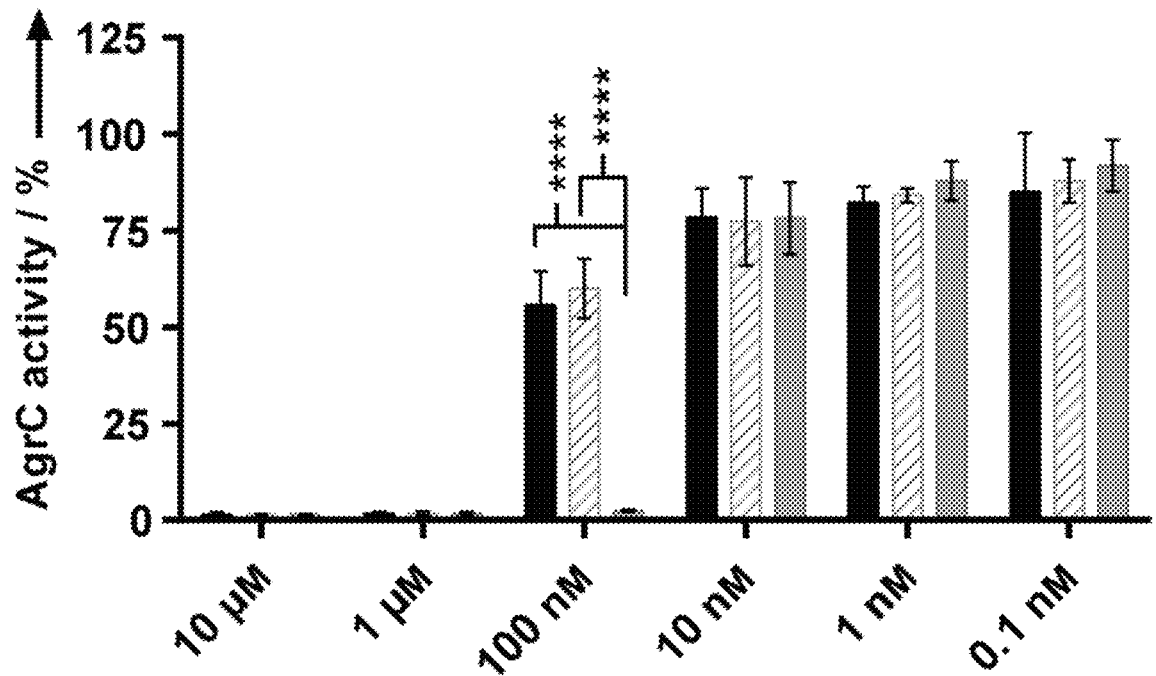
Figure 3D:
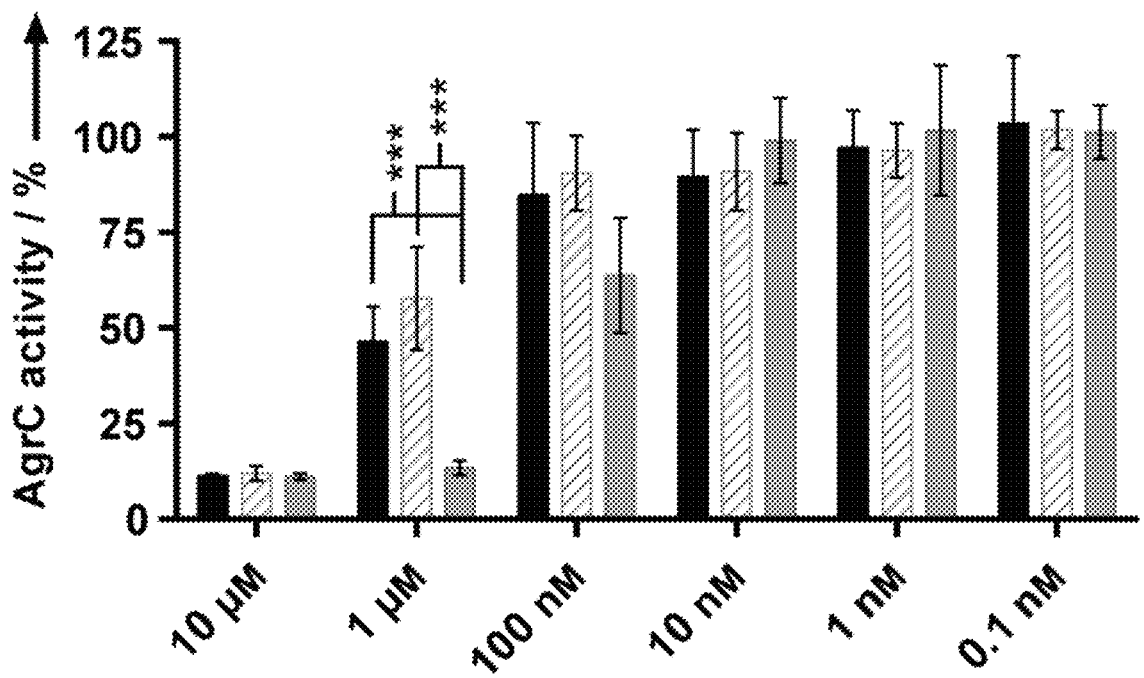
Figure 4A:
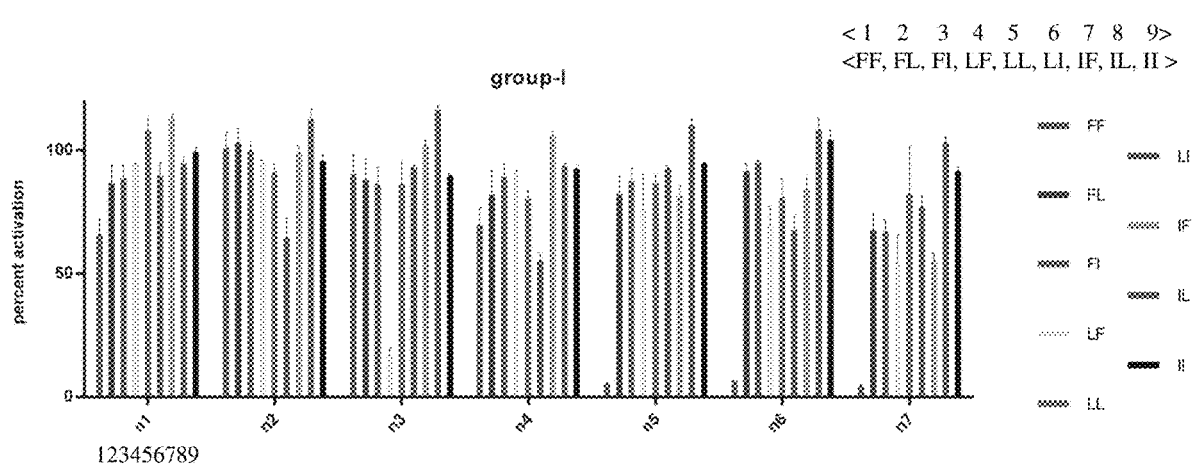
FIGS. 4A-4D. Screening data for the peptidomimetic library for AgrC modulatory activity in each group of S. aureus (I-IV), FIGS. 4A-4D, respectively, at 10 μM as determined using the YFP reporter strains. The nine compounds assessed are shown in the order FF, FL, FI, LF, LL, LI, IF, IL, II, bars 1-9, respectively. Percent AgrC activation indicates YFP fluorescence relative to a 1% DMSO control. Peptidomimetic structures are indicated by aliphatic bridge spacer length (n=1-7) on the x-axes of each plot and by amino acid residues in the legends for each plot. In the figures, error bars represent standard error measurement.
Figure 4B:
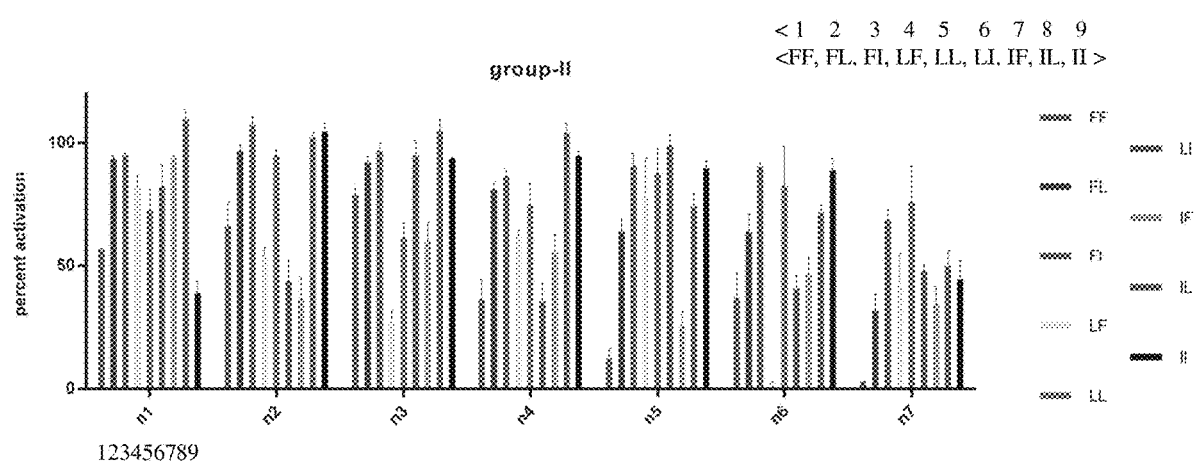
Figure 4C:
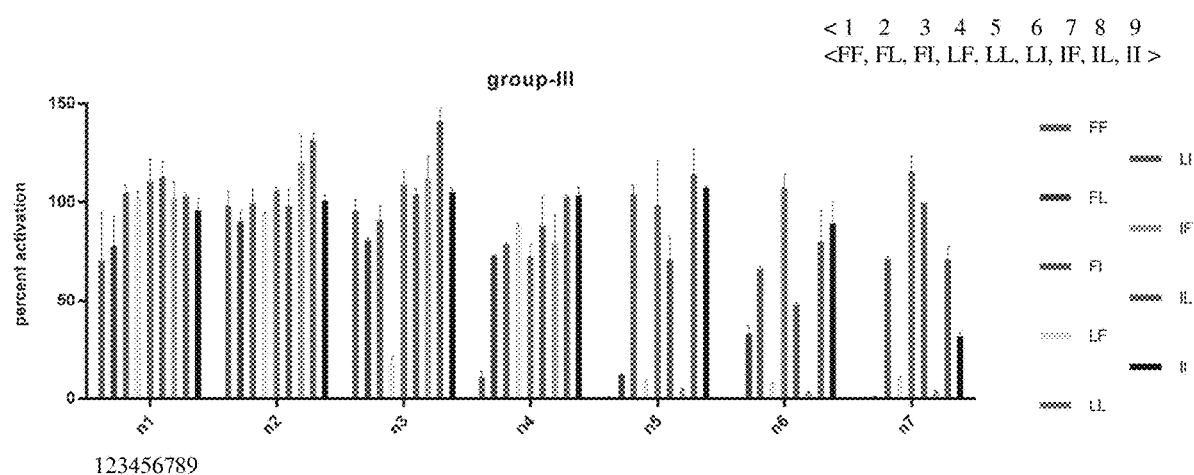
Figure 4D:
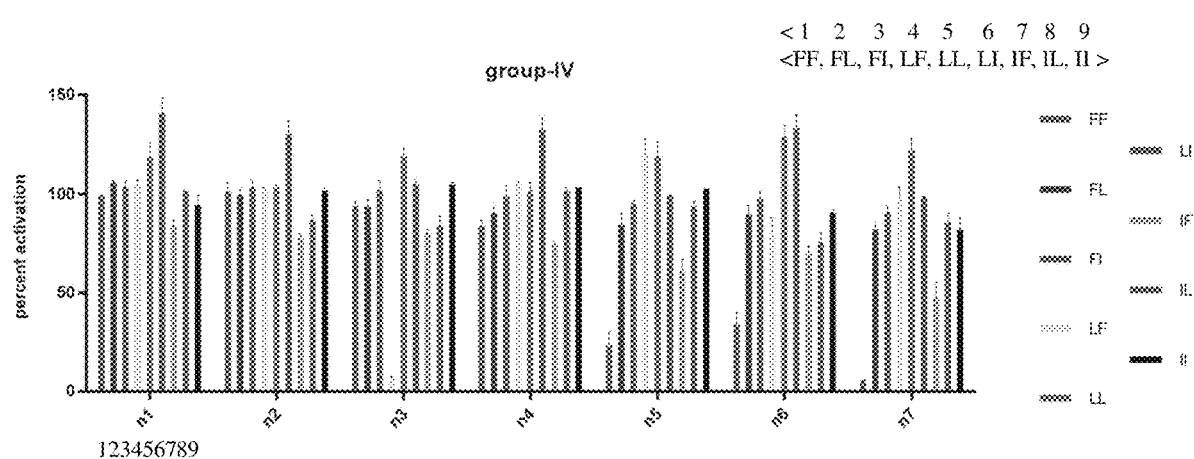
Figure 5:
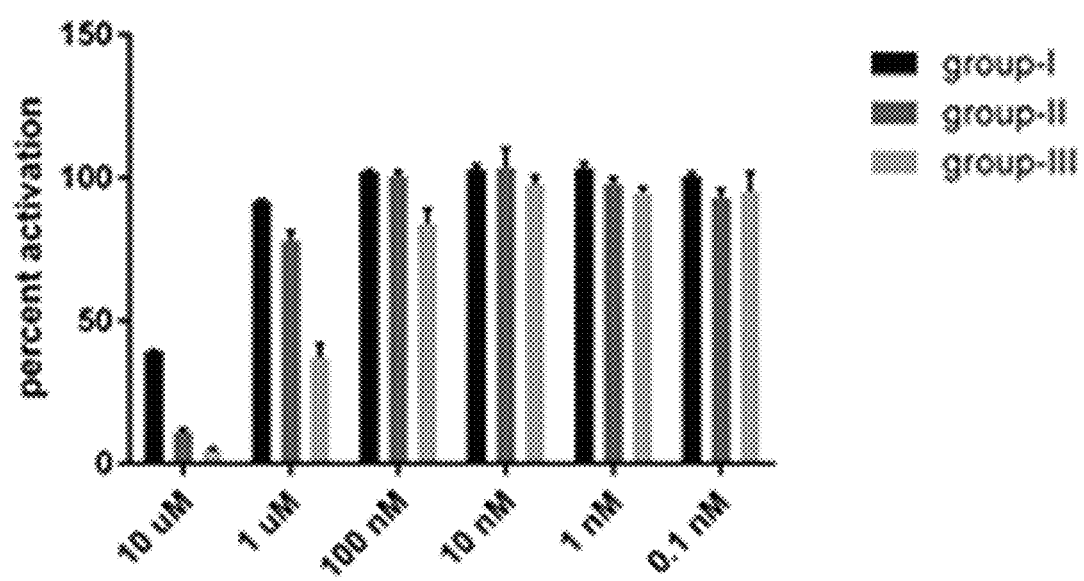
FIG. 5. Screening data for n9FF for AgrC modularity activity in groups-I-III of S. aureus as determined using the YFP reporter strains. Percent AgrC activation indicates YFP fluorescence relative to a 1% DMSO control. Error bars represent standard deviation of the technical triplicates for each biological replicate.
Figure 6A:
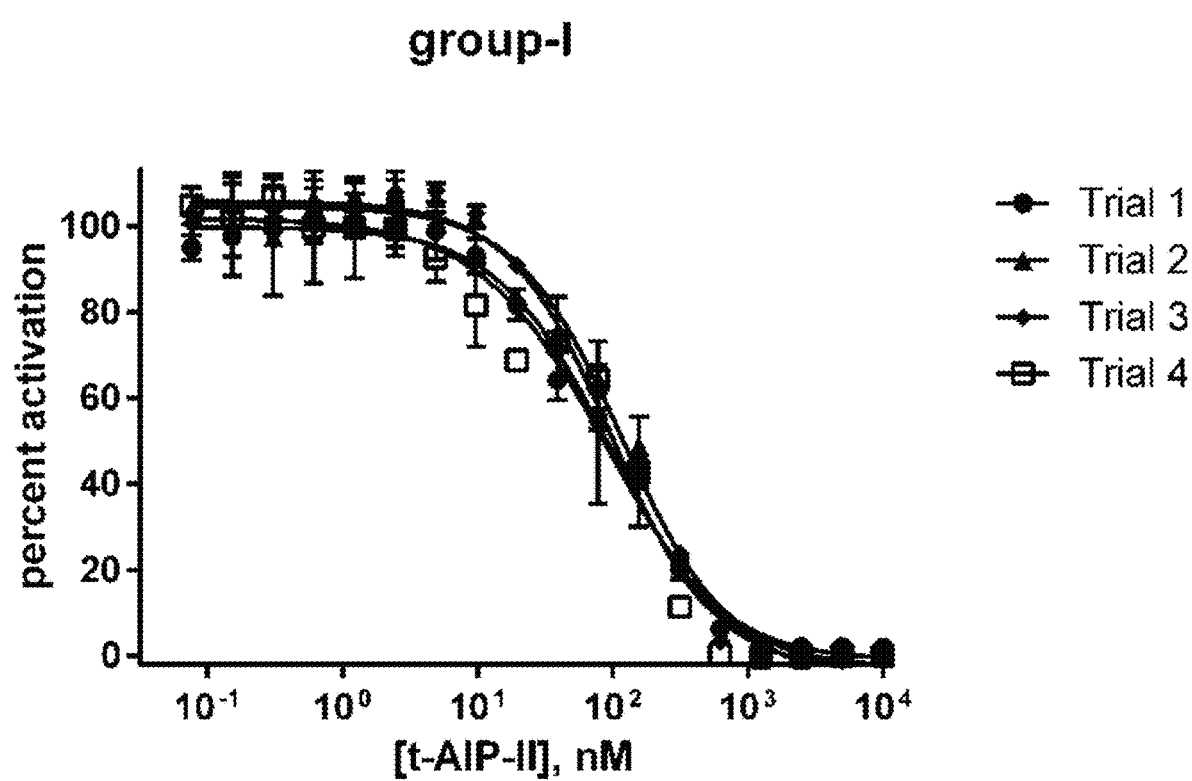
FIGS. 6A-6D. Dose response curves for AgrC antagonism by t-AIP-II in each group of S. aureus (I-IV), FIGS. 6A-6D, respectively, as determined using the YFP reporter strains. Error bars represent standard deviation of the technical triplicates for each biological replicate. $IC_{50}$ values calculated from these curves are reported in Table 2.
Figure 6B:
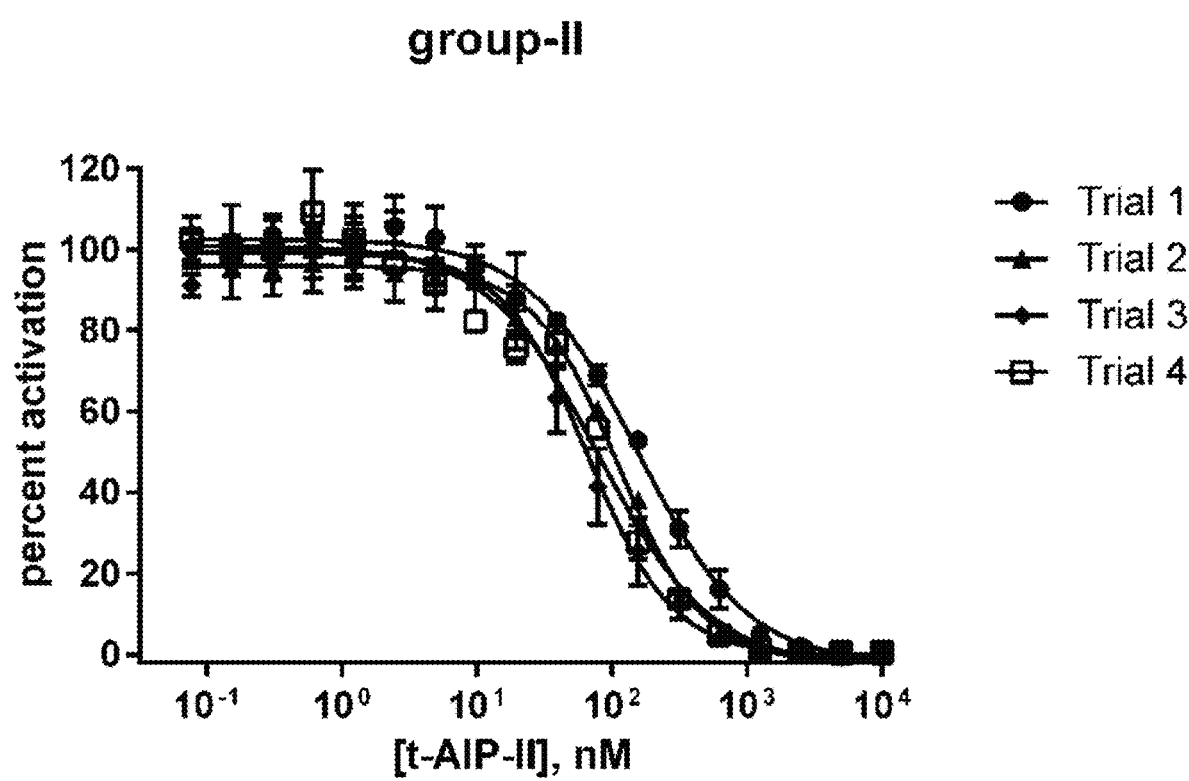
Figure 6C:
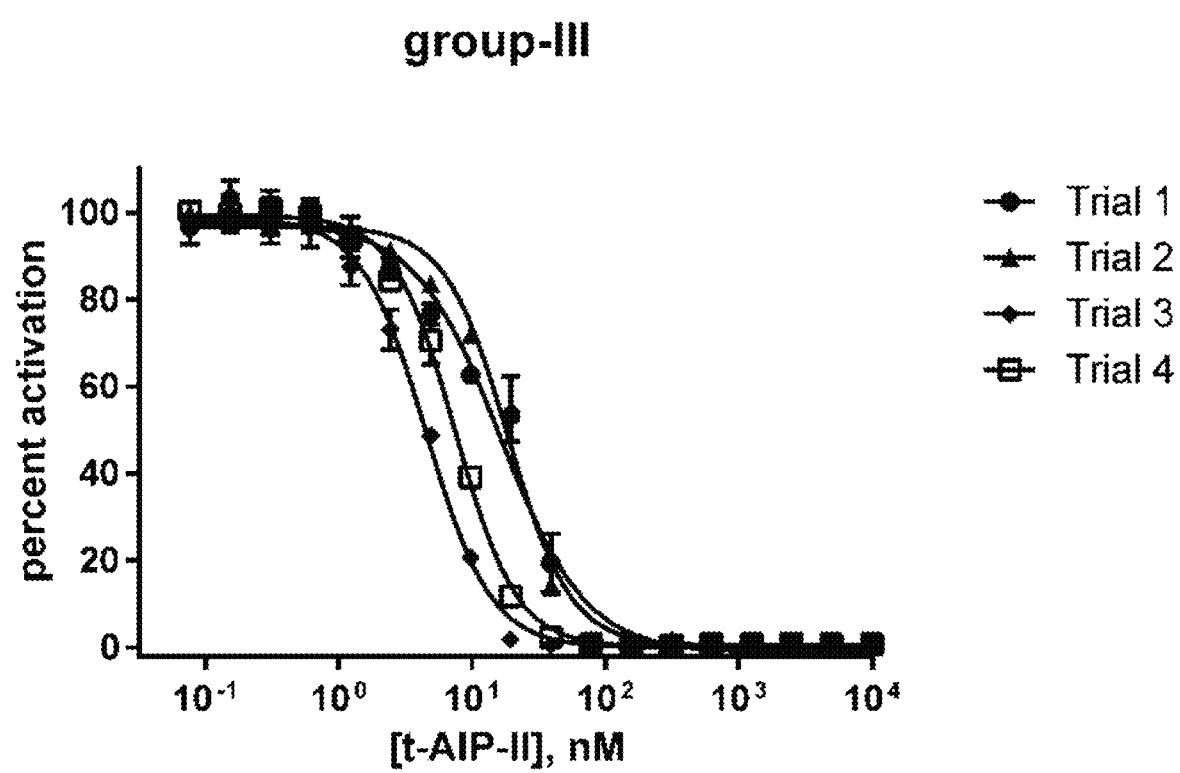
Figure 6D:
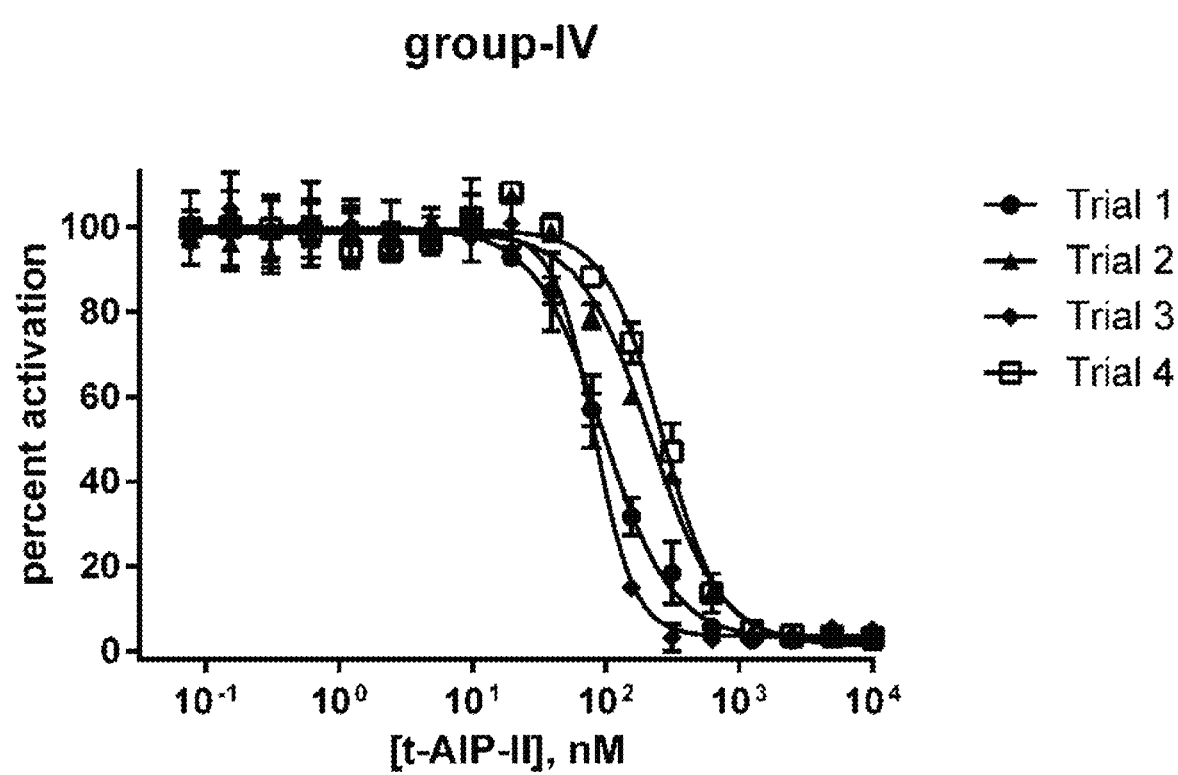
Figure 7A:
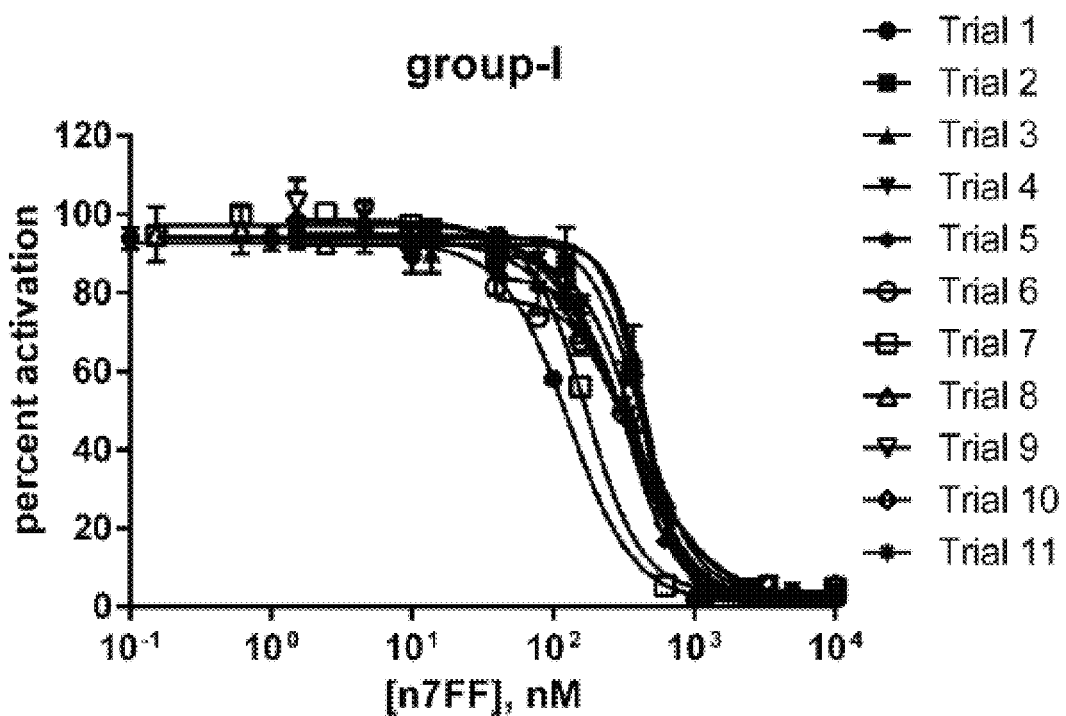
FIGS. 7A-7D. Dose response curves for AgrC antagonism by n7FF in each group of S. aureus (I-IV), FIGS. 7A-7D, respectively, as determined using the YFP reporter strains. Error bars represent standard deviation of the technical triplicates for each biological replicate. $IC_{50}$ values calculated from these curves are reported in Table 2.
Figure 7B:
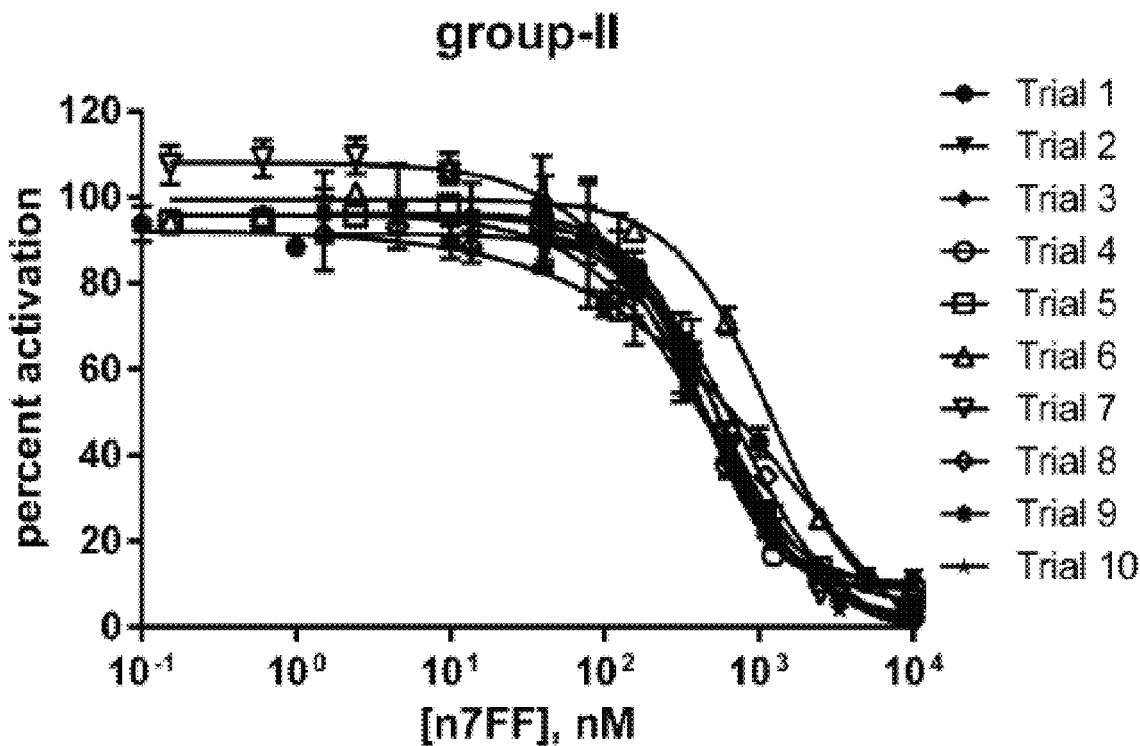
Figure 7C:
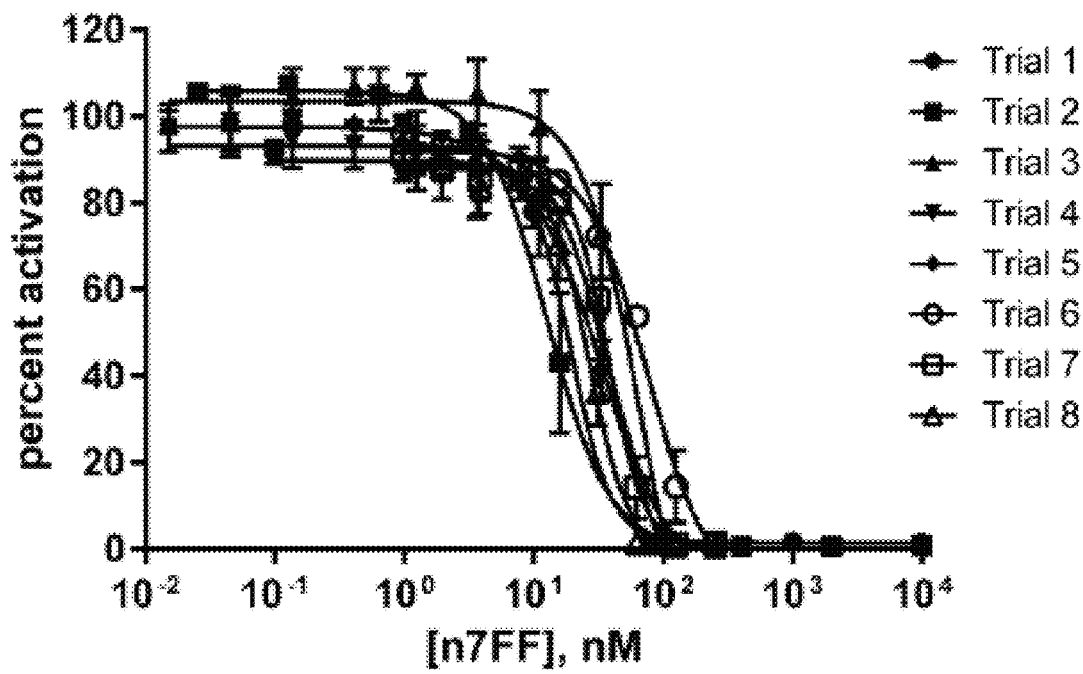
Figure 7D:
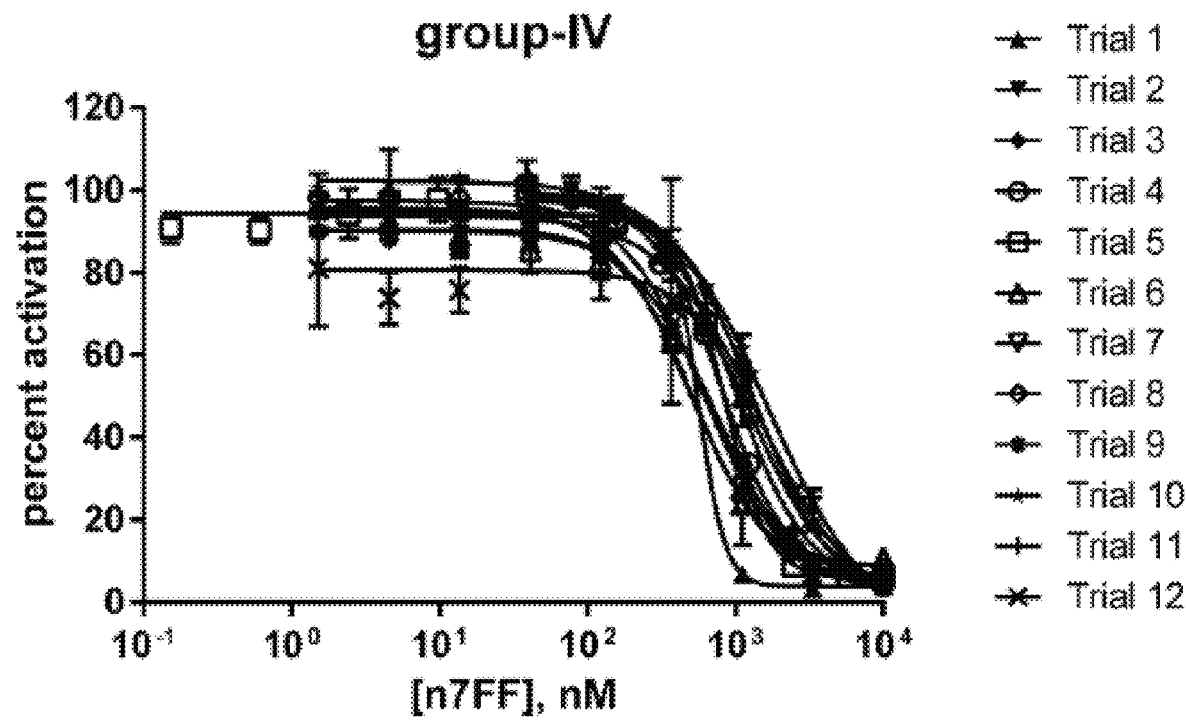
Figure 8A:
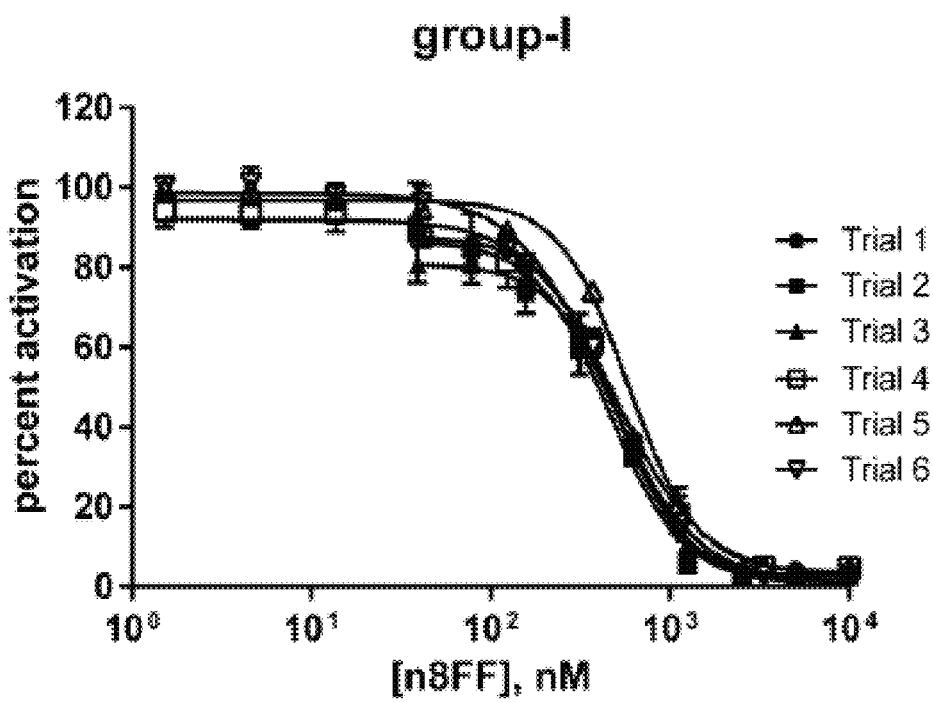
FIGS. 8A-8D. Dose response curves for AgrC antagonism by n8FF in each group of S. aureus (I-IV)<FIGS. 8A-8D, respectively, as determined using the YFP reporter strains. Error bars represent standard deviation of the technical triplicates for each biological replicate. $IC_{50}$ values calculated from these curves are reported in Table 2.
Figure 8B:
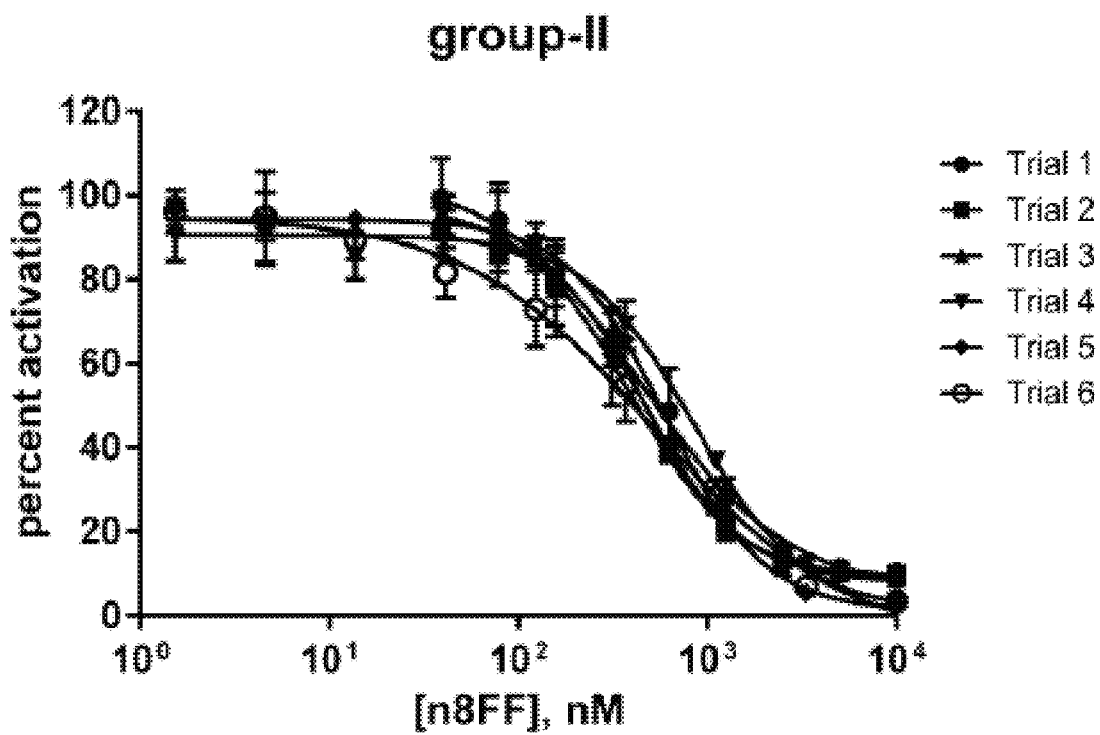
Figure 8C:
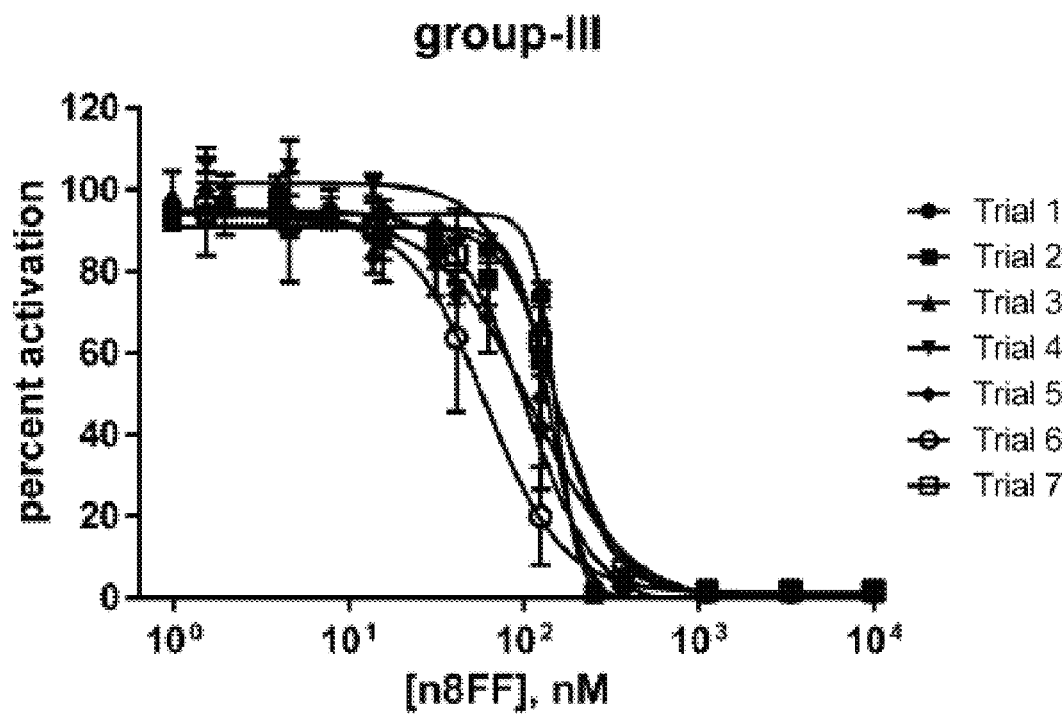
Figure 8D:
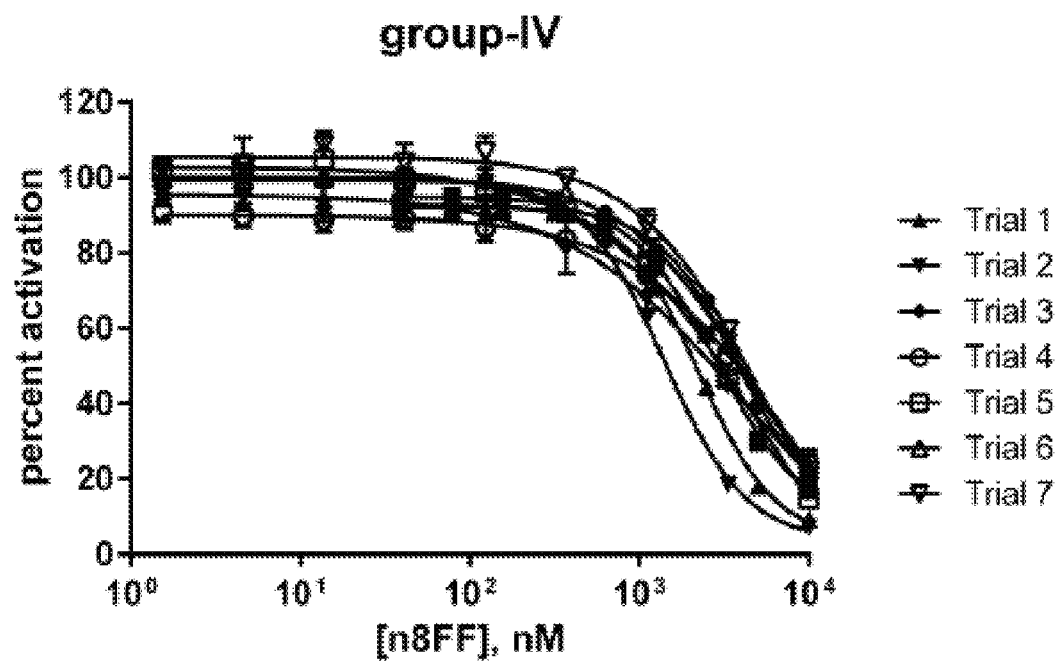
Figure 9A:
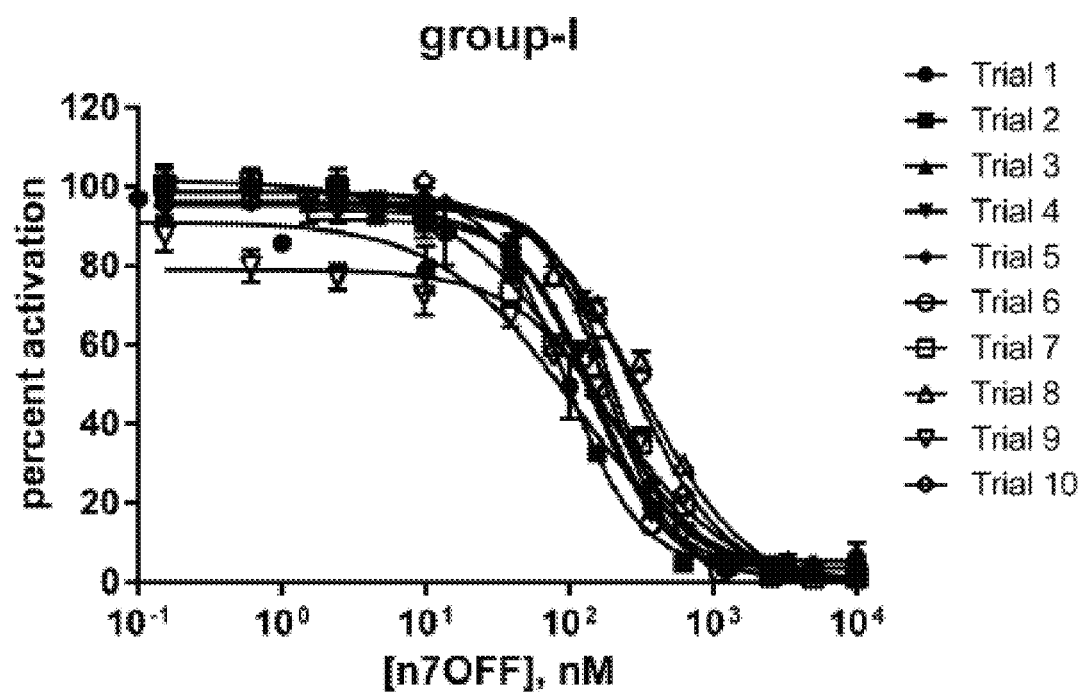
FIGS. 9A-9D. Dose response curves for AgrC antagonism by n7OFF in each group of S. aureus (I-IV), FIGS. 9A-9D, respectively, as determined with the YFP reporter strains. Error bars represent standard deviation of the technical triplicates for each biological replicate. $IC_{50}$ values calculated from these curves are reported in Table 2.
Figure 9B:
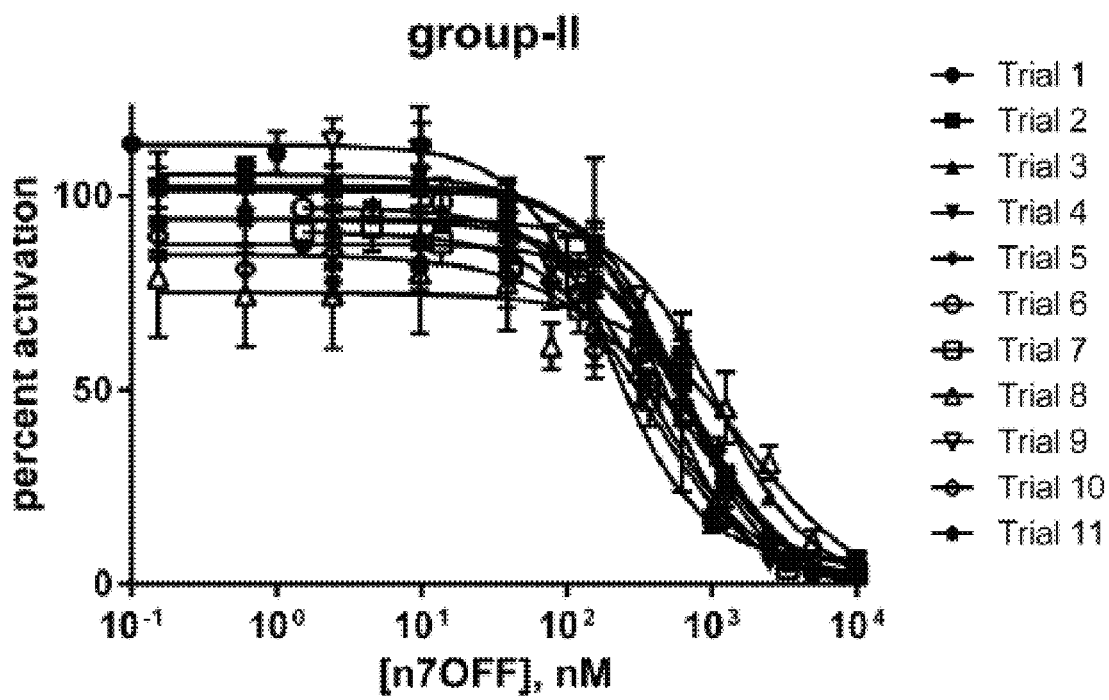
Figure 9C:
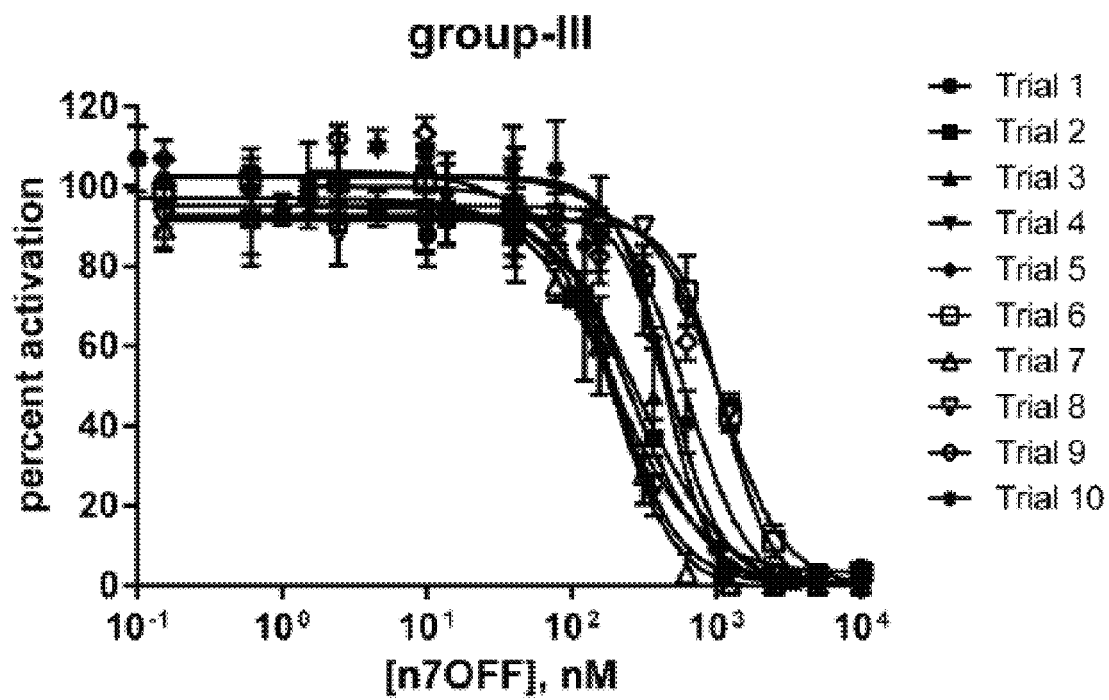
Figure 9D:
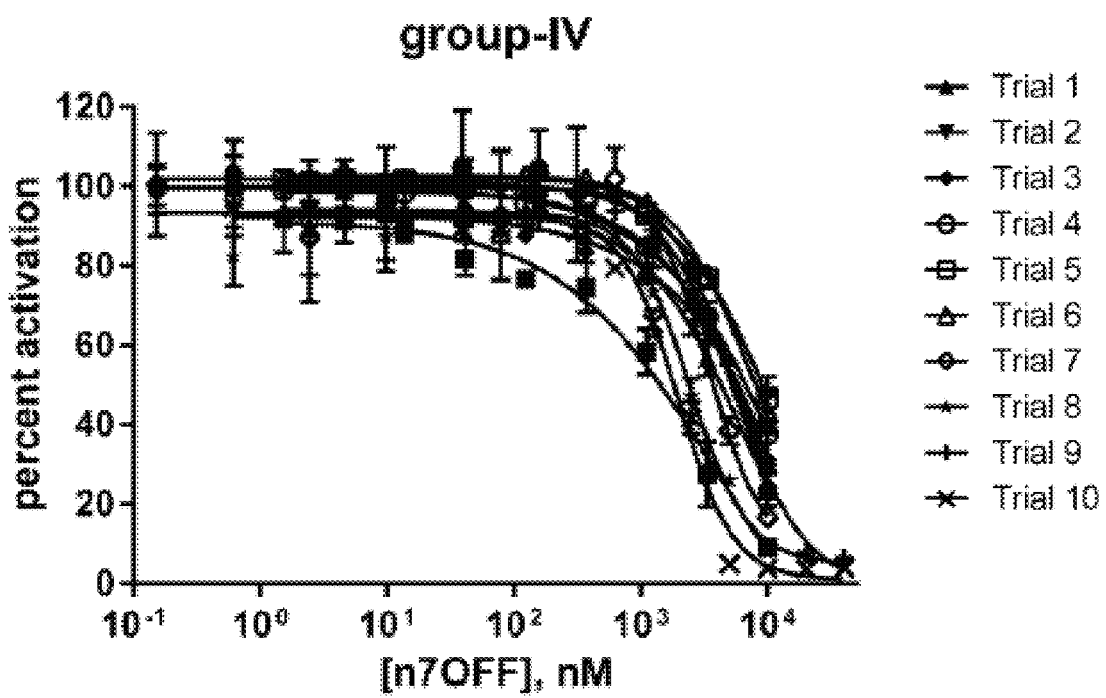
Figure 10A:
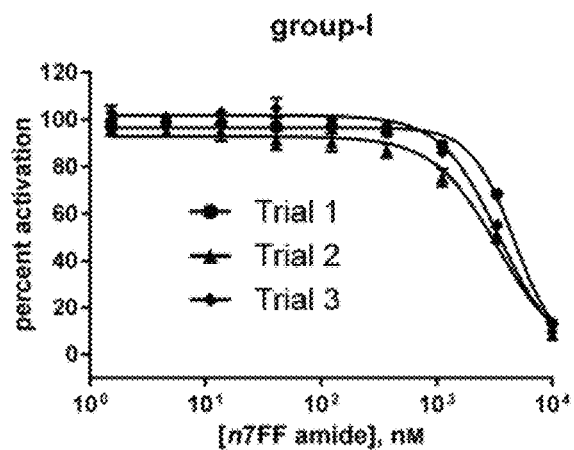
FIGS. 10A-10F. Dose response curves for AgrC antagonism by n7FF amide (FIGS. 10A, 10C, and 10E) and n8FF amide (FIGS. 10B, 10D, and 10F) in groups-I-III of S. aureus as determined using the YFP reporter strains. Error bars represent standard deviation of the technical triplicates for each biological replicate. $IC_{50}$ values calculated from these curves are reported in Table 2.
Figure 10B:
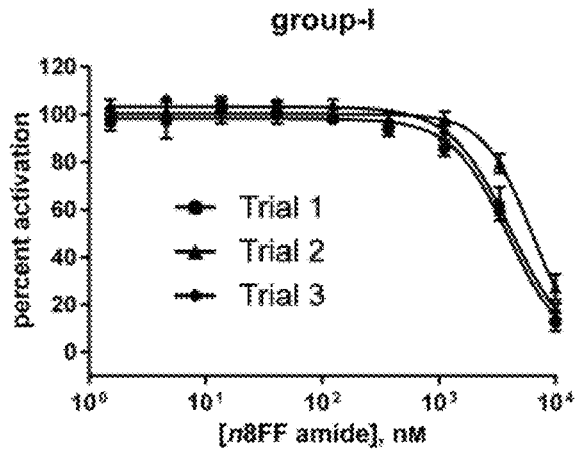
Figure 10C:
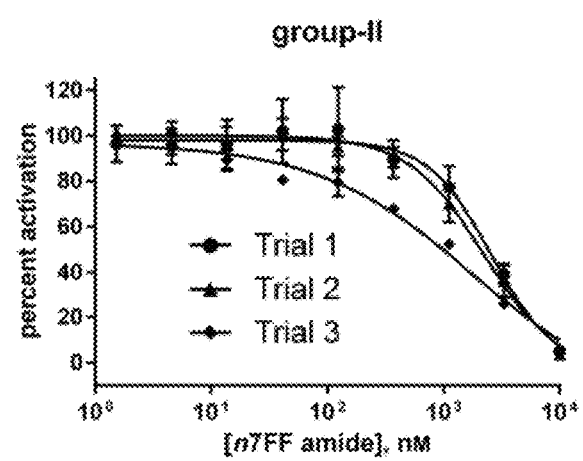
Figure 10D:
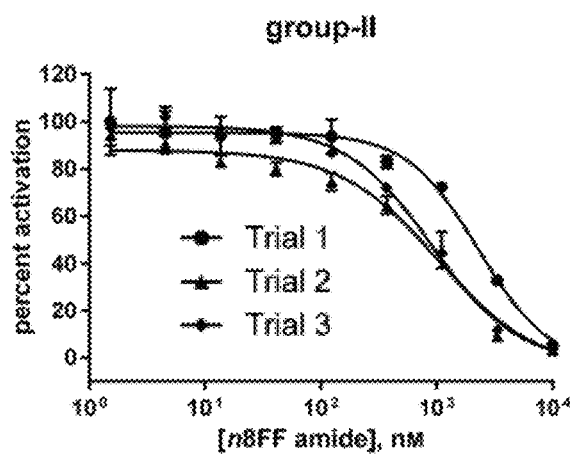
Figure 10E:
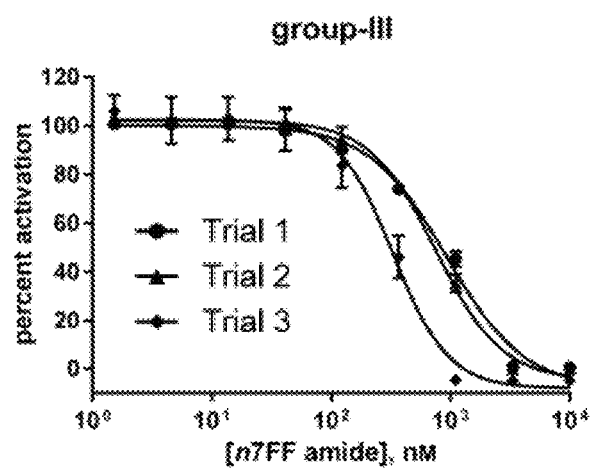
Figure 10F:
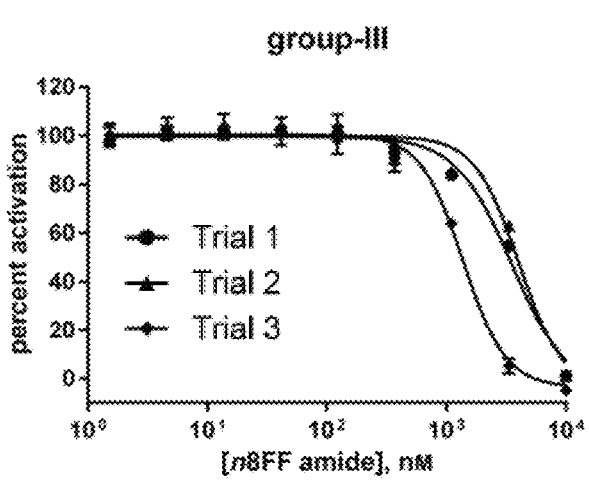

The structures of n5FF, n6FF, and n7FF were considered to further delineate features that were important for their activity profiles against AgrC and to design additional ligands with potentially enhanced activities. The 1- and 2-carbon ring-expanded homologs of n7FF, n8FF and n9FF, were prepared to examine how further expanded ring size impacted activity (FIG. 2B). Both were found to be inhibitors. n8FF demonstrated very similar activity relative to n7FF and the parent peptide t-AIP-II, while n9FF was less active than either n7FF or n8FF in groups-I-III, having estimated $IC_{50}$ values in the μM range (FIG. 5).[18] These results indicate that, at least for the $n_xFF$ series, the size of the flexible carbon linker can be varied without impacting the observed activity, and preferably, the number of atoms in the macrocycle should be three or four atoms greater than that in native AIP amide backbones (i.e., 16). Further, these data suggest that—assuming these minimized ligands target the same site on AgrC as native AIPs—all of the macrocycle amide contacts made by AIPs in the AgrC binding pocket may not be essential for binding, as long as the requisite space in the binding site is filled sufficiently.

Further study and manipulation of compounds n7FF and n8FF revealed that they had relatively low water solubilities, limiting their study at concentrations over 100 μM. Related derivatives that were less hydrophobic were then examined to ease their routine handling; such a characteristic should also enhance their utilities as eventual chemical probes. Beginning with compound n7FF, oxygen atoms were added into the linker to increase its capacity to form hydrogen bonds with solvent. Compound, n7OFF (for n7 oxo-linker FF, FIG. 2B), having two oxygens in the linker was readily prepared by incorporating the linker amino acid 8-(Fmoc-amino)-3,6-dioxaoctanoic acid (n7O) into the standard SPPS route.

n7OFF was found to be approximately 100-fold more soluble in water than n7FF, with a solubility near 10 mM. This difference in solubility is also apparent from calculated ClogP (n-octanol/water) values for these peptidomimetics (calculated values can be foun din Vasquez et al. 2017, [34]). Indeed, the ClogP values for t-AIP-II and n7OFF are very similar and relatively low (indicative of lower hydrophobicity); the ClogP values for n7FF, n8FF, and AIP-III D4A are also quite similar albeit larger than those for t-AIP-II and n7OFF (indicative of higher hydrophobicity; although in practice n7FF and n8FF are both less soluble than AIP-III D4A in water). In addition to possessing a desirable aqueous solubility profile, preliminary screening of n7OFF in the four AgrC reporter strains indicated that it was approximately as active as t-AIP-II, n7FF, and n8FF in groups-I-II, and modestly active in groups-III-IV (see FIGS. 6A-6D, 7A7-D, 8A-8D and 9A-9D).

Next, $n_xFF$ derivatives that lacked the labile thioester bond, were examined. The thioester bond is unstable in aqueous media at pH values above 7.4. [41] Derivatives of this type can exhibit prolonged lifetimes and possibly enhanced activities in biologically relevant settings. Amide-linked analogs of n7FF, n8FF, and n7OFF—termed n7FF amide, n8FF amide, and n7OFF amide (FIG. 2B) were prepared via the substitution of L-2,3-diaminopropionic acid (Dap) for Cys1 during the SPPS protocol, and a final macrolactamization step. These compounds (macrocyclic amides) were markedly more soluble in water than their parent thiolactones (also apparent in their Clog P values; see SI). Preliminary biological screening indicated that n7FF and n8FF amides both reduced (inhibited) AgrC activity to minimal levels in group-II and group-III at 10 μM, but that they were far less active in group-I and there was virtually no inhibition in group-IV at 10 μM. Thus, they were less active in these assays than their parents (FIGS. 10A-10F). In all the *S. aureus* reporters, n7OFF amide showed no significant activity at 10 μM. These results indicate that the thioester bond is important for AgrC:ligand interactions in the minimized t-AIP-II system studied.

Example 5

To facilitate a more quantitative comparison of the relative activities of exemplary inhibitors dose-response analyses was performed on n7FF, n8FF, and n7OFF using the group-I-IV *S. aureus* reporter strains and calculated $IC_{50}$ values for AgrC inhibition. As a key control, we included the parent peptide, t-AIP-II. Dose response data for n7FF amide, n8FF amide, and n7OFF amide were also collected for comparison to n7FF, n8FF, and n7OFF, respectively. The $IC_{50}$ data are summarized in Table 2 (for a complete compilation of all trials, see FIGS. 6A-6D, 7A-7D, 8A-8D, 9A-9D and 10A-10F).

TABLE 2

$IC_{50}$ values for selected peptidomimetics against *S. aureus* AgrC in groups-I-IV. CI = 95% confidence interval.[a]

| Inhibitor | Group-I $IC_{50}$, 95% CI (nM) | Group-II $IC_{50}$, 95% CI (nM) | Group-III $IC_{50}$, 95% CI (nM) | Group-IV $IC_{50}$, 95% CI (nM) |
|---|---|---|---|---|
| t-AIP-II[b] | 260 (95-695) | 230 (190-270) | 4 (3-5) | 150 (90-260) |
| t-AIP-II[c] | 101 (88-117) | 97 (94-112) | 9.3 (7.7-11.4) | 140 (118-166) |
| n7FF | 340 (308-376) | 495 (435-564) | 34.8 (30.8-39.4) | 985 (825-1176) |
| n8FF | 468 (422-518) | 479 (410-559) | 125 (109-142) | 3486 (2301-5280) |

TABLE 2-continued

IC$_{50}$ values for selected peptidomimetics against *S. aureus*
AgrC in groups-I-IV. CI = 95% confidence interval.[a]

| Inhibitor | Group-I IC$_{50}$, 95% CI (nM) | Group-II IC$_{50}$, 95% CI (nM) | Group-III IC$_{50}$, 95% CI (nM) | Group-IV IC$_{50}$, 95% CI (nM) |
|---|---|---|---|---|
| n7OFF | 181 (154-213) | 583 (468-725) | 332 (280-395) | 5938 (4221-8352) |
| n7FF amide | 3935 (3593-4309) | 2200 (1727-2801) | 573 (472-696) | —[d] |
| n8FF amide | 4742 (4335-5187) | 1339 (1065-1683) | 2613 (2180-3131) | —[d] |
| n7OFF amide | —[e] | —[e] | —[e] | —[e] |

[a]See Experimental Section for details of strains and assay protocols.
[b]Values reproduced from reference 5l using different *S. aureus* reporter strains.
[c]Values differ slightly in groups-III and -IV from those previously reported in reference 4k due to day-to-day assay variations.
[d]Data not shown due to non-sigmoidal curves in group-IV, with maximal inhibition not reached at the highest concentration tested.
[e]Inactive over the concentrations tested.

The dose response analyses revealed that n7FF was the most consistent with regard to potency, as it maintained IC$_{50}$ values within 3-7 fold of those for t-AIP-II in all four groups of *S. aureus*. The one carbon larger homolog, n8FF, was largely equipotent to n7FF in groups-I and -II, but 4-fold less potent in groups-III and -IV. The more soluble mimetic, n7OFF, was almost 2-fold more potent than n7FF in group-I, largely equipotent in group-II, and far less potent in groups-III and -IV. Notably, the potency of n7OFF in group-I matches that of the parent truncated AIP, t-AIP-II. This activity profile in groups-I and -II (the two more common *S. aureus* groups in human infection), [7b] coupled with its heightened aqueous solubility, indicate that the n7OFF scaffold could prove useful in various applications of QS inhibition in *S aureus*.

The amide analogues of n7FF and n8FF were far less potent than their parents (i.e., ~10-fold increase in IC$_{50}$ value; Table 2), and n7OFF amide was essentially inactive at all concentrations tested. Again, this loss in potency for the amide analogues relative to their thioester parents suggests that the thioester motif is important for the binding of these simplified AIP-II mimics to AgrC receptors, again assuming that they target AgrC directly.

Example 6

To gain further insights into the origins of its biological activity, the structure of n7OFF was characterized in aqueous solution by NMR methods. Such studies can be valuable in analyses of AIP-type derivatives that inhibit AgrC receptor activity.[4h, 4k, 4l] As n7OFF was based on the structure of t-AIP-II, a first step was to compare the structures of these two compounds in water. In addition, the structure of n7OFF to the highly potent *S. aureus* AgrC inhibitor, AIP-III D4A (sequence=I-N-[C-A-F-L-L]), was compared to gain insights into any structural similarities or differences that may relate to the activity profile for n7OFF. NMR structures for both t-AIP-II[4k] and AIP-III D4A,[4h] have been reported, albeit in a mixed solvent system (acetonitrile:water). By using a higher field spectrometer equipped with a cryoprobe in the current study, solution-phase NMR structures of t-AIP-II, AIP-III D4A, and n7OFF were obtained in water without addition of organic solvent. The new structures were solved using 2D ROESY spectra with excitation sculpting solvent suppression, with accompanying 1D proton and 2D TOCSY spectra to determine chemical shifts of proton resonances and aid in sequential assignments (a $^1$H—$^{13}$C HSQC spectrum was also used for n7OFF; see Vasquez et al. [34]). Using MestReNova 10 NMR software and Xplor-NIH,[19] low energy ensembles were used to find the most representative low-energy structures based on relative energy and RMS differences from the ensemble averages using PyMOL (See Figures S8-S13, in the Supplemental Information for Vasques et al. 2017) [34].

Not surprisingly, the structures of t-AIP-II in water and in the mixed solvent system were essentially identical, with a single amide bond contorted (Ser2 to Ser3) and the two serine sidechains in slightly different rotational conformations (See surface plots and overlay in Vasquez et al. 2017 [34]). The relatively large number of ROE peaks observed in the ROESY spectrum and the intensities of the interresidue peaks suggested that t-AIP-II adopts a highly rigidified conformation, as had been observed previously (ensemble average RMSD for the amide backbone atoms of only 0.05 Å). [4k] As before, the Leu4 and Phe5 side chains were positioned adjacently and pointed directly outwards away from the macrocycle. Similar to t-AIP-II, a comparison of the old and new solution structures for AIP-III D4A revealed only very subtle differences (See surface plots and overlay [34]). The resolution of the newer NMR solution-structure is similar to the original structure, with an ensemble average RMSD of 0.69 Å for the amide backbone atoms [34]. These results indicate that previous conclusions drawn from the structures of t-AIP-II and AIP-III D4A in the mixed solvent system should also apply in pure water.

Turning to the n7OFF structure in water, the two endocyclic Phe residues are well structured (See surface plots [34]), with multiple constraints indicated during analysis. Conversely, there were relatively few constraints indicated for the linker region, suggesting that movement of the linker atoms is sufficiently great to avoid the build-up of magnetization required for ROEs to be observed during the NMR experiment. The backbone atom RMSD from the ensemble was therefore relatively large compared to t-AIP-II and AIP-III D4A, at 0.96 Å.

The NMR structures of t-AIP-II, AIP-III D4A, and n7OFF were compared in water. An initial examination of the placement of heteroatoms and hydrophobic amino acid residues suggests that all three structures are largely amphipathic (from observations using an Eisenberg hydrophobicity scale; see surface plots [34]). [20] Each structure has a hydrophilic face opposite from a hydrophobic face, with aliphatic/aromatic groups that are clustered on the hydrophobic face of the peptide. It is interesting to note that previous SAR studies provide evidence that there is a hydrophobic binding pocket for AIP ligand recognition on AgrC receptors.[5m, 5t] The amphipathic nature of this trio of ligands may allow the hydrophobic face to insert in the proposed hydrophobic cleft of AgrC, while the hydrophilic face engages in favorable solvent interactions. The conformations adopted in aqueous solution may be relevant to AgrC binding, as it is likely that these macrocyclic, constrained compounds are spending a majority of the time in a conformation in aqueous media that is favorable for AgrC binding. With this in mind, overlays of t-AIP-II and n7OFF, and AIP-III D4A and n7OFF, were examined using minimized RMS of similar atoms to gain further insights into the similarities and differences between these three structures (See FIGS. 5A and B in Vasquez et a. 2017 [34]).

Overlays of the major solution conformations for t-AIP-II and n7OFF, and AIP-III D4A and n7OFF, show the two C-terminal residues and the bulk of the macrocycles on the hydrophobic faces of each compound occupy very similar positions. The RMS differences of the 19 atoms used for the fits of t-AIP-II with n7OFF and AIP-III D4A with n7OFF were 0.17 Å, and 0.34 Å, respectively; note, these 19 atoms were all on the hydrophobic faces (additional views are available in the supplemental information of Vasquez et al. [34]). Although the N-terminal acetyl group of n7OFF and the flexible linker point away from the other macrocyclic elements of t-AIP-II and AIP-III D4A, they both lie in the region suspected as being hydrophilic, and therefore are likely to be positioned outside of the expected hydrophobic binding site on AgrC. When comparing the orientation of the macrocycle of t-AIP-II to that of n7OFF, it is seen that the rigid macrocycle of t-AIP-II extends above the flexible linker in the n7OFF structure. In addition, when studying both overlays in relation to n7OFF, the space occupied by the N-terminal acetyl group, Cys1, and Ser2 of the t-AIP-II macrocycle appears to be positioned similarly to Ile1 and Asn2 in the exocyclic tail of AIP-III D4A. In view of these collective structural features, it is possible that both t-AIP-II and n7OFF have reduced inhibitory activities relative to AIP-III D4A because although they each can occupy a portion of space filled by AIP-III D4A, neither of them can completely fill the AgrC ligand-binding pocket quite as well as AIP-III D4A.

This study has developed and characterized structurally simplified AIP mimetics as modulators of agr-type QS in the pathogen S. aureus. This work describes the synthesis, and biological characterization of simplified mimetics of the truncated native AIP, t-AIP-II. A focused library of peptidomimetics was prepared via SPPS and evaluated for AgrC inhibition in the four agr groups of S. aureus using reporter gene assays. Follow-up studies on certain compounds and second-generation mimetic design revealed three preferred peptidomimetics (n7FF, n8FF, and n7OFF) that were capable of inhibiting AgrC activity in clinically relevant group-I S. aureus strains with potencies similar to the parent peptide. In addition, n7FF maintains potencies in all four S. aureus groups largely similar to t-AIP-II, while n7OFF displays enhanced water solubility relative to n7FF and n8FF.

Three structural features were associated with compound activity. First, Phe3 and Phe4 were conserved in each of the most active peptidomimetics, suggesting that AgrC binding is strong for this compound set when such hydrophobic, aromatic residues are present on the macrocycle. Second, the thioester moiety appears important for ligand recognition, as modification to an amide can largely obliterate activity of certai compounds. Third, an aliphatic chain of seven carbons (—$(CH_2)_7$—) in the mimetic macrocycle (n=7) appears preferred for inhibitory activity against AgrC receptors.

A series of solution-phase NMR experiments were performed to gain insights into the structure of n7OFF, in aqueous solution. Structural comparisons of n7OFF with its parent peptide, t-AIP-II, and previously reported potent AgrC inhibitor, AIP-III D4A, revealed a conserved amphipathic motif, with structural overlays emphasizing significant similarity in the respective hydrophobic regions of each molecule. These similarities in the hydrophobic region, which are posited to be important for AgrC binding, could prove useful in the design of future AIP mimetics.

The biological and structural results reported herein for peptidomimetics n7FF, n8FF, and n7OFF show that such a minimized AIP scaffold retains activity as a viable AgrC inhibitor. Preferred mimetics are highly soluble, physically robust, and amenable to larger scale synthesis relative to peptidic variants. Molecules of this type represent valuable tools to study fundamental aspects of QS in S. aureus and its viability as a therapeutic target.

Example 7

Screening of Exemplary Compounds Having Alkoxyalkyl Linkers

The following compounds were prepared by methods described hereinabove:

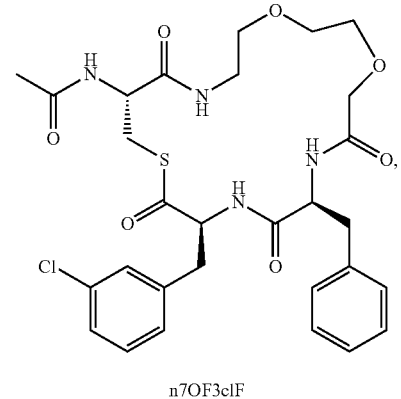

n7OF3clF

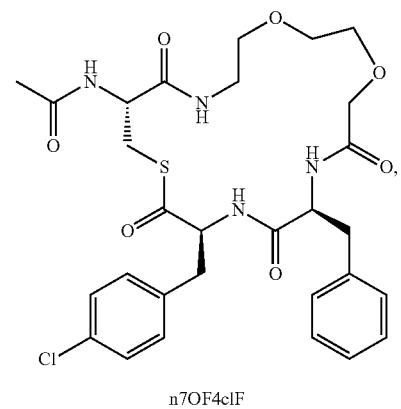

n7OF4clF

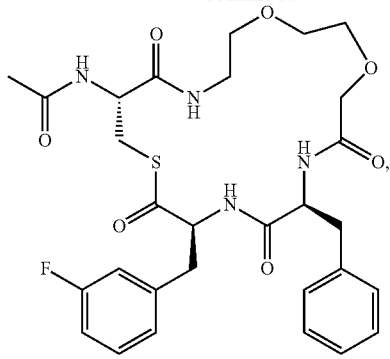

n7OF3fF

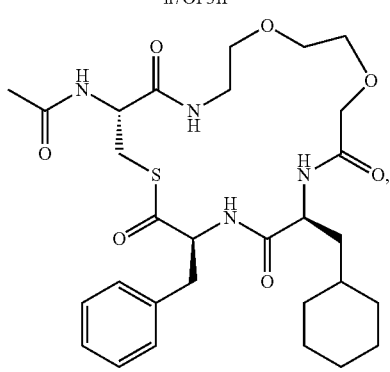

n7OChaF

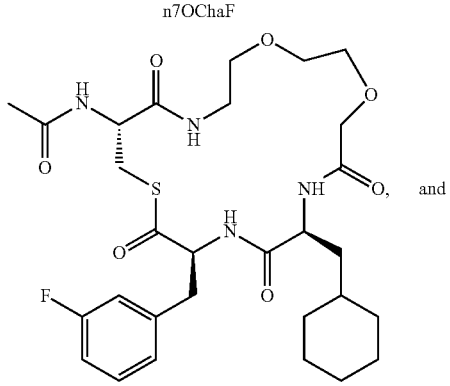

n7OCha3fF

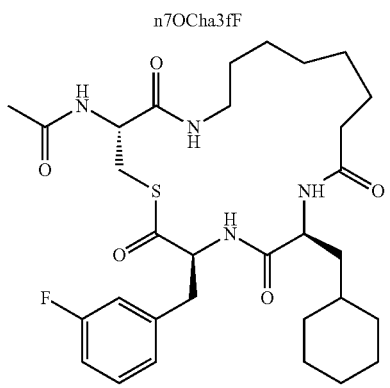

n7Cha3fF

Table 3 provides IC$_{50}$ values for these compounds against *S. aureus* AgrC in groups-I-IV compared to these values for compound n7OFF.

TABLE 3

| Compound | IC$_{50}$ (nM) | | | |
| --- | --- | --- | --- | --- |
|  | Group-I | Group-II | Group-III | Group-VI |
| n7OFF | 181 | 583 | 332 | 5940 |
| n7OF3clF | 225 | 217 | 1138 | — |
| n7OF4clF | 2590 | 113 | 2480 | >5000 |
| n7OF3fF | 40 | 1210 | 171 | >5000 |
| n7OChaF | 998 | 790 | 205 | 1080 |
| n7OCha3fF | 109 | 1383 | 35 | 597 |
| n7Cha3fF | 429 | 2344 | 19 | 1164 |

Additional exemplary compounds of Formula I include:

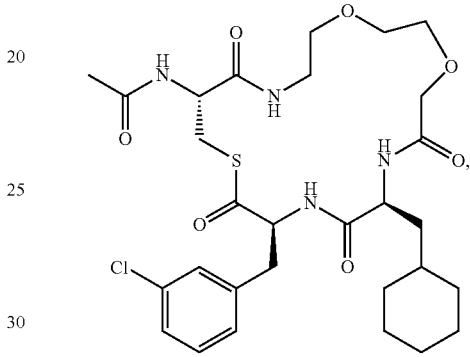

n7OCha4clF

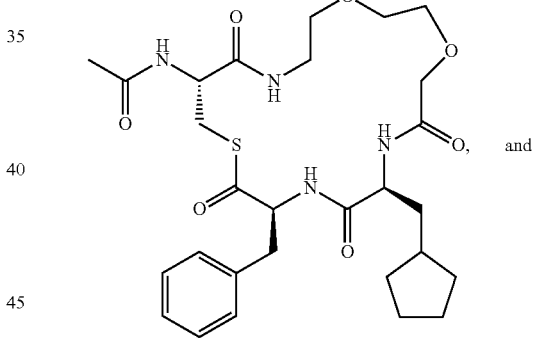

n7OCpaF

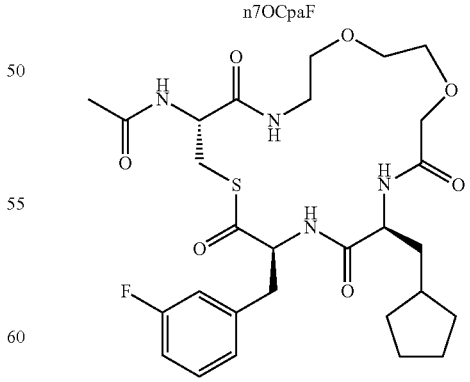

n7OCpa3fF

Again these compounds are prepared as described above with appropriate choice of starting materials.

Example 8

Exemplary Synthesis of Compounds of Formula IV and Those of Formulas I and II, where —W—CO— is a Carbon-Carbon Double Bond Compounds of Formula IV:

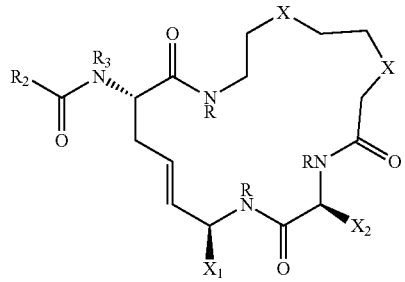

or salts or solvates thereof are prepared as illustrated in Scheme 1 for the exemplified compound of Formula IV where each R and $R_3$ are hydrogen, $R_2$ is methyl, $X_1$ is benzyl and $X_2$ is benzyl. Compounds of this formula with different R, $R_2$, $R_3$, $X_1$ and $X_2$ groups are prepared by the exemplified method by routine choice of appropriate starting materials. Compounds of Formula I where —W—CO— is a double bond are prepared by similar methods, where the desired linker $L_1$ is introduced by solution-phase peptide synthesis.

Compounds of Formula IV where variables are as defined in Formulas I, II, or III are modulators of quorum sensing in strains of *Staphylococcus* and particularly in strains of *S. aureus* and *S. epidermidis*. Certain compounds of Formula IV are inhibitors of quorum sensing in strains of *Staphylococcus*. Certain compounds of Formula IV are activators of quorum sensing in strains of *Staphylococcus*.

In summary in Scheme 1, the exemplary compound of Formula IV, where both X are either —O—, is prepared. Amino-aldehyde precursor (20) is prepared by oxidizing a selected amino-alcohol. This precursor amino-aldehyde can be prepared to provide for any $X_1$ or $X_2$ group as defined in the Formulas I, II or III herein. The reagent MePPh3Br is prepared as illustrated and is used as illustrated to generate the corresponding amino-olefin (30) which is used as a starting material in standard solution-phase coupling to prepare a linear precursor with two terminal olefins (40) as illustrated in Scheme 1. and where the generic precursor of Formula VII is shown below. Ring-closing metathesis is used to make the macrocyclic peptidomimetic of Formula IV. The precursor of Formula VII has generic formula:

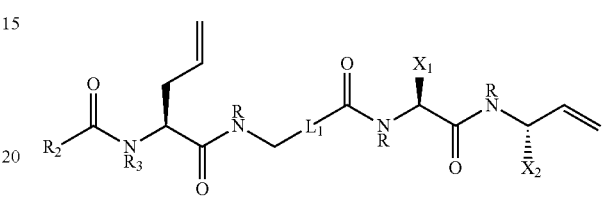

or salts or solvates thereof, where:

$L_1$, R, $R_3$, $R_2$, $X_1$ and $X_2$ are as defined for Formula I, II, or III.

A more specific precursor of Formula IVA is:

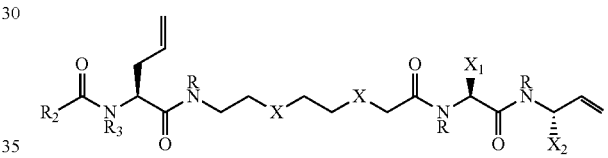

or salts or solvates thereof, where X is —O— or —$CH_2$— and R, $R_3$, $R_2$, $X_1$ and $X_2$ are as defined for Formula I, II, or III.

Scheme 1

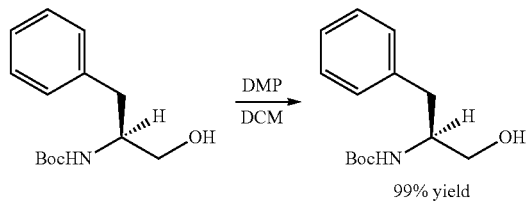

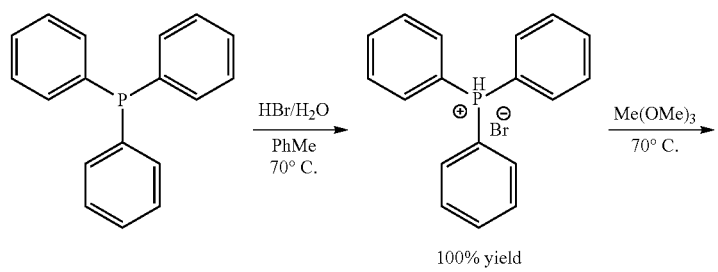

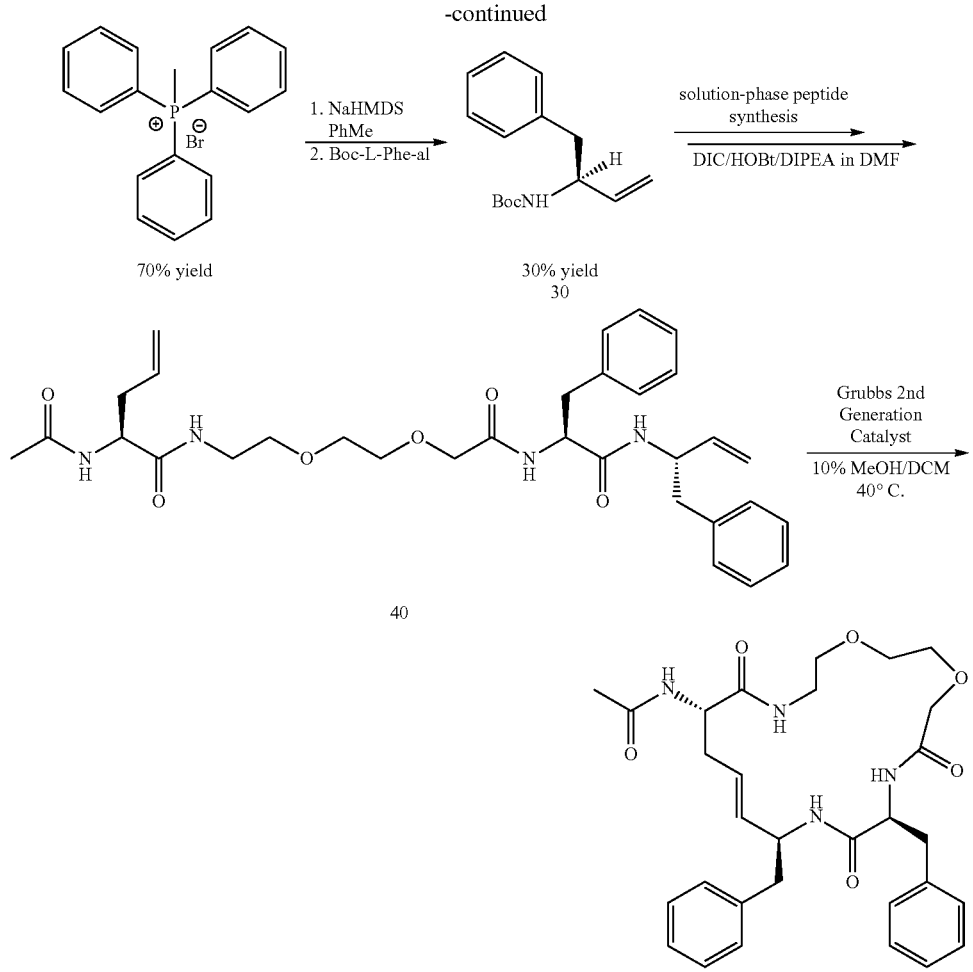

REFERENCES

[1] a) S. T. Rutherford, B. L. Bassler, Cold Spring Harbor Perspect. Med. 2012, 2:a012427; b) B. L. Bassler, Daedalus 2012, 141, 67-76; c) C. Fuqua, E. P. Greenberg, Nat. Rev. Mol. Cell Biol. 2002, 3, 685-695.

[2] a) C. T. Parker, V. Sperandio, Cell. Microbiol. 2009, 11, 363-369; b) C. M. Waters, B. L. Bassler, Annu. Rev. Cell Dev. Biol. 2005, 21, 319-346.

[3] a) M. A. Welsh, H. E. Blackwell, FEMS Microbiol. Rev. 2016, 40, 774-794; b) W. R. J. D. Galloway, J. T. Hodgkinson, S. Bowden, M. Welch, D. R. Spring, Trends Microbiol. 2012, 20, 449-458; c) W. R. J. D. Galloway, J. T. Hodgkinson, S. D. Bowden, M. Welch, D. R. Spring, Chem. Rev. 2011, 111, 28-67; d) N. Amara, B. P. Krom, G. F. Kaufmann, M. M. Meijler, Chem. Rev. 2011, 111, 195-208; e) J. Njoroge, V. Sperandio, EMBO Mol. Med. 2009, 1, 201-210.

[4] a) M. A. Welsh, H. E. Blackwell, Cell Chem. Biol. 2016, 23, 361-369; b) M. C. O'Reilly, H. E. Blackwell, ACS Infect. Dis. 2016, 2, 32-38; c) M. A. Welsh, N. R. Eibergen, J. D. Moore, H. E. Blackwell, J. Am. Chem. Soc. 2015, 137, 1510-1519; d) J. D. Moore, F. M. Rossi, M. A. Welsh, K. E. Nyffeler, H. E. Blackwell, J. Am. Chem. Soc. 2015, 137, 14626-14639; e) B. C. Gorske, H. E. Blackwell, Org. Biomol. Chem. 2006, 4, 1441-1445; f) S. A. Fowler, D. M. Stacy, H. E. Blackwell, Org. Lett. 2008, 10, 2329-2332; g) Y. Tal-Gan, D. M. Stacy, M. K. Foegen, D. W. Koenig, H. E. Blackwell, J. Am. Chem. Soc. 2013, 135, 7869-7882; h) Y. Tal-Gan, M. Ivancic, G. Cornilescu, C. C. Cornilescu, H. E. Blackwell, J. Am. Chem. Soc. 2013, 135, 18436-18444; i) Y. Tal-Gan, D. M. Stacy, H. E. Blackwell, Chem. Commun. 2014, 50, 3000-3003; j) T. Yang, Y. Tal-Gan, A. E. Paharik, A. R. Horswill, H. E. Blackwell, ACS Chem. Biol. 2016; k) Y. Tal-Gan, M. Ivancic, G. Cornilescu, H. E. Blackwell, Org. Biomol. Chem. 2016, 14, 113-121; l) Y. Tal-Gan, M. Ivancic, G. Cornilescu, T. Yang, H. E. Blackwell, Angew. Chem. Int. Ed. 2016, 55.

[5] a) C. T. O'Loughlin, L. C. Miller, A. Siryaporn, K. Drescher, M. F. Semmelhack, B. L. Bassler, Proc. Natl. Acad. Sci. U.S.A. 2013, 110, 17981-17986; b) G. Chen, L. R. Swem, D. L. Swem, D. L. Stauff, C. T. O'Loughlin, P. D. Jeffrey, B. L. Bassler, F. M. Hughson, Mol. Cell 2011, 42, 199-209; c) U. Muh, B. J. Hare, B. A. Duerkop, M. Schuster, B. L. Hanzelka, R. Heim, E. R. Olson, E. P. Greenberg, Proc. Natl. Acad. Sci. U.S.A. 2006, 103, 16948-16952; d) U. Muh, M. Schuster, R. Heim, A. Singh, E. R. Olson, E. P. Greenberg, Antimicrob. Agents Chemother. 2006, 50, 3674-3679; e) B. Morkunas, W. R. J. D. Galloway, M. Wright, B. M. Ibbeson, J. T. Hodgkinson, K. M. G. O'Connell, N. Bartolucci, M. Della Valle, M. Welch, D. R. Spring, Org. Biomol. Chem. 2012, 10, 8452-8464; f) B. Morkunas, B. Gal, W. R. J. D.

Galloway, J. T. Hodgkinson, B. M. Ibbeson, Y. S. Tan, M. Welch, D. R. Spring, Beilstein J. Org. Chem. 2016, 12, 1428-1433; g) N. Amara, R. Gregor, J. Rayo, R. Dandela, E. Daniel, N. Liubin, H. M. E. Willems, A. Ben-Zvi, B. P. Krom, M. M. Meijler, ChemBioChem 2016, 17, 825-835; h) A. Delago, A. Mandabi, M. M. Meijler, Isr. J. Chem. 2016, 56, 310-320; i) N. Amara, R. Mashiach, D. Amar, P. Krief, S. A. H. Spieser, M. J. Bottomley, A. Aharoni, M. M. Meijler, J. Am. Chem. Soc. 2009, 131, 10610-10619; j) P. Mayville, G. Ji, R. Beavis, H. Yang, M. Goger, R. P. Novick, T. W. Muir, Proc. Natl. Acad. Sci. U.S.A. 1999, 96, 1218-1223; k) G. J. Lyon, P. Mayville, T. W. Muir, R. P. Novick, Proc. Natl. Acad. Sci. U.S.A. 2000, 97, 13330-13335; l) G. J. Lyon, J. S. Wright, T. W. Muir, R. P. Novick, Biochemistry 2002, 41, 10095-10104; m) J. S. Wright, G. J. Lyon, E. A. George, T. W. Muir, R. P. Novick, Proc. Natl. Acad. Sci. U.S.A. 2004, 101, 16168-16173; n) E. A. George, R. P. Novick, T. W. Muir, J. Am. Chem. Soc. 2008, 130, 4914-4924; o) B. Wang, A. Zhao, R. P. Novick, T. W. Muir, Mol. Cell 2014, 53, 929-940; p) J. G. Johnson, B. Wang, G. T. Debelouchina, R. P. Novick, T. W. Muir, ChemBioChem 2015, 16, 1093-1100; q) P. McDowell, Z. Affas, C. Reynolds, M. T. Holden, S. J. Wood, S. Saint, A. Cockayne, P. J. Hill, C. E. Dodd, B. W. Bycroft, W. C. Chan, P. Williams, Mol. Microbiol. 2001, 41, 503-512; r) R. J. Scott, L.-Y. Lian, S. H. Muharram, A. Cockayne, S. J. Wood, B. W. Bycroft, P. Williams, W. C. Chan, Bioorg. Med. Chem. Lett. 2003, 13, 2449-2453; s) C. L. Malone, B. R. Boles, K. J. Lauderdale, M. Thoendel, J. S. Kavanaugh, A. R. Horswill, J. Microbiol. Methods 2009, 77, 251-260; t) B. Wang, Tom W. Muir, Cell Chem. Biol. 2016, 23, 214-224; u) J. J. Ciardiello, W. R. J. D. Galloway, C. J. O'Connor, H. F. Sore, J. E. Stokes, Y. T. Wu, D. R. Spring, Tetrahedron 2016, 72, 3567-3578; v) A. Delago, A. Mandabi, M. M. Meijler, Isr. J. Chem. 2016, 56, 310-320.

[6] a) M. J. Kratochvil, Y. Tal-Gan, T. Yang, H. E. Blackwell, D. M. Lynn, ACS Biomat. Sci. Eng. 2015, 1, 1039-1049; b) A. H. Broderick, D. M. Stacy, Y. Tal-Gan, M. J. Kratochvil, H. E. Blackwell, D. M. Lynn, Adv. Healthcare Mater. 2014, 3, 97-105.

[7] a) K. Y. Le, M. Otto, Front. Microbiol. 2015, 6, 1174; b) M. Thoendel, J. S. Kavanaugh, C. E. Flack, A. R. Horswill, Chem. Rev. 2011, 111, 117-151; c) R. P. Novick, E. Geisinger, Annu. Rev. Genet. 2008, 42, 541-564.

[8] a) V. Thammavongsa, H. K. Kim, D. Missiakas, O. Schneewind, Nat. Rev. Microbiol. 2015, 13, 529-543; b) S. Y. Queck, M. Jameson-Lee, A. E. Villaruz, T.-H. L. Bach, B. A. Khan, D. E. Sturdevant, S. M. Ricklefs, M. Li, M. Otto, Mol. Cell 2008, 32, 150-158; c) R. P. Novick, H. F. Ross, S. J. Projan, J. Kornblum, B. Kreiswirth, S. Moghazeh, EMBO J. 1993, 12, 3967-3975.

[9] a) G. Ji, R. Beavis, R. P. Novick, Science 1997, 276, 2027-2030; b) R. P. Novick, S. J. Projan, J. Kornblum, H. F. Ross, G. Ji, B. Kreiswirth, F. Vandenesch, S. Moghazeh, Mol. Gen. Genet. 1995, 248, 446-458.

[10] a) L. Zhang, J. Lin, G. Ji, J. Biol. Chem. 2004, 279, 19448-19456; b) R. D. Qiu, W. H. Pei, L. S. Zhang, J. Q. Lin, G. Y. Ji, J. Biol. Chem. 2005, 280, 16695-16704; c) J. S. Kavanaugh, M. Thoendel, A. R. Horswill, Mol. Microbiol. 2007, 65, 780-798.

[11] S. Jarraud, G. J. Lyon, A. M. S. Figueiredo, L. Gerard, F. Vandenesch, J. Etienne, T. W. Muir, R. P. Novick, J. Bacteriol. 2000, 182, 6517-6522.

[12] a) R. K. Gupta, T. T. Luong, C. Y. Lee, Proc. Natl. Acad. Sci. U.S.A. 2015, 112, 14036-14041; b) S. Boisset, T. Geissmann, E. Huntzinger, P. Fechter, N. Bendridi, M. Possedko, C. Chevalier, A. C. Helfer, Y. Benito, A. Jacquier, C. Gaspin, F. Vandenesch, P. Romby, Genes Dev. 2007, 21, 1353-1366.

[13] G. J. Lyon, J. S. Wright, A. Christopoulos, R. P. Novick, T. W. Muir, J. Biol. Chem. 2002, 277, 6247-6253.

[14] J. S. Wright, R. Jin, R. P. Novick, Proc. Natl. Acad. Sci. U.S.A. 2005, 102, 1691-1696.

[15] M. M. Peterson, J. L. Mack, P. R. Hall, A. A. Alsup, S. M. Alexander, E. K. Sully, Y. S. Sawires, A. L. Cheung, M. Otto, H. D. Gresham, Cell Host Microbe 2008, 4, 555-566.

[16] W. Chan, P. White, Fmoc Solid Phase Peptide Synthesis: A Practical Approach,
OUP Oxford, 2000.

[17] a) C. P. Montgomery, S. Boyle-Vavra, P. V. Adem, J. C. Lee, A. N. Husain, J. Clasen, R. S. Daum, J. Infect. Dis. 2008, 198, 561-570; b) CDC, Morb. Mortal. Weekly Rep. 2003, 52, 793-795; c) CDC, Morb. Mortal. Weekly Rep. 2003, 52, 992-996.

[18] Compound n9FF was not tested in the group-IV *S. aureus* reporter, as the one-carbon smaller homolog n8FF was found to be less active in this group relative to n7FF and t-AIP-II.

[19] a) C. D. Schwieters, J. J. Kuszewski, N. Tjandra, G. M. Clore, J. Magn. Reson. 2003, 160, 66-74; b) C. D. Schwieters, J. J. Kuszewski, G. M. Clore, Prog. Nucl. Magn. Reson. Spectrosc. 2006, 48, 47-62.

[20] D. Eisenberg, E. Schwarz, M. Komaromy, R. Wall, J. Mol. Biol. 1984, 179, 125-142.

[21] a) J. M. Yarwood, D. J. Bartels, E. M. Volper, E. P. Greenberg, J. Bacteriol. 2004, 186, 1838-1850; b) R. N. Kirchdoerfer, A. L. Garner, C. E. Flack, A. R. Horswill, K. D. Janda, G. F. Kaufmann, I. A. Wilson, J. Biol. Chem. 2011, 286, 17351-17358.

[22] C. L. Malone, B. R. Boles, A. R. Horswill, Appl. Environ. Microbiol. 2007, 73, 6036-6044.

[23] K. Wüthrich, NMR of Proteins and Nucleic Acids, John Wiley and Sons: New York, 1986.

[24] C. D. Schwieters, G. M. Clore, J. Magn. Reson. 2001, 152, 288-302.

[25] M. Nilges, G. M. Clore, A. M. Gronenborn, FEBS Lett. 1988, 229, 317-324.

[26] G. M. Clore, J. Kuszewski, J. Am. Chem. Soc. 2002, 124, 2866-2867.

[27] C. D. Schwieters, G. M. Clore, J. Phys. Chem. B 2008, 112, 6070-6073.

[28] The PyMOL Molecular Graphics System, Version 1.7, Schrödinger, LLC., 2015.

[29] A. W. Schuttelkopf, D. M. F. van Aalten, Acta Crystallogr. Sect. D. Biol. Crystallogr. 2004, 60, 1355-1363.

[30] A. K. Ghose, G. M. Crippen, J. Chem. Inf. Comput. Sci. 1987, 27, 21-35.

[31] V. N. Viswanadhan, A. K. Ghose, G. R. Revankar, R. K. Robins, J. Chem. Inf. Comput. Sci. 1989, 29, 163-172.

[32] Bio-Loom, Version 1.6, BioByte Corp., Claremont, Calif. 91711, 2015.

[33] Web site: www.molinspiration.com, Molinspiration Cheminformatics, Version 2014.11, 2016.

[34] J. K. Vasquez, Y. Tal-Gan, G. Cornilescu, K. A. Tyler, and H. E. Blackwell. "Simplified AIP-II Peptidomimetics are Potent Inhibitors of *Staphylococcus aureus* AgrC Quorum Sensing Receptors." ChemBioChem. January 2017, 18, 413-423.

We claim:

1. A compound of formula:

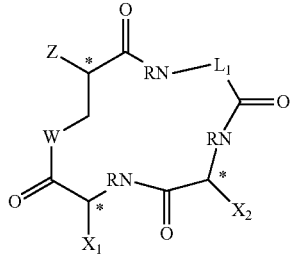

or salts or solvates thereof,
where:
carbons indicated by * are independently in the L- or R-stereochemical form and the compound can be racemic, non-racemic or substantially enantiomerically pure;
W is NH or NCH$_3$;
Z is NR$_3$CO—R$_2$, where R$_3$ is hydrogen or a C1-C3 alkyl, and R$_2$ is hydrogen, an optionally-substituted alkyl group having 1-12 carbon atoms, an optionally-substituted cycloalkyl group having 3-12 carbon atoms, an optionally-substituted arylalkyl group, an optionally-substituted heteroarylalkyl group, an optionally-substituted heterocyclylalkyl group, an optionally-substituted cycloalkylalkyl group, an optionally-substituted aryl group, an optionally-substituted heteroaryl group, an optionally-substituted heterocyclyl group or an alkoxyalkyl group having 1-12 carbon atoms and 1-4 oxygen atoms;
L$_1$ is —(CH$_2$)n-, where n is 2-12, or an alkoxyalkylene having 2-12 carbons and 1-4 oxygens;
each R, independently, is hydrogen or a straight-chain or branched alkyl group having 1-3 carbon atoms; and
X$_1$ and X$_2$ are independently selected from the group consisting of optionally-substituted straight-chain or branched alkyl groups having 3-8 carbon atoms, optionally-substituted cycloalkyl groups having 3-12 carbon atoms, optionally-substituted aryl, optionally-substituted heteroaryl, optionally-substituted heterocyclyl, optionally-substituted cycloalkylalkyl, optionally-substituted arylalkyl, optionally-substituted heteroarylalkyl and optionally-substituted heterocyclylalkyl groups;
wherein optional substitution is substitution with one or more groups selected from the group consisting of halogen, hydroxyl, nitro, cyano, isocyano, oxo, thioxo, azide, cyanate, isocyanate, acyl, haloakyl, alkyl, alkenyl, alkynyl, phenyl, halo-substituted phenyl, alkyl-substituted phenyl, benzyl, halo-substituted benzyl, alkyl-substituted benzyl, alkoxy, alkylthio, and mercapto.

2. The compound of claim 1 of formula:

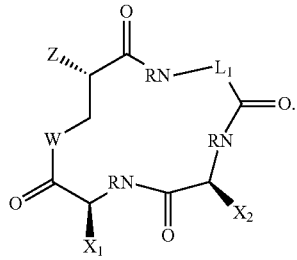

or salts or solvates thereof.

3. The compound of claim 2, wherein:
L$_1$ is —(CH$_2$)$_n$—, where n is 2-9; or
L$_1$ is an alkoxyalkylene having 2-8 carbons and 1-3 oxygens.

4. The compound of claim 1, wherein X$_1$ and X$_2$ are selected from sec-butyl, isobutyl, benzyl, p-OH-benzyl, p-F-benzyl, p-Cl-benzyl, m-F-benzyl, m-Cl-benzyl, cyclohexyl, cyclopentyl, or 3-indolylmethyl.

5. The compound of claim 1, wherein X$_1$ and X$_2$ are optionally-substituted benzyl groups, where optional substitution is substitution with one or more halogen, hydroxyl, alkyl or alkoxy.

6. The compound of claim 1 of formula:

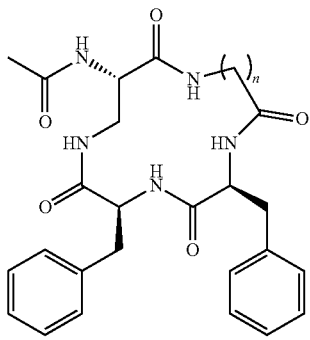

or salts or solvates thereof,
wherein n is 7 or 8.

7. A pharmaceutical composition comprising one or more compounds of claim 1 and a pharmaceutically acceptable carrier.

8. A method for regulating virulence in *Staphylococcus* that comprises the step of contacting the bacterium with one or more compounds selected from the compounds of claim 1.

9. The method of claim 8 for attenuating virulence in a strain of *Staphylococcus*.

10. A method of treating staphylococcal infection which comprises administering to an individual in need of treatment a therapeutically effective amount of one or more compounds of claim 1.

11. The method of claim 10, wherein the staphylococcal infection is caused by a strain of *S. aureus, S. epidermidis* or both.

12. A compound of formula:

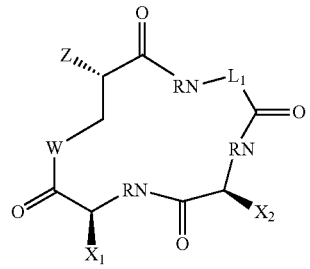

or salts or solvates thereof,
where:
W is S or $NR_1$, where $R_1$ is hydrogen or an alkyl group having 1 to 3 carbon atoms;
each R is hydrogen or methyl;
Z is $-NR_3CO-R_2$, where $R_3$ is hydrogen or a C1-C3 alkyl, and $R_2$ is hydrogen, an optionally-substituted alkyl group having 1-12 carbon atoms, an optionally-substituted cycloalkyl group having 3-12 carbon atoms, an optionally-substituted arylalkyl group, an optionally-substituted heteroarylalkyl group, an optionally-substituted heterocyclylalkyl group, an optionally-substituted cycloalkylalkyl group, an optionally-substituted aryl, an optionally-substituted heteroaryl group, an optionally-substituted heterocyclyl group or an alkoxyalkyl group having 1-12 carbon atoms and 1-4 oxygen atoms; wherein optional substitution of $R_2$ is substitution with one or more groups selected from the group consisting of halogen, hydroxyl, nitro, cyano, isocyano, oxo, thioxo, azide, cyanate, isocyanate, acyl, haloakyl, alkyl, alkenyl, alkynyl, phenyl, halo-substituted phenyl, alkyl-substituted phenyl, benzyl, halo-substituted benzyl, alkyl-substituted benzyl, alkoxy, alkylthio, and mercapto;

$X_1$ and $X_2$ are optionally substituted benzyl, cyclohexyl, cyclopentyl, or 3-indolylmethyl, where optional substitution is substitution with one or more halogen, hydroxyl, alkyl or alkoxy; and $L_1$ is an alkoxyalkylene having 2-8 carbons and 1-3 oxygens.

13. The compound of claim 12, where $L_1$ is $-CH_2-CH_2-O-CH_2-CH_2-O-CH_2-$.

14. The compound of claim 12, where $X_1$ and $X_2$ are optionally substituted benzyl.

15. The compound of claim 12, where W is S.

16. The compound of claim 15, where $L_1$ is $-CH_2-CH_2-O-CH_2-CH_2-O-CH_2-$.

17. The compound of claim 16, where $X_1$ and $X_2$ are both optionally substituted benzyl.

18. The compound of claim 16, where $X_1$ and $X_2$ are benzyl, p-OH-benzyl, p-F-benzyl, p-Cl-benzyl, m-F-benzyl, or m-Cl-benzyl.

19. The compound of claim 12 which is n7OFF:

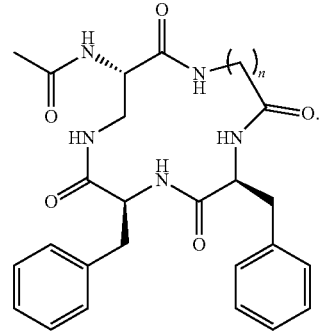

20. The compound of claim 12, wherein optional substitution of $R_2$ is substitution with one or more halogen, hydroxyl, alkyl or alkoxy.

21. The compound of claim 12, wherein $R_3$ is hydrogen or a methyl group and $R_2$ is hydrogen or an optionally-substituted alkyl group having 1-12 carbon atoms.

22. A compound, wherein $R_3$ is hydrogen or a methyl group and $R_2$ is an unsubstituted alkyl group having 1-4 carbon atoms.

23. The compound of claim 12, wherein Z is $CH_3-CO-NH-$.

24. The compound of claim 12, wherein W is NR₁.

25. The compound of claim 1, of formula:

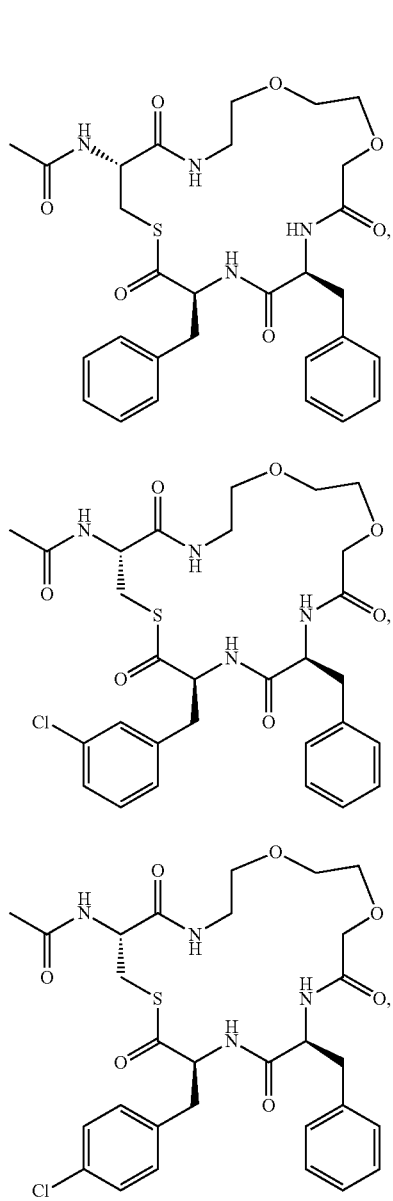

n7OFF n7OF3clF n7OF4clF n7OF3fF

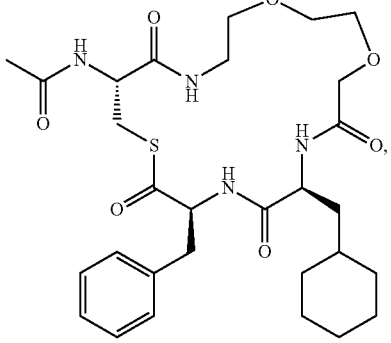

n7OChaF

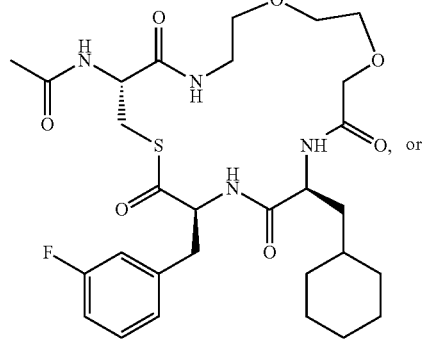

n7OCha3fF

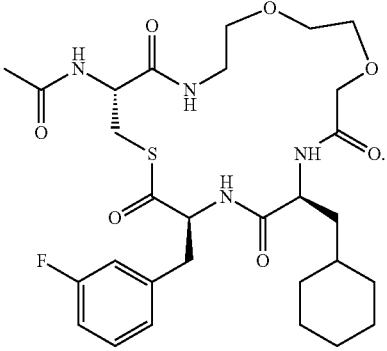

n7Cha3fF

26. A pharmaceutical composition comprising one or more compounds of claim 12 and a pharmaceutically acceptable carrier.

27. The compound of claim 2, wherein:

L₁ is —(CH₂)ₙ—, where n is 3-8; or

L₁ is an alkoxyalkylene having 3 or 4 carbons and 1 oxygen, or having 4, 5 or 6 carbons and 2 oxygens.

28. The compound of claim 1, wherein:

R₃ is hydrogen or a methyl group and

R₂ is an unsubstituted alkyl group having 1-4 carbon atoms.

29. The compound of claim 1, wherein Z is CH₃—CO—NH—.

30. A method for regulating virulence in *Staphylococcus* that comprises the step of contacting the bacterium with one or more compounds selected from the compounds of claim 12.

31. The method of claim 30 for attenuating virulence in a strain of *Staphylococcus*.

32. The method of claim 31, wherein the production of toxic shock syndrome toxin-1 is attenuated.

33. A method of treating staphylococcal infection which comprises administering to an individual in need of treatment a therapeutically effective amount of one or more compounds of claim 12.

34. The method of claim 33, wherein the staphylococcal infection is caused by a strain of *S. aureus, S. epidermidis* or both.

35. A compound of formula:

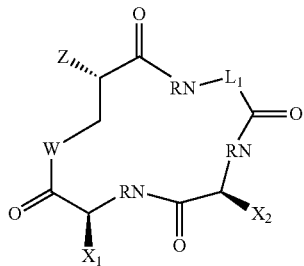

or salts or solvates thereof,
where:
W is S or $NR_1$, where $R_1$ is hydrogen or an alkyl group having 1 to 3 carbon atoms;
each R is hydrogen or methyl;
Z is $-NR_3CO-R_2$, where $R_3$ is hydrogen or a C1-C3 alkyl, and $R_2$ is hydrogen, an optionally-substituted alkyl group having 1-12 carbon atoms, an optionally-substituted cycloalkyl group having 3-12 carbon atoms, an optionally-substituted arylalkyl group, an optionally-substituted heteroarylalkyl group, an optionally-substituted heterocyclylalkyl group, an optionally-substituted cycloalkylalkyl group, an optionally-substituted aryl, an optionally-substituted heteroaryl group, an optionally-substituted heterocyclyl group or an alkoxyalkyl group having 1-12 carbon atoms and 1-4 oxygen atoms;
$X_1$ and $X_2$ are independently selected from the group consisting of optionally-substituted straight-chain or branched alkyl groups having 3-8 carbon atoms, optionally-substituted cycloalkyl groups having 3-12 carbon atoms, optionally-substituted aryl, optionally-substituted heteroaryl, optionally-substituted heterocyclyl, optionally-substituted cycloalkylalkyl, optionally-substituted arylalkyl, optionally-substituted heteroarylalkyl and optionally-substituted heterocyclylalkyl groups, wherein optional substitution is substitution with one or more groups selected from the group consisting of halogen, hydroxyl, nitro, cyano, isocyano, oxo, thioxo, azide, cyanate, isocyanate, acyl, haloakyl, alkyl, alkenyl, alkynyl, phenyl, halo-substituted phenyl, alkyl-substituted phenyl, benzyl, halo-substituted benzyl, alkyl-substituted benzyl, alkoxy, alkylthio, and mercapto; and
$L_1$ is an alkoxyalkylene having 2-8 carbons and 1-3 oxygens.

36. The compound of claim 35, wherein:
$R_3$ is hydrogen or a methyl group and
$R_2$ is an unsubstituted alkyl group having 1-4 carbon atoms.

37. The compound of claim 35, wherein Z is $CH_3-CO-NH-$.

38. The compound of claim 35, wherein $L_1$ is $-CH_2-CH_2-O-CH_2-CH_2-O-CH_2-$.

39. A method of treating staphylococcal infection which comprises administering to an individual in need of treatment a therapeutically effective amount of one or more compounds of claim 35.

40. The method of claim 39, wherein the staphylococcal infection is caused by a strain of *S. aureus, S. epidermidis* or both.

41. A pharmaceutical composition comprising one or more compounds of claim 35 and a pharmaceutically acceptable carrier.

42. A method for regulating virulence in *Staphylococcus* that comprises the step of contacting the bacterium with one or more compounds selected from the compounds of claim 35.

43. The method of claim 42 for attenuating virulence in a strain of *Staphylococcus*.

* * * * *

SEQUENCE LISTING

<160> NUMBER OF SEQ ID NOS: 6

<210> SEQ ID NO 1
<211> LENGTH: 8
<212> TYPE: PRT
<213> ORGANISM: Staphylococcus aureus
<220> FEATURE:
<221> NAME/KEY: MISC_FEATURE
<222> LOCATION: (4)..(8)
<223> OTHER INFORMATION: cyclic

<400> SEQUENCE: 1

Tyr Ser Thr Cys Asp Phe Ile Met
1               5

<210> SEQ ID NO 2
<211> LENGTH: 9
<212> TYPE: PRT
<213> ORGANISM: Staphylococcus aureus
<220> FEATURE:
<221> NAME/KEY: MISC_FEATURE
<222> LOCATION: (5)..(9)
<223> OTHER INFORMATION: cyclic

<400> SEQUENCE: 2

Gly Val Asn Ala Cys Ser Ser Leu Phe
1               5

<210> SEQ ID NO 3
<211> LENGTH: 7
<212> TYPE: PRT
<213> ORGANISM: Staphylococcus aureus
<220> FEATURE:
<221> NAME/KEY: MISC_FEATURE
<222> LOCATION: (3)..(7)
<223> OTHER INFORMATION: cyclic

<400> SEQUENCE: 3

Ile Asn Cys Asp Phe Leu Leu
1               5

<210> SEQ ID NO 4
<211> LENGTH: 8
<212> TYPE: PRT
<213> ORGANISM: Staphylococcus aureus
<220> FEATURE:
<221> NAME/KEY: MISC_FEATURE
<222> LOCATION: (4)..(8)
<223> OTHER INFORMATION: cyclic

<400> SEQUENCE: 4

Tyr Ser Thr Cys Tyr Phe Ile Met
1               5

<210> SEQ ID NO 5
<211> LENGTH: 5
<212> TYPE: PRT
<213> ORGANISM: artificial
<220> FEATURE:
<223> OTHER INFORMATION: synthetic peptide
<220> FEATURE:
<221> NAME/KEY: MISC_FEATURE
<222> LOCATION: (1)..(5)
<223> OTHER INFORMATION: cyclic
<220> FEATURE:
<221> NAME/KEY: MISC_FEATURE
<222> LOCATION: (1)..(1)
<223> OTHER INFORMATION: acetylated

<400> SEQUENCE: 5

```
Cys Ser Asn Tyr Leu
1               5

<210> SEQ ID NO 6
<211> LENGTH: 7
<212> TYPE: PRT
<213> ORGANISM: artificial
<220> FEATURE:
<223> OTHER INFORMATION: synthetic peptide
<220> FEATURE:
<221> NAME/KEY: MISC_FEATURE
<222> LOCATION: (3)..(7)
<223> OTHER INFORMATION: cyclic

<400> SEQUENCE: 6

Ile Asn Cys Ala Phe Leu Leu
1               5
```